United States Patent [19]

McDowell

[11] Patent Number: 5,030,743

[45] Date of Patent: Jul. 9, 1991

[54] ORGANOMETALLIC SOLAR VOLTAIC STORAGE CELL

[76] Inventor: Mathew E. McDowell, 20 E. Hyde Park, St. Joseph, Mo. 64504

[21] Appl. No.: 102,534

[22] Filed: Sep. 29, 1987

[51] Int. Cl.$^5$ .............................................. C07F 15/02
[52] U.S. Cl. .................................................. 556/148
[58] Field of Search ....................... 556/148; 252/182.1

[56] References Cited

U.S. PATENT DOCUMENTS

| | | | |
|---|---|---|---|
| 2,115,399 | 4/1938 | Ruben | 429/111 |
| 3,718,458 | 2/1973 | Ritcey et al. | 423/139 |
| 3,879,228 | 4/1975 | Theodorou et al. | 429/111 |
| 3,989,542 | 11/1976 | Clark | 429/111 |
| 4,052,536 | 10/1977 | Lichtin et al. | 429/105 |
| 4,120,817 | 10/1978 | Hummelstedt et al. | 423/139 |
| 4,190,705 | 2/1980 | Brokken-Zijp | 429/111 |
| 4,303,704 | 12/1981 | Courdevelis et al. | 423/139 |
| 4,466,867 | 8/1984 | Habermann et al. | 204/91 |
| 4,565,673 | 1/1986 | Kataoka et al. | 423/139 |
| 4,608,136 | 8/1986 | Vaughan et al. | 423/138 |
| 4,765,834 | 8/1988 | Ananthapadmanabhan et al. | 423/139 |

*Primary Examiner*—Gary P. Straub
*Assistant Examiner*—Stuart L. Hendrickson
*Attorney, Agent, or Firm*—Bacon & Thomas

[57] ABSTRACT

The present invention provides novel metal complexes and solutions containing the complexes which are useful for converting light energy into electrical energy. The complexes are formed by complexing certain metals, such as iron, with a carboxyl compound, chloride and ammonia to form a complex having carboxyl ligands, chloride ligands and ammonia ligands. The preferred carboxyl compound is citric acid, acetic acid or salts thereof. The invention also provides a solar cell which comprises a transparent container which contains a pair of electrodes immersed in the metal complex.

9 Claims, 27 Drawing Sheets

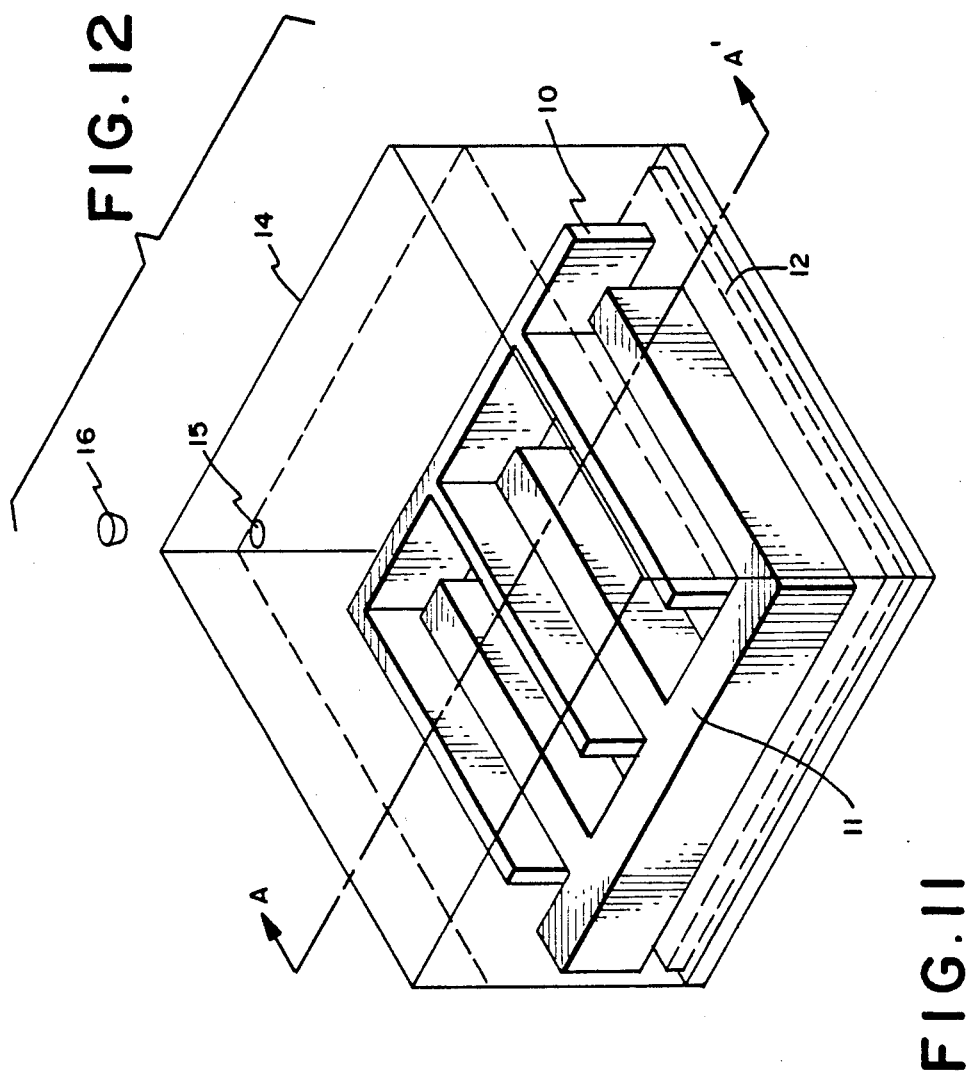
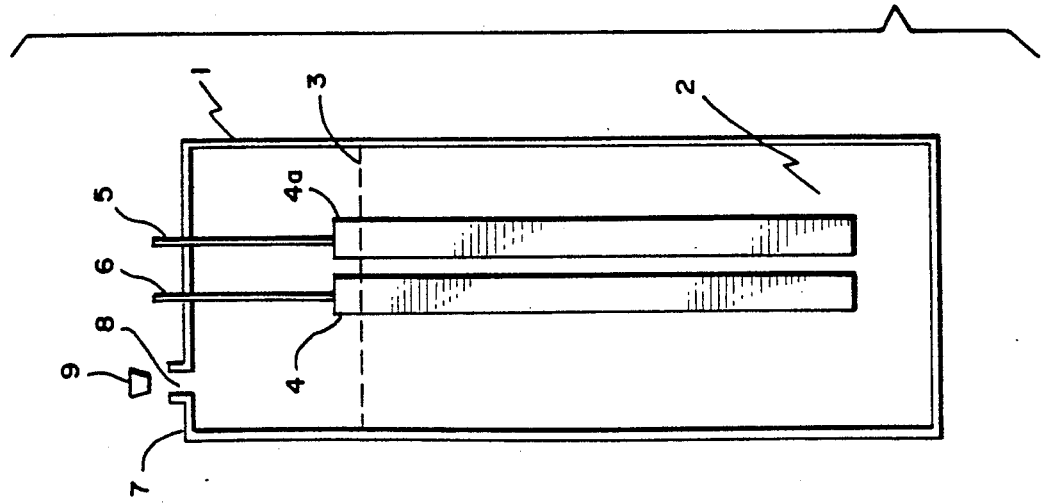

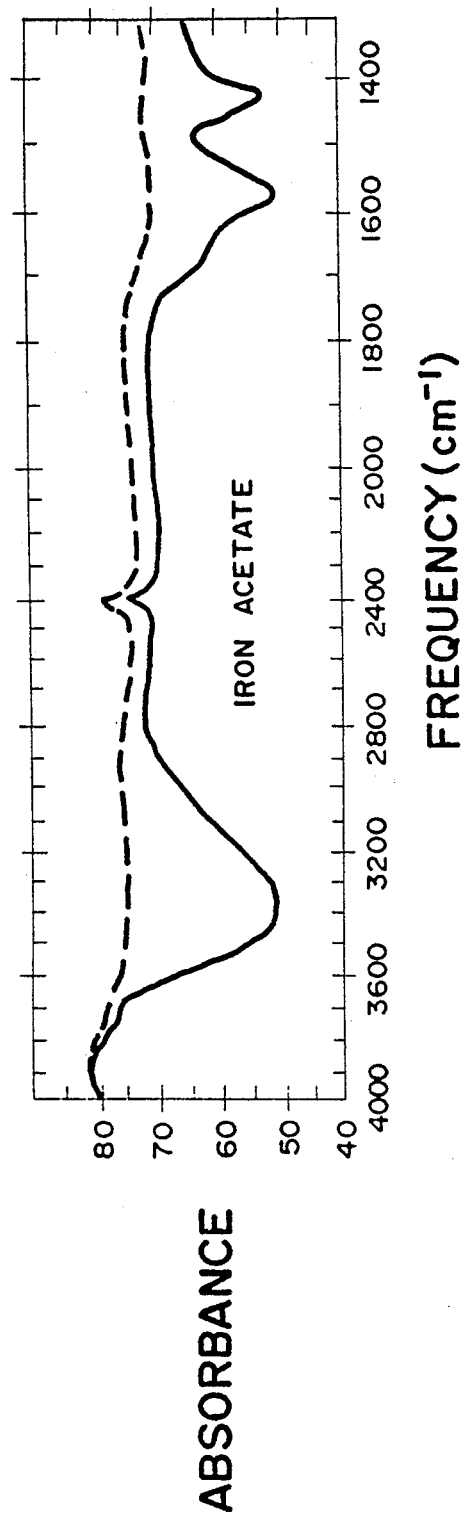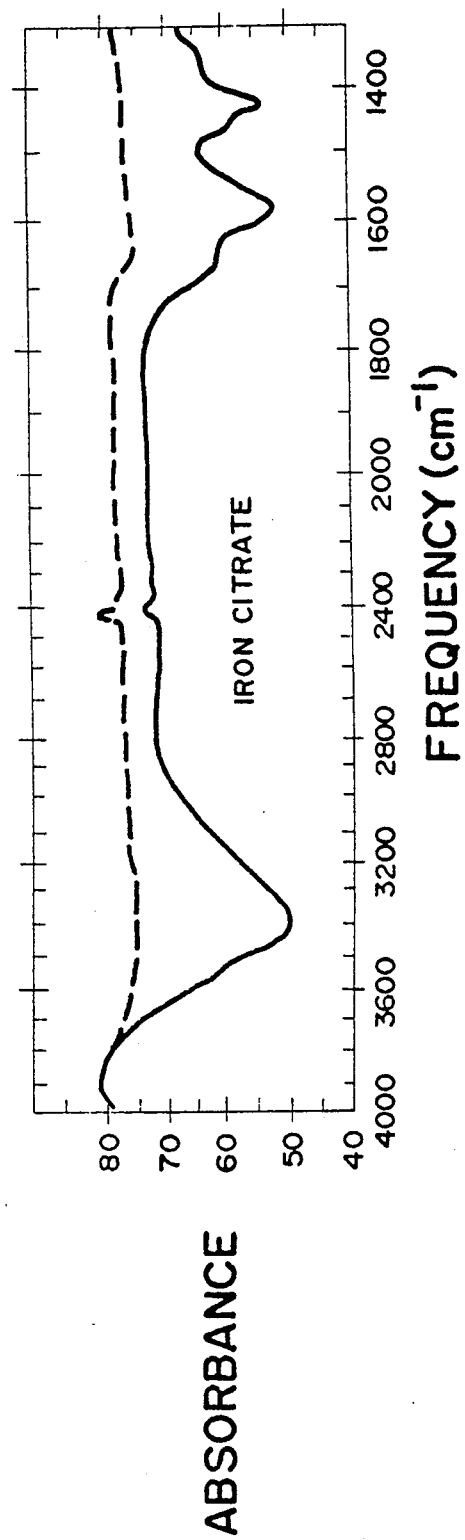

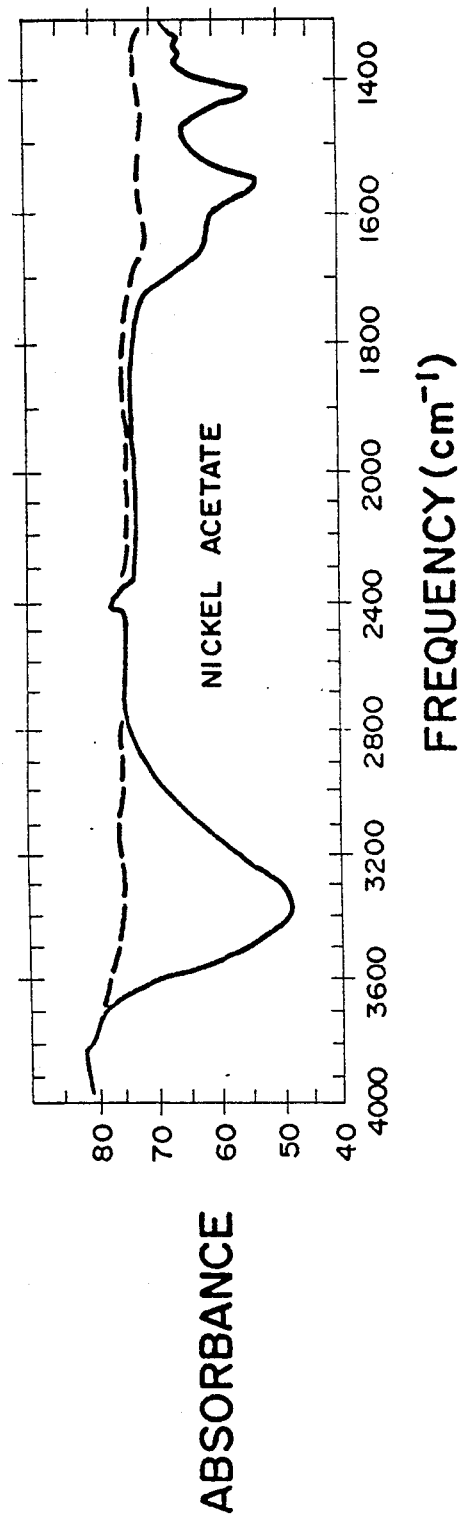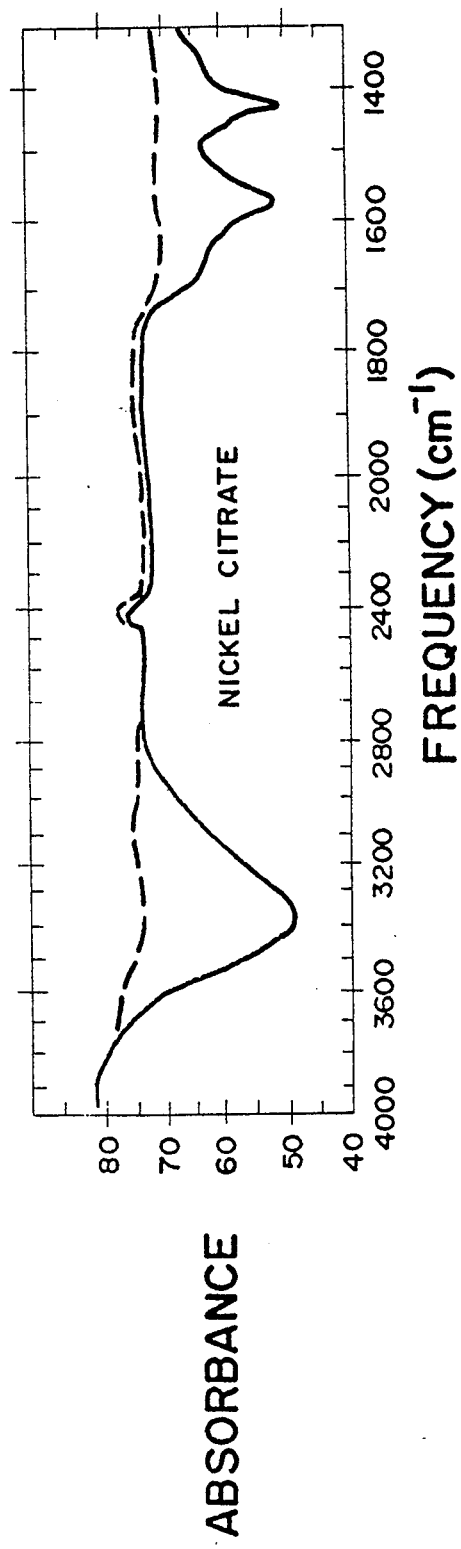

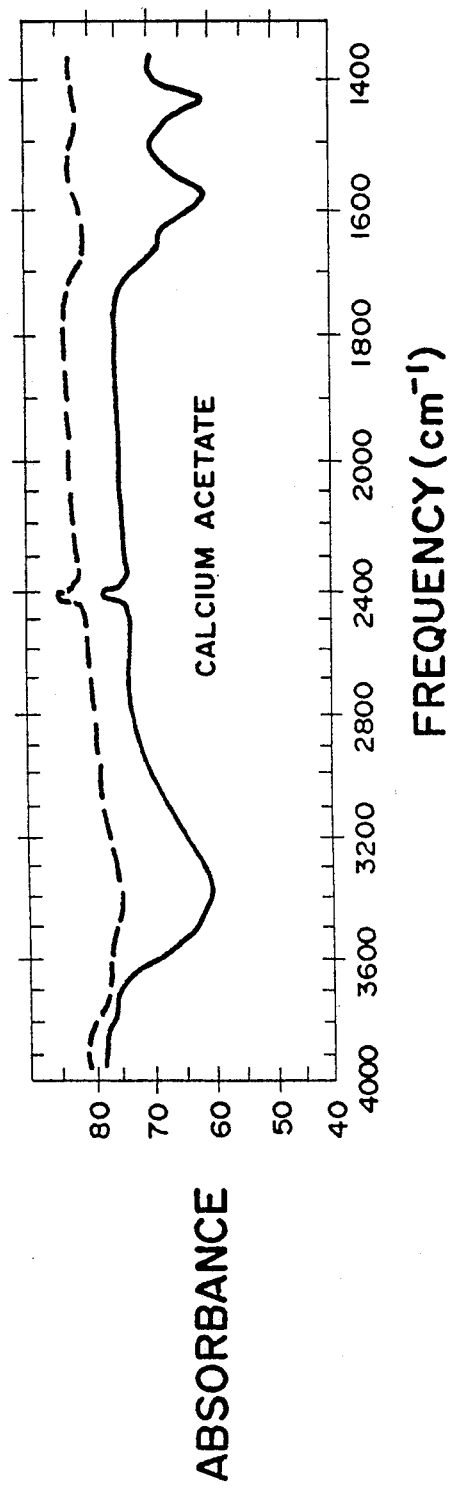
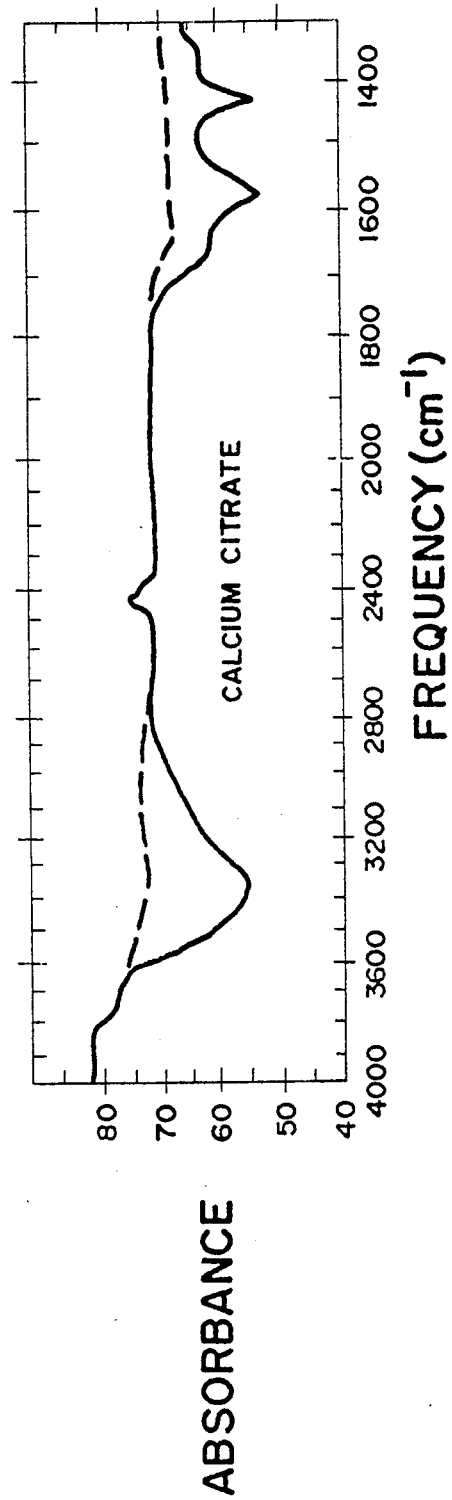

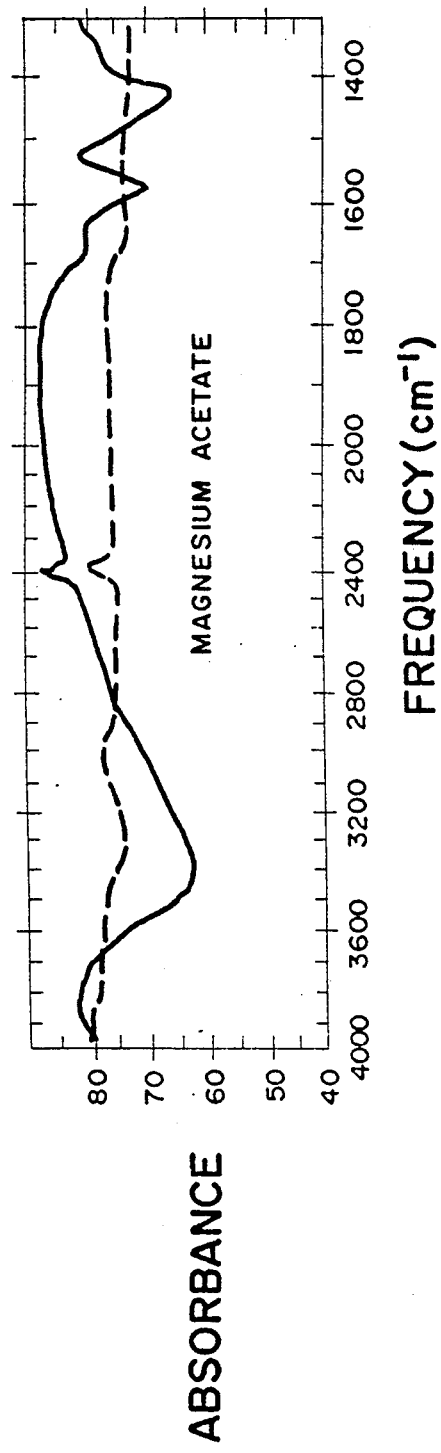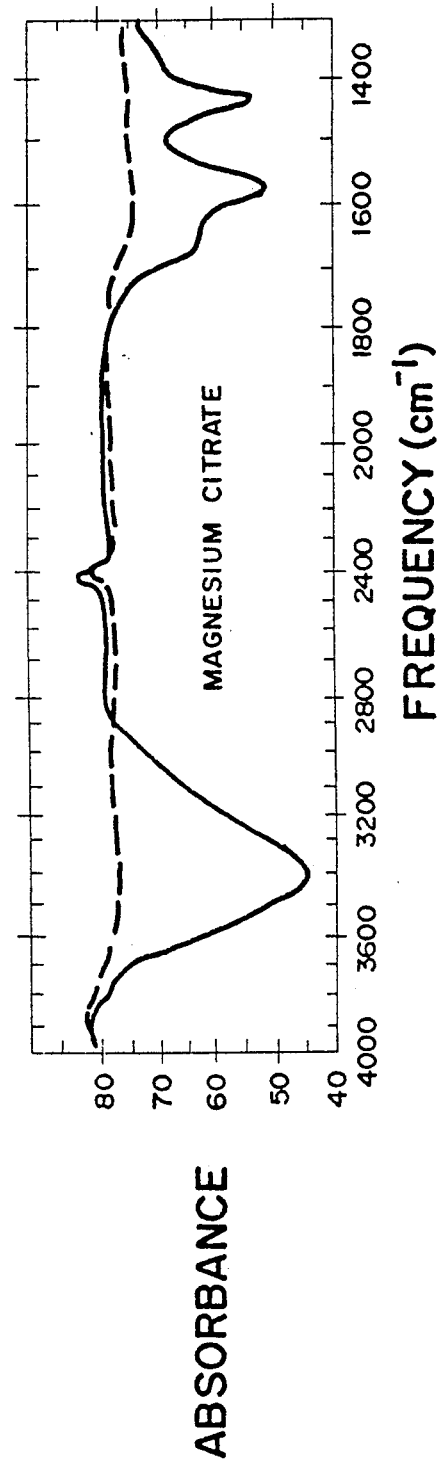

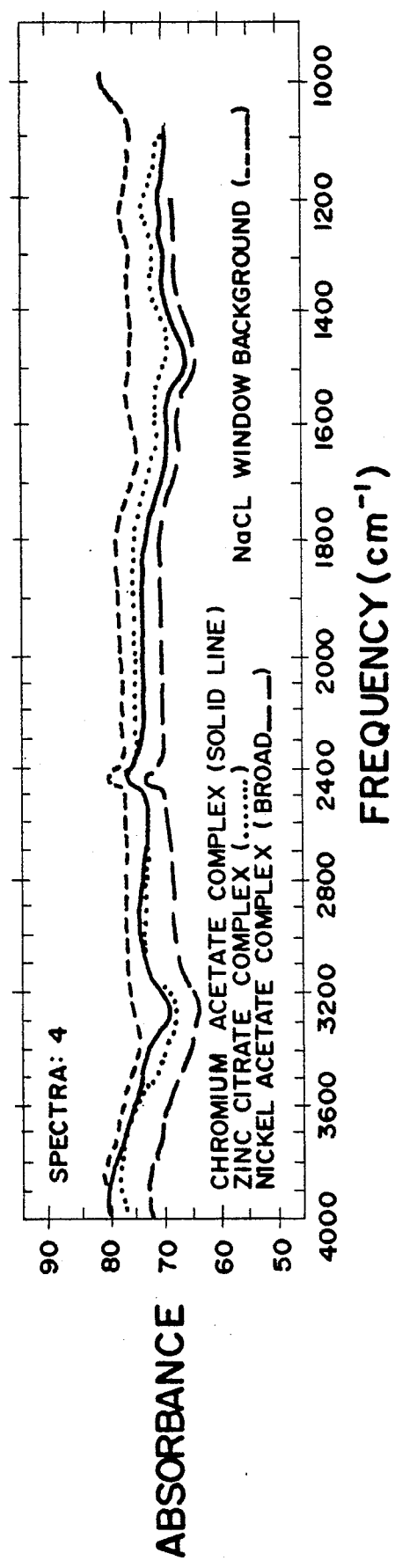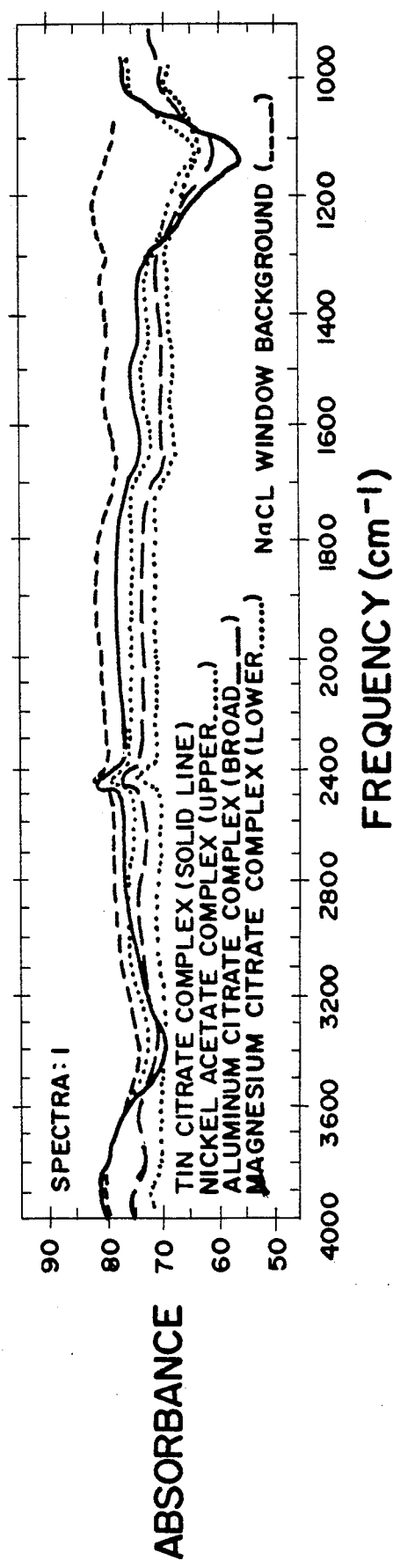

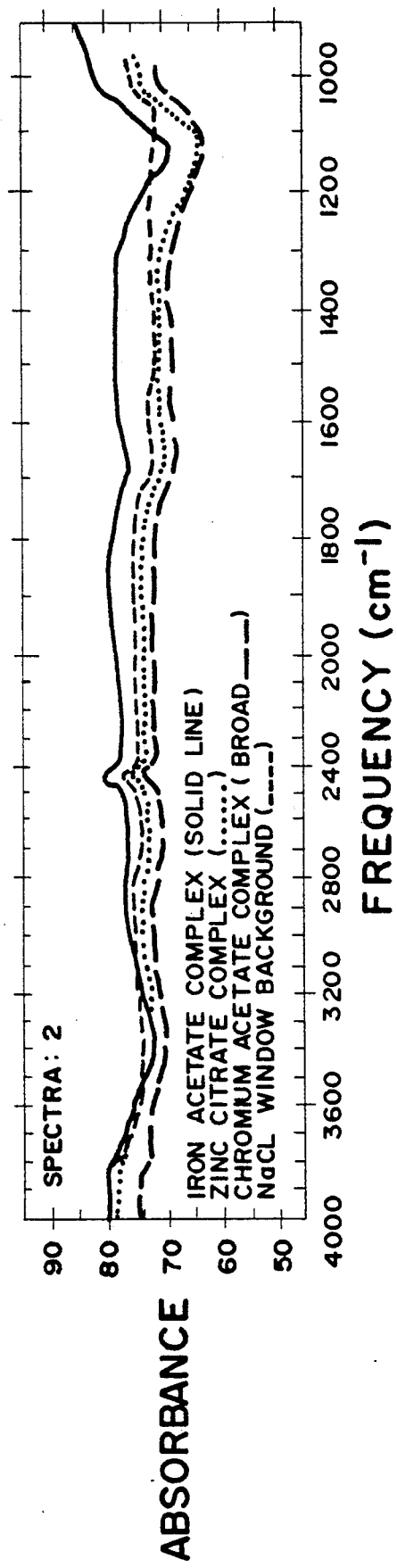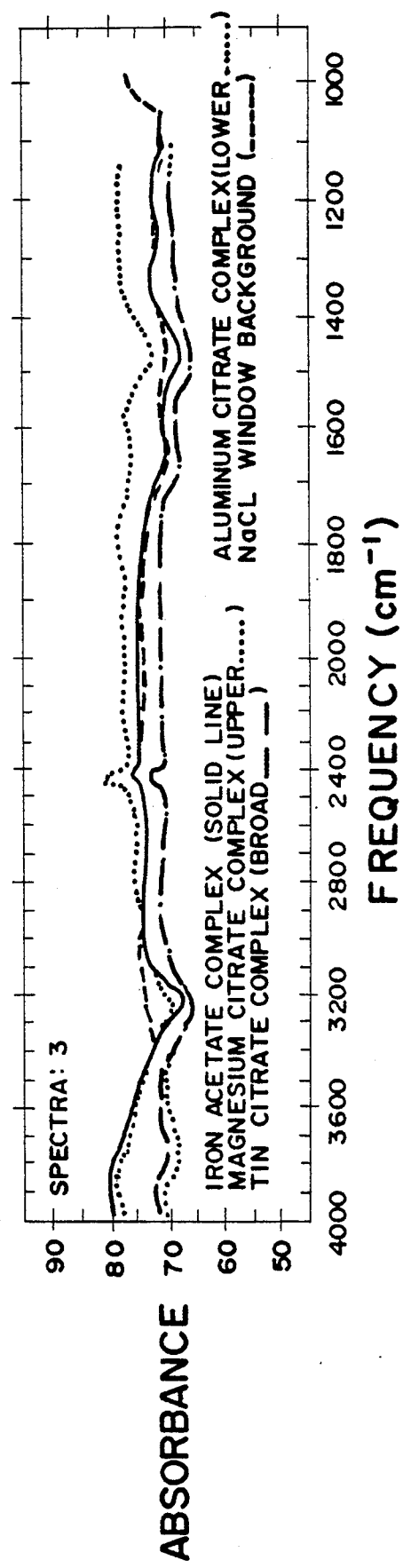

ORGANOMETALLIC SOLAR VOLTAIC STORAGE CELL

BACKGROUND OF THE INVENTION

1. Field of the Invention

The present invention relates to solar voltaic storage cells which are capable of generating and storing electrical energy due to the action of sunlight on a cell having a pair of electrodes immersed in certain types of metallic complex solutions. The invention also relates to novel carboxyl metallic and related organometallic complexes for use in the solar cells.

2. Background Information

Generation of electrical power in the United States involves a heavy dependence on fossil fuels and nuclear energy, both of which have serious environmental consequences which make these sources of energy less than desirable. Alternative sources of electrical energy, particularly solar electrical generators, have been developed for a cleaner production of electricity without the environmental hazards which are associated with nuclear and fossil fuel generators. A typical device for generating electricity from sunlight utilizes certain light sensitive chemicals in a solution having electrodes immersed therein. One such device which utilizes a solution of light sensitive chemical is disclosed in U.S. Pat. No. 4,190,705. U.S. Pat. No. 4,190,705 discloses a photogalvanic cell which produces electricity due to the interaction of light with a specific light sensitive solution within the cell having one-half cell exposed to light and the other half cell exposed to dark. The light sensitive solution is acidic and contains a dye such a thionine and a metal redox couple such as $Fe^{+2}/Fe^{+3}$. Each half cell contains an electrode. The reaction at the electrode exposed to light is: $Th + Fe^{+2} \rightarrow Fe^{+3} + Th^-$ and the reaction at the dark electrode is $Fe^{+3} + e^- \rightarrow Fe^{+2}$.

When the half cells are electrically connected, a current flows from the electrode exposed to light to the electrode exposed to dark. However, a reverse reaction at the dark electrode diminishes the efficiency of the cell. The reverse reaction is: $Fe^{+3} + Th^- \rightarrow Fe^{+2} + Th$.

In order to minimize the loss of efficiency due to the reverse reaction, the reverse reaction is suppressed by adding a complexing agent to the solution. The reverse reaction is suppressed due to the formation of a complex with the higher valent ion (e.g., $Fe^{+3}$) of the redox complex. Suitable complexes for suppressing the reverse reaction are formed by adding fluoride ions, phosphate ions, citrate ions, oxalate ions or 2-amino-propionate ions to the cell containing the dye and redox couple.

It will be readily appreciated that certain deficiencies exist with respect to the device described in U.S. Pat. No. 4,190,705. Most notable, it will be observed that the device requires that one of the electrodes be kept in the dark while the other electrode is exposed to light. Such an arrangement requires a more complex structure to assure that light does not enter into one of the half cells. In addition, the device requires the presence of thionine to carry the charge to the electrode. The presence of thionine is disadvantageous because of the above described reverse reaction which takes place at the dark electrode.

Also, U.S. Pat. No. 4,190,705 utilizes iron complexes to suppress the reverse reaction. The iron complexes serve mainly to suppress this reaction and, although they result in an increase in power output due to the suppression of the reverse reaction, the total output still remains quite low in this device. It is believed that the complexes formed in the '705 patent are not very efficient due to poor complex formation.

Accordingly, a need exists in the art to provide a more efficient solar cell which avoids the deficiencies noted above with respect to U.S. Pat. No. 4,190,705.

SUMMARY OF THE INVENTION

In the present invention it has been discovered that certain specific metal complexes, especially certain novel iron complexes, can be used in a new type of photogalvanic cell which results in improvements and advantages over the cells described in U.S. Pat. No. 4,190,705. The particular complexes used in the present invention results in the cells' ability to not only produce electric current in the presence of light, but it also results in the cells having the ability to function as a battery by storing electric power and retaining it at night when the cells are not exposed to sunlight. In addition, the cells of the present invention do not require a special dye such as thionine nor do they require that one of the half cells be kept in the dark.

The cells of the present invention achieve a high level of electric output due to the particular type of metal carboxyl complexes and organometallic complexes used in the solutions thereof. Although U.S. Pat. No. 4,190,705 utilizes organic metallic complexes, it will be readily appreciated that the complexes selected for use in the present invention are selected for a totally unrelated purpose than the complexes used in the '705 patent. The complexes of the '705 patent are selected to suppress a reaction between the higher valence state redox couple and the dye in the reduced state. Thus, the complex formed in the '705 patent inhibits the $Fe^{+3}$ ion from receiving an electron from the $Th^-$ anion. For this reason, the '705 patent adds agents which form a complex with the higher valence ions of the metal couples in the solution. The present invention utilizes novel metal complexes which are capable of responding to light in a manner which generates a higher amount of electric current as the complexes give up and receive electrons in the particular type of cells used in the invention. The complexes used in the present invention are unlike those use in the '705 patent and they achieve a high level of power output without the necessity of using thionine or any other type of dye. In addition, the solar cells of the present invention have the ability to generate a high output of electric current without the necessity of one electrode being kept in the dark while the other electrode is exposed to light. This is a significant advantage over the device described in U.S. Pat. No. 4,190,705.

Furthermore, the establishment of the electric current from one electrode to the other, even when both electrodes are exposed to light, is aided by the selection of particular pairs of electrodes. This selection of electrodes is absent from U.S. Pat. No. 4,190,705 since it is stated in the '705 patent that the exact nature of the electrodes is not critical.

It is an object of the present invention to provide a solar cell which does not require one of the electrodes to be kept in the dark while the other electrode is exposed to light.

It is also an object to provide a solar cell which does not use thionine or a similar light sensitive dye.

It is also an object to provide new metal complexes, especially specific iron acetate and iron citrate complexes, which have enhanced potential for generating electricity in the cells of this invention.

It is also an object to provide a method for making the metal complexes used in this invention.

These and other objects will become apparent to those skilled in the art.

BRIEF DESCRIPTION OF THE DRAWINGS

FIG. 11 is an illustration of the basic cell of this invention used to gather experimental data.

FIG. 12 is a perspective view of a preferred embodiment of the cell.

FIGS. 17A1 ∝ 17D show the absorbance of chemically treated complexes obtained from the seven best cells described in data table 6.

DETAILED DESCRIPTION OF THE INVENTION

Figure 1:
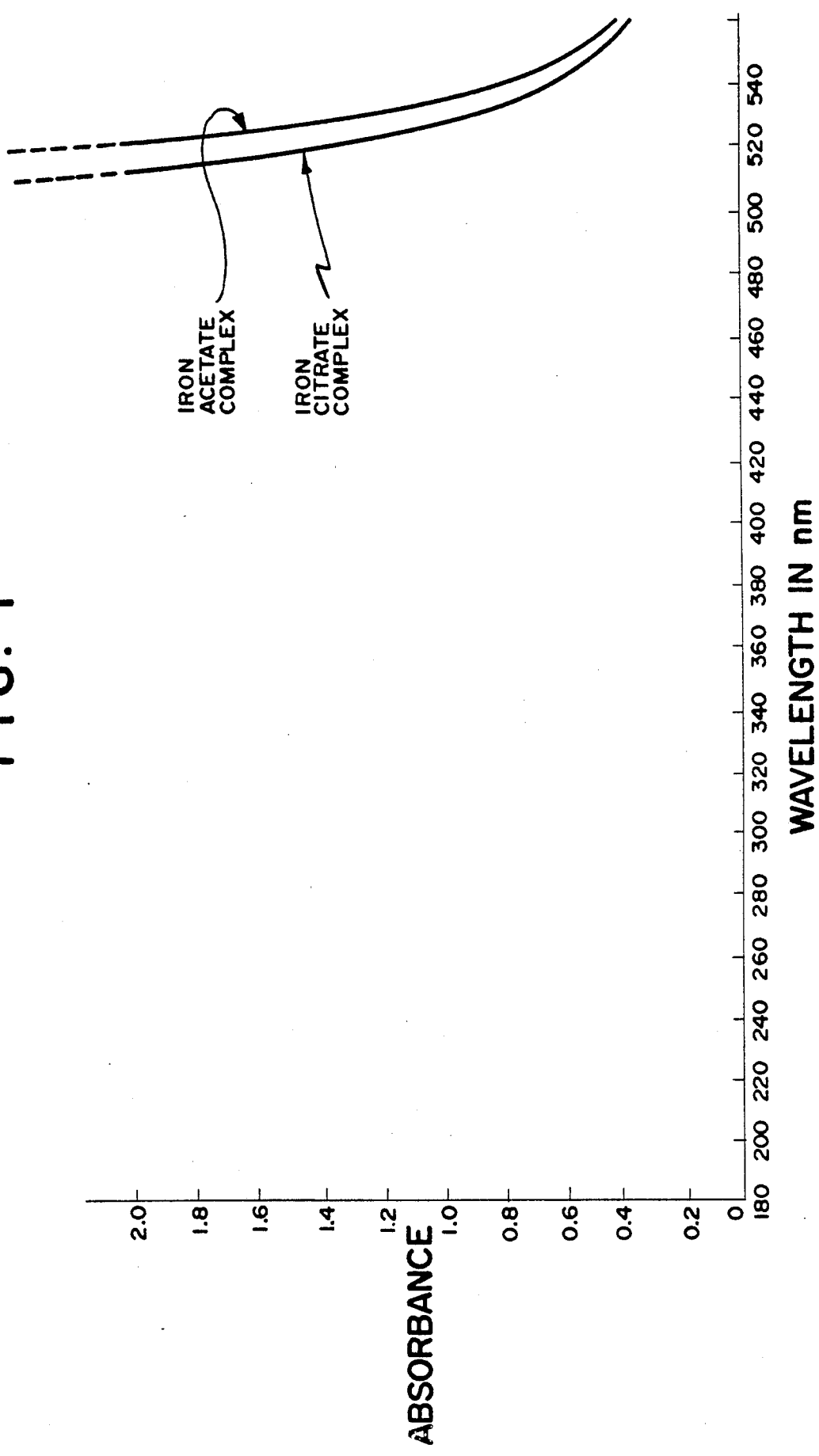
FIG. 1 is a graph which shows the u.v.-visible spectroscopy scan of approximately 1M iron citrate complex and a 1M iron acetate complex.

The solar voltaic storage cell or rechargeable battery of this invention, comprises at least one photoelectrochemical solar voltaic storage cell. The storage cells include a pair of electrodes in contact with a photochemical solution. The photochemical solution is contained in a suitable vessel capable of allowing light into the solution so that the photochemical solution will release electrons upon exposure to light. The released electrons will be carried in the solution to one of the electrodes. The pair of electrodes may be connected by electrical connecting means, such as wires, to define a circuit so that the released electrons can pass from the anode to the cathode and thereby result in usable electric current.

The electrodes of each pair are chosen so that one electrode, i.e., the anode, has a greater ability to receive an electron which has been released from the metal complex. The cathode must be chosen which has a relatively lesser ability to receive the electron. By choosing the electrode pairs in this manner, the electrons will flow through the circuit from the anode to the cathode.

The transfer of the electron from the complex to the electrode is believed to be associated with the reversible breakdown of water which forms $OH^-$ ions and the release of a hydrogen-free radical. Maintaining the complex in an acidic medium with the use of a buffer, assures that the metal complex and electron transfer mechanism continues to function for an extended period of time. If the pH of the solution containing the complex rises to more than about 4, some of the iron precipitates as a red precipitate due to the destruction of the metal complex. For that reason, it is preferable to keep the pH less than 4. However, it is believed that after a period of time, the sunlight acts on the complexes in an operating cell to produce an organometallic complex which is more stable and does not require an acidic environment.

As long as the photochemical solution is exposed to light, the cell will release electrons from the metal of the metal complex. The light must contain photons of sufficient energy to free the electrons. The released electrons will remain available in the solution as stored potential electrical energy which can be used at any time even when the cells are in darkness.

By choosing the electrode pairs as indicated above, it is possible to produce and store electrical energy in a cell wherein both electrodes are contained in the same chamber without the need to separate the anode and cathode by a barrier. Also, as a result of the particular metal complexes used in this invention and the selected electrode pairs, it is not necessary for one electrode to remain in the dark. Thus, they may both be kept in the light, both in the dark, or one in the light and one in the dark. It is only necessary for the photochemical solution to be exposed to light, particularly sunlight.

The cell is made from any suitable durable material capable of holding the photochemical solution and which allows the passage of light therethrough which is necessary to produce the electricity. Thus, at least a portion of the material will have to be transparent to that portion of the light spectrum which is absorbed by the metal complex. For that reason, polyethylene or $SiO_2$ or quartz containers are preferable when the metal complex is the preferred acetochloroamine ferrate or citratochloroamine ferrate. Other materials are useful when iron acetate or iron citrate complexes are used so long as they allow the visible and u.v. light to pass therethrough. These materials are also suitable for use with other metal complexes described herein.

Suitable electrode pairs are as follows: platinum-gold; silver-gold; platinum-silver; lead-lead carbide; lead-gold; lead-silver; lead-platinum; lead-silver carbide; platinum-lead carbide; platinum-silver carbide; silver-silver carbide; silver-lead carbide; gold-lead carbide; gold-silver carbide; silver carbide-lead carbide; copper-lead carbide; copper-silver carbide; copper lead alloy-lead carbide; copper lead alloy-silver carbide; tin lead alloy-platinum; tin lead alloy-gold; tin lead alloy-silver carbide; tin lead alloy-lead carbide; and tin lead alloy-silver.

The lead carbide and silver carbide electrodes may be made by adsorbing the silver or lead onto activated carbon and then taking up an equal mass of paraffin wax as a binder.

More particularly, the lead carbide electrode may be made by mixing 10% lead with 90% activated carbon powder and heating the mixture in a closed beaker over a Bunsen burner at about 1000° C. The heat is applied for a few hours. It is believed that the lead absorbs the carbon to form PbC which is a black powder. The electrode is formed by mixing the PbC with a sufficient amount of paraffin binder so that the electrode can be molded and the power production remains high. Mixing the PbC with about an equal mass of paraffin binder is adequate since this mixture can be easily molded while still having adequate power production. The PbC and wax mixture can be molded into any desirable shape.

The silver carbide electrode may be made by pouring 0.1M silver nitrate upon activated carbon powder in amounts which yield 10% silver and 90% carbon. Proper equivalents of dilute HCl acid are added and the mixture is stirred and then filtered to eliminate nitrate ion and water. All of this is done in the presence of light. The black residue from the filter is spread around and exposed to sunlight for a few weeks. It is believed that the silver ion is converted to free silver and, because it is contact with the activated carbon, it absorbs the carbon instead of being reduced to the usual free silver. The silver carbide powder is formed into an electrode with paraffin wax binder by the same process used to form the lead carbide electrode.

The electrodes are preferably sized so that they have sufficient surface area to produce power in dilute solutions but are not so large that their power production becomes disproportionate to their size. About 0.5 inch of 1/16 inch thick lead and about 1.5 square inch surface area of the silver carbide appear to be the most suitable for thin electrode pair systems.

The copper lead alloy is preferably formed from an alloy having 20% copper and 80% lead, by weight. When a lead anode is used, it should be poisoned with sulfate by treating the anode with a solution of $H_2SO_4$. This treatment may be accomplished by treating the lead anode with 1 N sulfuric acid.

FIG. 11 illustrates a basic type of cell. In the embodiment shown in FIG. 11, a tube 1 made of quartz, polyethylene or similar material is filled with a metal complex of this invention (buffered or unbuffered) indicated by reference numeral 2, up to the level indicated by numeral 3. A pair of electrodes indicated by numerals 4 and 4a are immersed into the solution. The electrodes may have electrical connecting means so that the power generated and stored within the cell can be connected to an electrical circuit to perform useful work. Suitable electrical connecting means are shown in FIG. 11 by the wires indicated by numerals 5 and 6. A covering 7 may be provided to prevent evaporation of the solution. An opening 8 may be included on the cover so that liquid can be added or removed from the cell. A plug 9 may be used to seal the opening. Preferably, the plug is porous to prevent accumulation of gas within the cell.

In a preferred embodiment, the electrodes are arranged in the cell in a manner which maximizes their surface area within the confined space of the container and which also allows the passage of sufficient light into the volume of the solution. This embodiment is illustrated in FIG. 12. The embodiment shown in FIG. 12 has a pair of spaced apart interdigitated electrode plates 10 and 11. In this arrangement, a large surface anode 10 and a corresponding cathode 11 are attached to a bottom plastic plate 12 shown by the broken lines. The electrode and plate assembly is contained in container 14 which is made of suitable light transmissive material such as polyethylene or quartz. Plate 12 may be an integral part of the bottom portion of container 14.

Container 14 may be covered on the top with a fine sieve comprised of fine plastic strand meshing which allows sunlight to enter, $CO_2$ to escape, and water vapor to pass into and out of the cell. The electrodes may be raised as shown in FIG. 12 or may be flat on the bottom surface. Cells of this type which are covered with mesh allow the solution to evaporate to form a deliquescent complex. A deliquescent complex is formed by adding 1M buffered complex solution to the cell, placing the sieve on the top and allowing the solution to evaporate while the cell is exposed to sunlight. This forms a hydrated solid and once it is hydrated, the buffered complex absorbs water vapor from the atmosphere, i.e., it is deliquescent. The deliquescent hydrated solid is also active in producing electric power in the cells of this invention.

Instead of covering container 14 with a fine mesh, the container may be sealed with the exception of a small opening and plug located on top, such as the opening 15 and plug 16 shown in FIG. 12. Preferably, plug 16 is porous.

The electrodes of the embodiment shown in FIG. 12 as well as the other embodiments, are adapted for electrical connection to the outside of a cell so that the electrical power generated in the cell can be electrically connected by electrical conducting material, such as copper wire, to form an electric circuit. The electrodes may be connected to terminals so that wires can be easily attached thereto or the wires may be directly attached to the electrodes. The wires from the electrodes from a plurality of cells may be connected in series or parallel to suit the particular electrical needs for which the cells are being utilized.

In those embodiments where a portion of the electrodes is not immersed in the solution, such as the embodiment shown in FIG. 11, the wires may be directly connected to the electrodes.

Care should be taken to prevent the wire from coming into contact with the solution in the cell. This is particularly important in those instances where copper wire is connected to the cathode, since the copper wire will easily corrode if it comes into contact with the solution at the cathode. Thus, the copper wire connected to the cathode should be shielded from the solution. The shielding may be accomplished by providing a layer of lead or tin lead alloy on the cathode material at the location where the wire is connected. The copper wire is then connected to the lead or lead alloy. The lead or tin lead layer can be shaped to assure that the copper wire is connected to the lead or tin lead alloy at a location where it is not in contact with the solution. A useful and readily available tin lead alloy for this purpose is an alloy containing 60% tin and 40% lead. Preferably, the copper is shielded from the solution at both the cathode and the anode.

In those embodiments where the electrodes are completely immersed in the solution, such as the one shown in FIG. 12, as well as in other embodiments where the electrical connections are made below the surface of the solution, the electrodes may be sealed to the bottom of the cell in a watertight manner so that the electrical connections can be made to the electrodes through the bottom of the container without coming into contact with the solution. In addition, a layer of lead or tin lead alloy may be used to further assure that the wire will not come in contact with the solution.

Figure 12A:
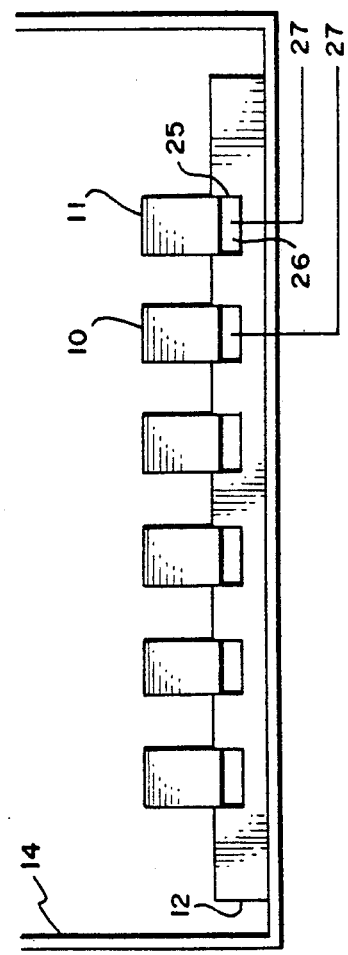
FIG. 12A is a cross sectional view along line AA of FIG. 12.

FIG. 12A illustrates the electrical connection which may be used to connect the copper wire in an embodiment such as that shown in FIG. 12 where the electrical connections are made below the surface of the solution. FIG. 12A is a cross section along line AA' of FIG. 12. The interdigitated portions of electrodes 10 and 11 are shown sealed in grooves 25. Preferably, the seals are watertight. Each groove is partially filled with lead or tin lead alloy 26. The lead or lead alloy should be sealed to the groove to make a watertight connection. The electrodes make contact with the lead or lead alloy in the grooves in which the electrodes are seated. The copper wires 27 for each electrode are connected to the lead or lead alloy contained within the grooves.

Since the electrodes have a watertight seal in the grooves, there is little likelihood that the solution will make contact with the lead in the grooves.

It is particularly important that the lead used to make the cathode connection, not come in contact with the solution, especially when a lead anode is being utilized. If the lead connection used in the cathode were to come in contact with the solution in a cell which utilizes a lead anode, then, in effect, there would be two anodes and no cathode.

It is important that the pairs of electrodes be chosen as described herein so that one electrode acts as an anode and the other acts as a cathode. Thus, extraneous metals should not come in contact with the electrode and the solution if that metal is inconsistent with the metal pairs described herein. Thus, an anode metal, such as lead, should not be used in contact with the cathode and the solution.

It has been observed that lead has a deleterious effect on the buffer used in the solution. For this reason, any lead which is exposed to the solution is preferably poisoned with sulfate before the solution is placed in the cell.

In another embodiment, a plurality of anodes and cathodes are situated in one container which is connected by conduits or pipes to a remote solar tank. The container, pipes, or conduits and solar tank constitute a system which is filled with a metal complex containing solution. Means, such as a pump, is provided for circulating the solution through the system. This type of embodiment is schematically represented in FIG. 13.

Figure 13:
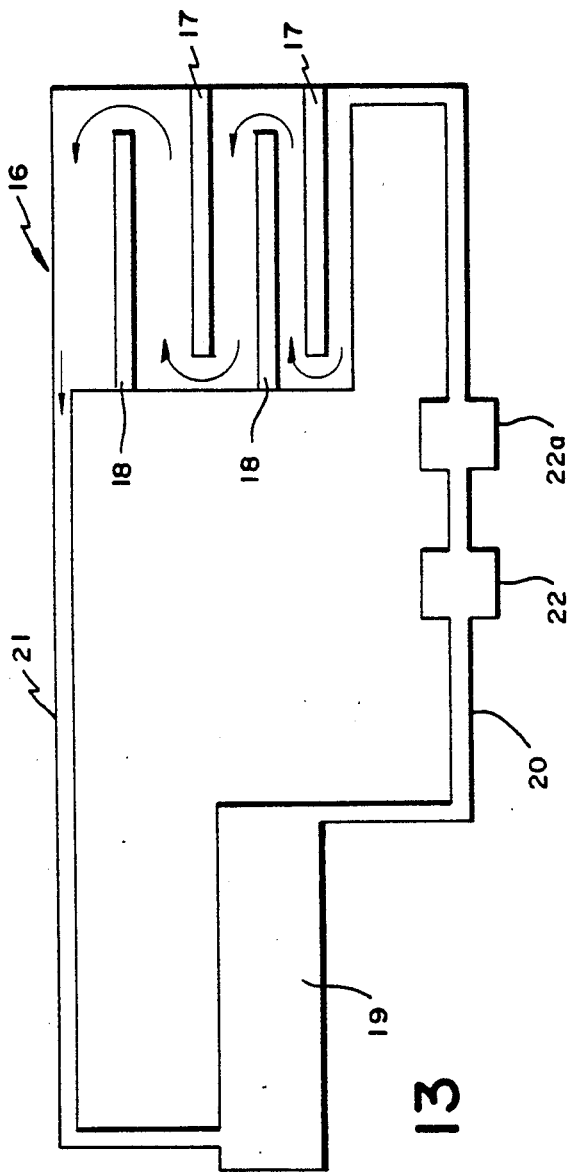
FIG. 13 is a schematic representation of another preferred embodiment of the solar cell.

FIG. 13 shows a system having a container 16 which houses the cathodes 17 and the anodes 18. A conduit such as pipe 20 is used to connect the container 16 to the remote solar tank 19. A second pipe 21 also connects the solar tank to the container so that the solution can circulate through the container to the tank and then back again to the container. A pump 22 may be placed at any convenient location so that the metal complex solution contained within the system can be circulated from the solar tank to the container and then through the container and back to the solar tank in a continuous fashion as illustrated in FIG. 13.

FIG. 13 shows the system having a container 16 which houses the cathodes 17 and the anodes 18. A conduit such as pipe 20 is used to connect the container 16 to the remote solar tank 19. A second pipe 21 also connects the solar tank to the container so that the solution can circulate through the container to the tank and then back to the container. A pump 22 may be placed at any convenient location so that the metal complex solution contained within the system can be circulated from the solar tank to the container and then through the container and back to the solar tank in a continuous fashion.

The electrodes 17 and 18 are preferably spatially arranged within the container 16 so that solution entering the container via pipe 20, flows past the electrodes in a tortuous path as indicated by the arrows. Pipe 21 is connected to the container at a location to receive the solution after it has made its tortuous circulation past the electrodes within the container.

An advantage of using this system described in FIG. 13 is that the container may be located in one area, for instance indoors in a heated environment, and the solar tank can be kept outdoors where it is exposed to sunlight. By having the electrodes in a separate container remote from the solar tank, it is not necessary that the container be made of light transmissive materials. In such an arrangement, only the solar tank needs to be transparent to light. The solar tank is constructed of nonreactive material. The tank may be open with a polyethylene canopy. An open tank should have means of adding pure water to offset loss due to evaporation. In addition, the shape of the container housing the electrodes and the arrangement of the electrodes contained therein may be chosen to maximize the surface area of the electrodes without placing any limitations on the electrode arrangement which would be necessary if exposure to light were an important factor. Also, the absence of electrodes in the solar tank means that the tank may be designed to maximize the transmission of light into the solution without interference from the electrodes.

It will also be apparent that the embodiment shown in FIG. 13 containing a separate solar tank, will absorb heat from the sunlight in addition to converting the metal complex to a more oxidized valent state. Thus, the system of this embodiment can be used to collect heat as well as generate and store electric power. The heat of the system could be recovered by connecting conventional heat exchanging means to the system. Such a system having the ability to produce heat and electricity from sunlight would result in a significantly more efficient liquid solar heating unit than the types currently used. A convenentional heat exchanger 22a is shown in FIG. 13.

The electrodes in container 16 are connected to a conventional electric circuit by electric connecting means such as copper wire. In this embodiment as in the others, any elements such as the copper wire, which could be corroded by the solution, should be protected from the solution by shielding material or waterproof insulation.

The electrodes 17 and 18 may be connected in series or parallel as desired and be connected to an external conducting wire such copper wire. The electricity produced by this embodiment may be used to perform useful work such as producing light or heat or operating electric appliances. It may also be stored in a secondary storage system such as one which uses batteries.

Figure 14:
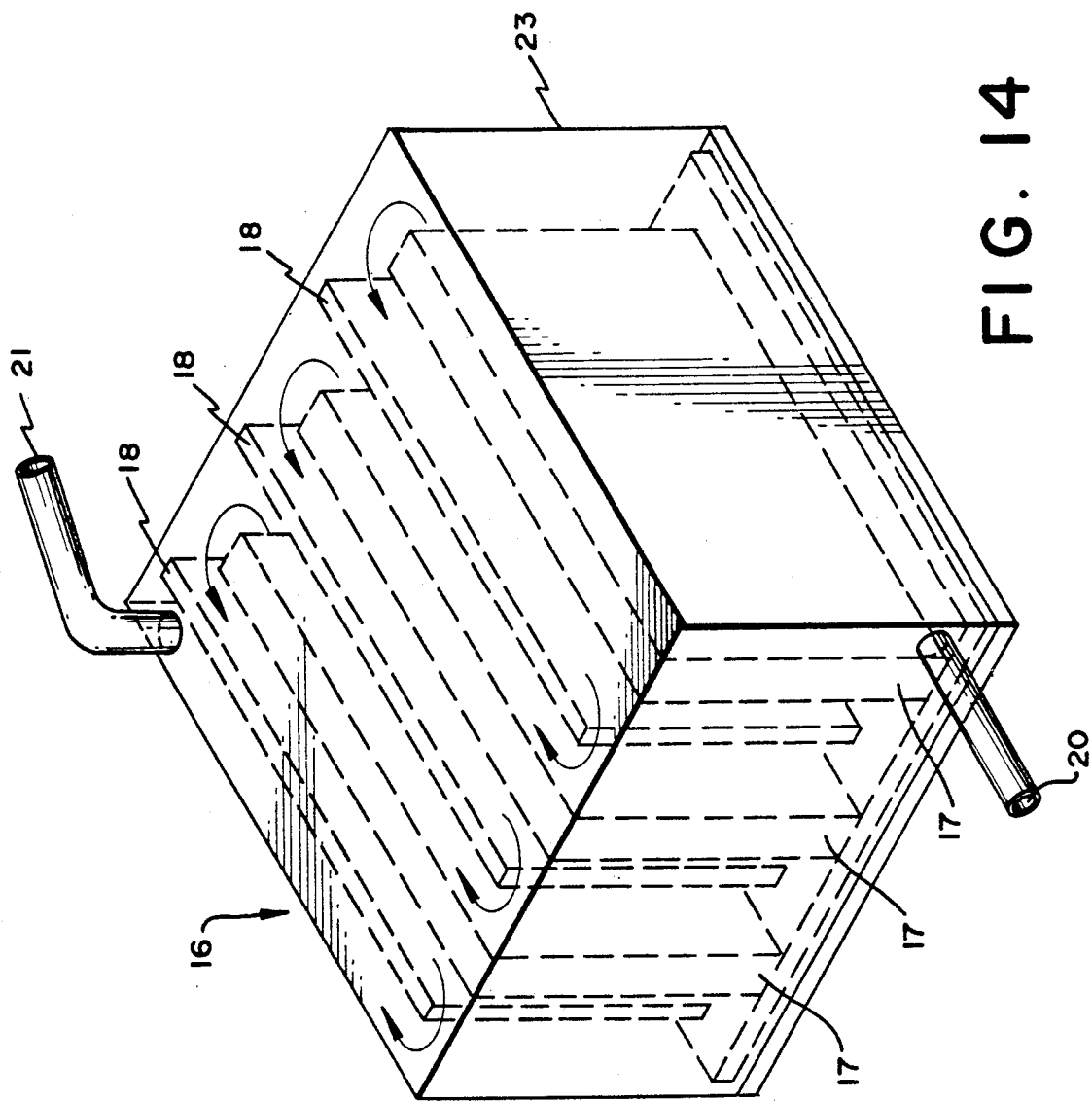
FIG. 14 is a perspective view of another preferred embodiment of the solar cell.

The container 16 is shown with greater detail in FIG. 14. In FIG. 14, the electrodes 17 and 18 are in the form of plates. The anodes 18 alternate with the cathodes 17. The alternating anodes and cathodes are set in grooves in a plastic case 23 on three sides, i.e., the top, the bottom and one side.

A space is left free between one side of each electrode and the case. The side at which the free space is located alternates for each electrode so that one side of each anode has a free space between it and the case; and the opposite side of each cathode has a similar space between it and the case. This arrangement, as illustrated in FIG. 14, results in alternating spaces being formed between successive electrodes so that the solution entering at pipe 20 flows through the case past each electrode in a tortuous path as shown by the arrows in FIG. 14. After traversing the sequence of electrodes, the solution exits at pipe 21 and passes to the solar tank where incoming light regenerates the solution. Pipes 20 and 21 are connected to the solar tank.

FIG. 14 shows pipe 21 connected to the top of the container. It is preferable to connect pipe 21 at the top so that any gas which forms in the container 17 may be eliminated from the container. One or more gas vents may be included in the system to eliminate this gas.

A suitable electrode pair for the embodiment shown in FIGS. 13 and 14 is a copper lead alloy (20% copper and 80% lead, by weight,) for the anode and lead carbide in activated carbon with a paraffin binder, as the cathode.

The complexes used in the cells of this invention are complexes of various metals which are formed by attaching certain atoms or molecules (i.e., ligands) to bonding sites within the coordination sphere of the metal ion. The ligands and metal ions are selected so that the complex is capable of yielding an electron upon exposure to light. The metals which are useful must form a complex which is capable of yielding an electron upon exposure to light. Suitable metals include iron, magnesium, cobalt, nickel, aluminum, calcium, manganese, chromium, copper, zinc and tin. Other metals which can form complexes according to the process described herein, are also useful but not all metals are desirable because of other factors such as toxicity or expense. All that is required is for the metal to have the capability of existing in two valent states and be able to form a complex as described herein.

The metal complexes are formed by attaching the complexing agents to the metal ion so that the complexing agents are attached to the bonding sites in the coordination sphere of the metal. In the case of iron, it is believed that the iron forms a complex by the attachment of six atoms or molecules to the bonding sites of the iron ion.

When exposed to sunlight, the metal complexes at the anode are capable of yielding an electron when a photon of sufficient energy is absorbed. The complex is converted to a less reduced or oxidized state $(M^{+2} \rightarrow M_{+3} + e^-)$ as it gives up an electron. This free electron travels through the external circuit from the anode to the cathode where an equivalent valent state complex molecule picks up the electron and the complex is converted to a more reduced state $(e^- + M^{+3} \rightarrow M^{+2})$.

The coordination configurations of the metal ions are: octahedral inner filling $d^2sp^2$ for iron, manganese, cobalt, chromium, and nickel and octahedral outer filler $sp^3d^2$, for aluminum and zinc. Copper is planar inner filling $dsp^2$, It would be expected that the octahedral nickel would dominate over the planar nickel because of the good power and stability of the nickel acetate complex. Another argument could be made for the planar configuration of nickel because of the much less effective nickel citrate complex. This could be suggesting that when the citrate ion chelates the square planar nickel, there is not enough strong bonds remaining for the $NH_3$ and $Cl^-$ ligands. Apparently, the affinity of the water molecule to the coordination sphere of the metal is not as great for which it can cause its rapid destruction. The latter argument could be supported by the low power of the planar copper complexes. The two very weakly bonded ligands which are perpendicular to the four ligand plane must not contribute effectively to the functioning of the complex. Here again, the citrate is the lower power complex. Data table 6 illustrates the power of the complexes in which each cell's electrodes remain shorted and the cells are kept outside twenty-four hours a day. Data table 1 illustrates the laboratory analysis of the complexes.

With reference to the data contained in Table 1 it will be observed that the laboratory analysis of the nickel acetate complex demonstrates that it contains the acetate, chloride and the ammonia molecule. The laboratory analysis of the nickel citrate demonstrates the presence of citrate, chloride and the absence of the ammonia. Both planar copper complexes show the carboxyl ions, chloride ion and the absence of the ammonia molecule in both complexes. This could be interpreted as indicating that the carboxyl ions and the chloride ions both bond to the metal ion in a plane and the ammonia molecule bonds to the metal ion at the bond site which is perpendicular to the plane. When the complex is a square planar complex, the metal-ligand strong bonds are in the plane and the very weak bonds are where the $NH^3$ bonds are easily cleaved. Using these four complexes as a model, then a hypothesis can be suggested for the magnesium and calcium complexes. The data suggests that both magnesium complexes are octahedral. The data suggests that the calcium citrate is probably square planar, but the calcium acetate complex could possibly contain some octahedral characteristics because of the ammonium odor in the analysis. The absence of the ammonia in data Table 1 from both of the aluminum complexes could be due to the fact that the aluminum complexes are much more dilute than the other complexes except the chromium complexes. It would be difficult to conclude that the absence of the ammonia of the chromium citrate complex would be due to the dilute nature of the complex or that it is a planar configuration. Both tin complexes are apparently some other type of configuration in which the metal-ligands are not strong enough to withstand the harsh 6M NaOH treatment but strong enough to be very effective solar complexes as described in data table 6.

The bond sites for the octahedral configuration would be as described below in formula I for iron. The bonds sites of the planar configuration would be as described below in formula II for copper. The —bonds above and below the central metal ion in the planar configuration are the very weak bonds that were suggested.

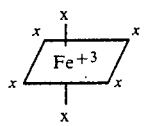

Formula I

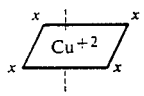

Formula II

Each x in the above formulae represents one of the ligands attached to the Fe or Cu ion in the coordination sphere.

Although many different metals are suitable for forming the complexes of the solution, it is necessary for the complexes to contain ammonia, chloride, and carboxyl or the particular carboxyl derivatives described in this specification. The preferred carboxyl ligands are obtained from acetic or citric acid.

The complexes of this invention can exist in two different valent states with the less reduced valent state being formed upon exposure to light whereby an electron is released from the complex. The ability to exist in two valent states is believed to be due to the change of valence of the metal ion in the complex upon exposure to light. This is illustrated as follows with respect to iron: $Fe^{+2} \rightarrow Fe^{+3} + e^-$.

In a preferred embodiment an iron citrate or an iron acetate complex is used. The citrate complex is citratochloroamine ferrate II and III and the acetate complex is acetatochloroamine ferrate II and III. The Roman numerals indicate the two different valent states which are possible with each complex with numeral III indicating the $Fe^{+3}$ state and II indicating the $Fe^{+2}$ state.

The term citratochloroamine ferrate indicates a complex containing at least one chloride ligand, at least one ammonia ligand and at least one citrate ligand. The citrate ligand is formed as an ionic linkage between a carboxyl anion of citric acid or its salt and the metal cation. Since there are three carboxyl groups in citric acid, it is possible that the citrate ligand may have more than one bond connecting it to the metal. Thus, up to three bonding sites may be utilized in bonding the metal to the citrate ligand. The same is the case with the other ten metal citrate complexes.

The term acetochloroamine ferrate indicates a metal complex containing at least one acetate ligand, at least one ammonium ligand and at least one chloride ligand. The acetate ligand is formed as an ionic linkage between the carboxyl ion of the acetic acid or its salt, and the metal cation. The same is the case with the other ten metal acetate complexes.

The iron acetate complexes used in this invention are formed by reacting $FeCl_3$ with NaOH in an aqueous solution to form an intermediate product which is then reacted with ammonium acetate to form a red precipitate. The solution are then filtered and an acetic acid solution is added to the red precipitate. Finally, HCl and sodium acetate are added. The solution contains the iron complex to which the ligands (acetate, $NH_3$, and $Cl^-$) are attached to the six-bond sites.

The preferred iron acetate complex is formed as follows:

1. 1,040 ml of aqueous $FeCl_3$ (1 M) is mixed with 124.8 g solid NaOH. After the reaction is over, the solution is allowed to stand for fifteen minutes.
2. 144 g of ammonium acetate is then added to the solution while stirring.
3. The solution is then filtered to remove a red precipitate.
4. The red precipitate is recovered and added to 80 ml of concentrated acetic acid while stirring. The solution is allowed to stand for five minutes.
5. 350 ml of concentrated hydrochloric acid is then added to the solution while stirring until it is clear, in about fifteen minutes.
6. 33 g of sodium acetate (either in the hydrated or anhydrous form) are then added to the solution while stirring. This yields about 1100 ml of iron acetate complex.

The iron citrate complexes used in this invention are formed by dissolving green ferric ammonium citrate and citric acid in water and then adding hydrochloric acid to form a clear amber solution containing the iron citrate complex.

The preferred iron citrate complex is formed as follows:

1. 326.136 g of green ferric ammonium citrate plus 70.64 g of citric acid plus 620 ml of distilled water are mixed together while heating gently until the compounds go into solution.
2. 381.8 ml of concentrated hydrochloric acid are then stirred into the solution until the solution is a clear amber color.

The complexes formed by the above preferred methods are believed to contain the iron ion in either the $Fe^{+2}$ or $Fe^{+3}$ state having six ligands attached thereto in the coordination sphere. The ligands for the acetate complex are acetate, $NH_3$ and $Cl^-$. The ligands for the citrate complex are citrate, $NH_3$ and $Cl^-$.

The iron citrate can be prepared by starting with a hydrated iron III chloride prepared as a one molar solution. Solid NaOH is added to the solution in sufficient quantity to tie up three of the six iron hybridized bond sites of the weak field coordination sphere with $OH^-$ ligands. The solution is stirred until the reaction is complete and is then left to stand for about fifteen minutes. 1.5 moles of ammonium citrate are then stirred into the solution to form a precipitate which is then separated from the solution by filtering. To the precipitate, 1.3 equivalents of citric acid are added. A period of about five minutes is allowed for digestion. Afterwards, concentrated hydrochloric acid is added to the residue with stirring until the solution becomes clear. Next, 0.25 moles of sodium citrate is dissolved into the clear solution.

The acetate and citrate complexes of the remaining ten metals are formed by the following procedures:

Synthesis of the chromium acetate complex

1. Dissolve 19.37 g of $Cr(NO_3)_3.9H_2O$ in water and add 10.6 g of solid NaOH while stirring. Allow fifteen minutes of digestion time.
2. Add 20.837 g of ammonium acetate while stirring.
3. Filter to collect the precipitate and remove the nitrate ion, which remains in the filtered solution and is discarded.
4. 3.8 ml of glacial acetic acid is added to the precipitate while stirring. Let set fifteen minutes.
5. 27.8 ml of concentrated hydrochloric acid is added. Stir and add pure water until it goes into a clear solution.
6. 0.96 g of anhydrous sodium acetate is added. Stir until the salt goes into solution. Final volume is 169 ml.

Synthesis of the chromium citrate complex

1. Dissolve 20.5 g of Cr(NO$_3$)$_3$.9H$_2$O in pure water and add 6.147 g of solid NaOH while stirring. Allow fifteen minutes to digest.
2. 12.46 g of ammonium citrate is added while stirring. This salt was prepared adding solid NH$_4$OH to citric acid.
3. Filter to collect the precipitate and remove the nitrate ion, which remains in the filtered solution and is discarded.
4. 1.482 g of citric acid is added to the precipitate while stirring. Allow fifteen minutes for digestion.
5. 37.3 ml of concentrated hydrochloric acid is added plus about 25 ml of pure water, with stirring until it goes into solution.
6. 0.355 g of anhydrous sodium citrate is added. Stir until the salt is dissolved. Final volume is 141 ml.

Synthesis of the manganese acetate complex 1. 22.41 g of MnSO$_4$.H$_2$O is dissolved in pure water. Add 10.61 gram of solid NaOH, while stirring. Allow fifteen minutes for digestion.
2. 20.44 g of ammonium acetate is added while stirring.
3. Filter to collect the precipitate and eliminate the sulfate ion.
4. Add 7.1 ml of glacial acetic acid to the precipitate while stirring. Allow this to digest for fifteen minutes.
5. 61 ml of concentrated hydrochloric acid is added while stirring to dissolve the residue. Add pure water, while stirring, until the solid goes into a clear solution.
6. 1.75 g of anhydrous sodium acetate is added, while stirring, until it goes into solution. Final volume is 244 ml.

Synthesis of manganese citrate complex 1. 27.17 g of MnCl$_2$.4H$_2$O is dissolved in pure water. Add 11 g of solid NaOH while stirring. Allow fifteen minutes for digestion.
2. Add 22.26 g of ammonium citrate while stirring. This was prepared by adding 18.3 ml to NH$_4$OH to 17.584 g of citric acid.
3. Filter to collect the precipitate.
4. 2.658 g of citric acid is stirred into the residue. Allow fifteen minutes to digest.
5. 52 ml of concentrated hydrochloric acid is added while stirring. Add pure water while stirring until the solution is clear.
6. 0.638 g of anhydrous sodium citrate is added while stirring until it is dissolved. Final volume is 278 ml.

Synthesis of the nickel acetate complex 1. 54.05 g of NiCl$_2$.6H$_2$O is dissolved in pure water. Add 18.19 g of solid NaOH while stirring. Allow the residue to digest for fifteen minutes.
2. 35.05 g of ammonium acetate is added to the residue while stirring.
3. Filter to collect the precipitate.
4. 12.1 ml of glacial acetic acid is stirred into the residue. Allow fifteen minutes for digestion.
5. 53 ml of concentrated hydrochloric acid is added and the mixture is stirred until it goes into a clear solution.
6. 3 g of anhydrous sodium acetate is added and stirred until it goes into solution. Final volume is 250 ml.

Synthesis of nickel citrate complex 1. 52.2 g of NiCl$_2$.6H$_2$O is dissolved in pure water. 18.58 of solid NaOH is added with stirring. Allow fifteen minutes of digestion time.
2. 31 ml of concentrated NH$_4$OH is added to 29.75 g of citric acid to prepare ammonium citrate. This is added while stirring to the residue until it is well mixed.
3. Filter to collect the precipitate.
4. 4.5 g of citric acid is added to the residue while stirring. Allow fifteen minutes for digestion.
5. 54.2 ml of conentrated hydrochloric acid is added, while stirring, until it goes into a clear solution.
6. 1.1 g of sodium citrate is added while stirring until it goes into solution. Final volume is 352 ml.

Synthesis of aluminum acetate complex 1. 62.65 of Al(NO$_3$)$_3$.9H$_2$O is dissolved in water. 20.04 g of solid NaOH is added, while stirring. Allow fifteen minutes for digestion. The reaction is very exothermic.
2. 38.62 g of ammonium acetate is stirred into the mixture.
3. Filter to collect the precipitate and eliminate the nitrate ion.
4. 13.4 ml of glacial acetic acid is stirred into the residue.
5. 148.5 ml of concentrated hydrochloric acid is added to dissolve the residue while stirring. Add pure water while stirring, until a clear solution exists.
6. 3.3 g of anhydrous sodium citrate is added to the clear solution while stirring, until the salt is dissolved. Final volume is 585 ml.

Synthesis of aluminum citrate complex 1. 78.57 g Al(NO$_3$)$_3$.9H$_2$O is dissolved in pure water. 25.136 g of NaOH is stirred into the residue. Allow fifteen minutes for digestion. The reaction is very exothermic.
2. 41.9 ml of concentrated NH$_4$OH to 40.24 g of citric acid while stirring. The ammonium citrate solution is mixed with the residue while stirring.
3. Filter to collect the residue and eliminate the nitrate ion.
4. 6.082 g of citric acid is added while stirring. Allow fifteen minutes for digestion.
5. 168.3 ml of concentrated hydrochloric acid is added to the residue while stirring. Add pure water while stirring until the solution becomes clear.
6. 1.49 g of anhydrous sodium citrate is added while stirring, until it goes into solution. Final volume is 550 ml.

Synthesis of copper acetate complex 1. 63.64 g CuSO$_4$.5H$_2$O is dissolved in pure water. 20.40 g of solid NaOH is added while stirring. Allow fifteen minutes for digestion.
2. 39.293 g of ammonium acetate is added to the residue while stirring.
3. Filter to collect the residue and eliminate the sulfate ion.
4. 13.6 ml of glacial acetic acid is added to the residue while stirring. Allow fifteen minutes for digestion.
5. 87.5 ml of concentrated hydrochloric acid is added to the residue while stirring. Add water while stirring, until the solution becomes clear.

6. 3.364 g anhydrous sodium acetate is added while stirring, until it goes into solution. Final volume is 547 ml.

Synthesis of copper citrate complex 1. 64.22 g of $CuSO_4.5H_2O$ is dissolved in pure water. Add 20.577 g of solid NaOH while stirring. Allow fifteen minutes for digestion.
2. Prepare ammonium citrate by mixing 34.3 ml of concentrated $NH_4OH$ with 32.95 g of citric acid. Stir this solution into the residue.
3. Filter to collect the residue and eliminate the sulfate ion.
4. 4.981 g of citric acid is stirred into the residue. Allow fifteen minutes for digestion.
5. 60 ml of concentrated hydrochloric acid is poured into the residue while stirring. Stir until it becomes a clear solution. Volume is 488 ml.

Synthesis of cobalt acetate complex 1. 51.1 g of $CoCl_2.6H_2O$ is dissolved in pure water. 17.182 g of solid NaOH is added to the residue while stirring. Allow fifteen minutes for digestion.
2. 33.109 g of ammonium acetate is added to the residue while stirring.
3. Filter to collect the residue.
4. 11.5 ml of glacial acetic acid is added to the residue with stirring. Allow fifteen minutes for digestion.
5. 50.1 ml of concentrated hydrochloric acid is added to the residue with stirring, until the solsution becomes clear.
6. 2.833 g of anhydrous sodium acetate is added. Stir until the salt goes into solution. Final volume is 263 ml.

Synthesis of cobalt citrate complex 1. 57.46 of $CoCl_2.6H_2O$ is dissolved in pure water. 19.32 g of solid NaOH is added with stirring. Allow fifteen minutes for digestion.
2. Ammonium citrate was prepared by mixing 32.2 ml of $NH_4OH$ with 30.93 g of citric acid. This solution was stirred into the residue.
3. Filter to collect the residue.
4. 4.677 g of citric acid is added to the residue with stirring. Allow fifteen minutes for digestion.
5. 56.4 ml of concentrated hydrochloric acid is added to the residue with stirring. Stir until it becomes a clear solution.
6. 1.122 g of anhydrous sodium citrate is added, with stirring, until it dissolves. Final volume is 248 ml.

Synthesis of zinc acetate complex 1. 52.28 g of $ZnCl_2$ is dissolved in pure water. 30.69 g of solid NaOH is added with stirring. Allow fifteen minutes for digestion. The reaction is very exothermic.
2. 59.14 g of ammonium acetate is added with stirring.
3. Filter to collect the residue.
4. 20.5 ml of glacial acetic acid is added to the residue with stirring. Allow fifteen minutes for digestion.
5. 89.5 ml of concentrated hydrochloric acid is added, with stirring, until a clear solution exists.
6. 5.066 g of anhydrous sodium acetate is added to the solution. Stir until it is dissolved. Final volume is 302 ml.

Synthesis of zinc citrate complex 1. 45.9 g of $ZnCl_2$ is dissoslved in pure water. 26.944 g of solid NaOH is added with stirring. The solution is very exothermic. Allow fifteen minutes for digestion.
2. Ammonium citrate was prepared by mixing 44.9 ml of concentrated $NH_4OH$ to 43.14 g of citric acid with stirring. Pour this into the residue with stirring. The ammonium citrate dissolves the white residue so there was no filtering of this system.
3. 6.523 g of citric acid is stirred into the solution. Allow fifteen minutes for digestion.
4. 78.6 ml of concentrated hydrochloric acid is added, with stirring, to the complex.
5. 1.563 g of anhydrous sodium citrate was added. The solution was stirred until the salt dissolved. Final volume is 273 ml.

Synthesis of tin acetate complex 1. 40.82 g of $SnCl_2.2H_2O$ was dissolved in pure water. 14.473 g of solid NaOH was added with stirring, until properly mixed. Allow fifteen minutes for digestion. The reaction is very exothermic.
2. 27.9 g of ammonium acetate is added to the residue with stirring.
3. Filter the residue.
4. 9.8 ml of glacial acetic acid is added with stirring. Allow fifteen minutes for digestion.
5. 92.2 ml of concentrated hydrochloric acid is added to the residue with stirring. Add pure water with stirring until a clear solution forms.
6. 2.389 g of anhydrous sodium acetate is added, with stirring, until the salt is dissolved. Final volume is 500 ml.

Synthesis of tin citrate complex 1. 40.8 g of $SnCl_2.2H_2O$ is dissolved in pure water. 14.466 g of solid NaOH is added with stirring until properly mixed. The reaction is very exothermic. Allow fifteen minutes for digestion.
2. Ammonium citrate is prepared by mixing 24.1 ml $NH_4OH$ to 23.158 g citric acid. After properly mixing, add mixture to the residue with stirring.
3. Filter the residue.
4. 3.63 g of citric acid is added to the residue with stirring. Allow fifteen minutes for digestion.
5. 92.2 ml of concentrated hydrochloric acid is added to the residue with stirring. Add pure water with stirring, until a clear solution exists.
6. 0.84 g of anhydrous sodium citrate is added to the clear solution and stirred until the salt dissolves. Final volume is 420 ml.

Synthesis of magnesium acetate complex 1. 38.78 g of solid $Mg(OH)_2$ is added to pure water.
2. 102.474 g of ammonium acetate is added with stirring.
3. Filter to collect the precipitate.
4. 34.1 ml of glacial acetic acid is added to the residue with stirring. Allow fifteen minutes of digestion time.
5. 149.2 ml of concentrated hydrochloric acid is added to the residue, with stirring, until a clear solution is formed.
6. 8.477 g of anhydrous sodium acetate is added, with stirring, until the salt is dissolved. Final volume is 480 ml.

Synthesis of magnesium citrate complex 1. 39.27 g of solid $Mg(OH)_2$ is stirred into pure water.

2. Ammonium citrate is prepared by mixing 89.7 ml of concentrated NH₄OH to 86.218 g of citric acid with stirring. Stir this salt solution into the Mg(OH)₂ mixture.
3. Filter to collect the precipitate.
4. 12.982 g of citric acid is added to the residue with stirring. Allow fifteen minutes for digestion.
5. 156 ml of concentrated hydrochloric acid is added to the residue, with stirring, until the solution becomes clear.
6. 3.109 g of anhydrous sodium citrate is added to the clear solution and stirred until the salt dissolves. Final volume is 390 ml.

Synthesis of calcium acetate complex 1. 31.49 g of solid Ca(OH)₂ is added to pure water.
2. 65.522 g of ammonium acetate is added to the mixture with stirring. Must keep stirring the mixture vigorously to prevent the mixture from solidifying.
3. Filter to collect the precipitate.
4. 21.8 ml of glacial acetic acid is added to the precipitate with stirring. The acetic acid solidifies. To prevent the solidification the system must be vigorously stirred. Allow fifteen minutes for digestion.
5. 95.4 ml of concentrated hydrochloric acid is added to the mixture while stirring. Stir until a clear solution is formed.
6. 5.42 g anhydrous sodium acetate is added. Stir until the salt dissolves. Final volume is 425 ml.

Synthesis of calcium citrate complex 1. 31.9 g of solid Ca(OH)₂ is stirred into pure water.
2. Ammonium citrate was prepared by mixing 57.4 ml of concentrated NH₄OH to 55.149 g of citric acid. Stir to complete the reaction. Add this to the Ca(OH)₂ mixture. Stir vigorously to prevent solidification.
3. Filter to extract the precipitate.
4. 8.304 g of citric acid is added to the residue while stirring. Allow fifteen minutes to digest.
5. 150 ml of concentrated hydrochloric acid is added to the residue with stirring. Add pure water with stirring until a clear solution is formed.
6. 2.0 g of anhydrous sodium citrate is added to the solution while stirring. Stir until it dissolves. Final volume is 490 ml.

The general procedure of the synthesis of a solar metallic carboxyl complex is

1. Dissolve an ionic metallic salt in water to place the metal ion in the high spin (spin free) (weak field) hybridized state. Add a quantity of solid sodium hydroxide which will tie up the desired number of bond sites for the carboxyl group. Let it digest for fifteen minutes.
2. Add enough carboxyl ions, as the ammonium carboxylate salt, to bump the hydroxyl ions. Hopefully the NH₃ will tie up some of the remaining hybridized metal ion bond sites.
3. Filter overnight.
4. Add some more carboxyl ions to the residue, as the carboxyl acid.
5. Dissolve the residue in concentrated hydrochloric acid. Hopefully some Cl⁻ will enter the metal ion's coordination field, because of their enormous numbers.
6. Add a little more carboxyl ions, as the sodium salt, in the case the system needs stabilization due to the bonded Cl⁻ ligands.

The above-mentioned ligands can form various complexes with the metal depending upon the ratios of the various ligands which attach to the four- or six-bonding sites and the precise bonding site occupied by each ligand. For example, it is possible to form an iron acetate complex having three acetate ligands, 2Cl⁻ ligands and one NH³ ligand. Such a complex could have the following formula:

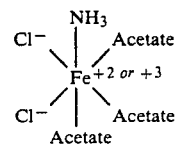

Formula III

It will be appreciated that the complex representated by formula III is one particular stereoisomer and that other stereoisomeric forms are possible depending upon which particular bonding sites are occupied by each of the six identified ligands. Formula III represents a cis isomer which can be referred to as triaceto-cis-dichloroamine ferrate III or triaceto-cis-dichloroamine ferrate II depending on whether the iron is in the $Fe^{+3}$ or $Fe^{+2}$ state, respectively.

Triaceto-dichloroamine ferrate III and its stereoisomers are indicated by the formula $[Fe^{+3}(CH_3COO^-)_3(Cl^-)_2(NH_3)]^{-2}$, and the triaceto-dichloroamine ferrate II and its sterioisomers are indicated by the formula $[Fe^{+2}(CH^3COO^-)_3(Cl^-)_2(NH_3)]^{-3}$.

It is also possible for the iron acetate complex to have two acetate ligands, two Cl⁻ ligands and two NH₃ ligands. Such a complex could be represented by the formula:

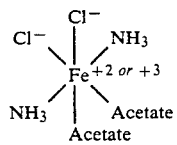

Formula IV

It will be appreciated that the compound of formula IV is one particular stereoisomer and that other stereoisomers are possible as was the case for formula III. Formula IV represents a cis-diaceto-cis-dichloro-trans-diamine ferrate III or cis-diaceto-cis dichloro-transdiamine ferrate II depending on whether the iron is in the $Fe^{+3}$ or $Fe^{+2}$ state, respectively. Diaceto-dichloro-diamine ferrate III and its stereoisomers are represented by the formula:

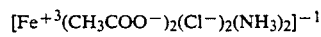

Diacetodichlorodiamine ferrate II and its stereoisomers are represented by the formula:

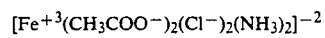

It will be readily apparent that additional forms of iron acetate complexes having the six-bonding sites occupied by acetate, Cl⁻ and NH₃ are possible other than the specific ones mentioned above. Examples of other specific iron acetate complexes include, but are not limited to the following: trichloro trans-diacetoamine ferrate II and III; cis-diaminecis-dichloro-cis diaceto ferrate II and III and trans-diamine-trans-dichloro-trans diaceto ferrate II and III.

It will be readily appreciated that the iron citrates can also exist in various forms. For example, it is possible that the iron citrate complex contains one chelated citrate ligand, one or two Cl$^-$ ligands and one or two NH$_3$ ligands.

A complex having one citrate ligand, two Cl$^-$ ligands and one NH$_3$ ligand may have the following formula:

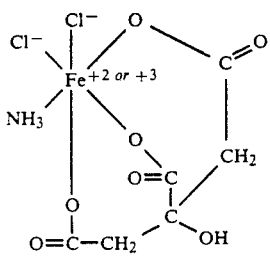

It will also be appreciated that the compound represented by formula V is one particular stereoisomer and that other stereoisomers are possible as was the case for the acetate complexes. Formula V represents the cis dichloro amine iron citrate complex which can be referred to as citrato-cis-dichloro-amine ferrate III or citrato-cis-dichloro-amine ferrate II depending upon whether the iron is in the +3 or +2 valence state, respectively.

Citrato-dichloro-amine ferrate III and its stereoisomers are represented by the formula:

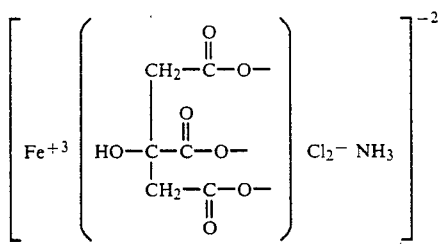

Citrato-dichloro amine ferrate II and its steroisomers are represented by the following formula:

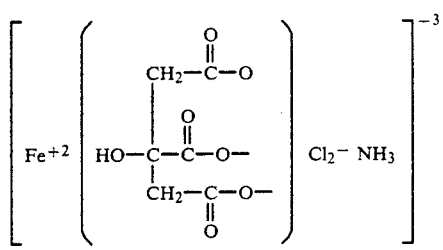

It is also possible for the iron citrate complex to have one citrate ligand, one Cl$^-$ ligand and two NH$_3$ ligands. Such a complex could be represented by the following formula:

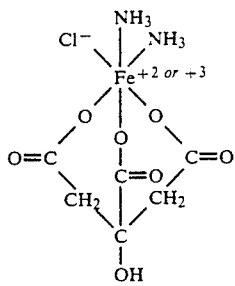

It will also be appreciated that the complex representated by formula VI is one particular stereoisomer and that other stereoisomers are possible for the six identified ligands as was the case for the compounds of formulae I–V.

Formula VI represents the cis-diamine-chloro iron citrate complex which is referred to a citrato-cis-diamine-chloro ferrate III or citrato-cis-diamine-chloro ferrate II depending upon whether the iron is in the Fe$^{+3}$ or Fe$^{+2}$ valent state, respectively.

Citrato-diamine-chloro ferrate III and its stereoisomers are represented by the following formula:

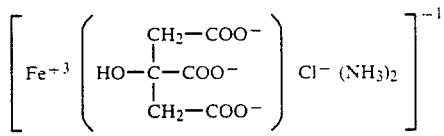

Citrato diamine-chloro ferrate II and its stereoisomer are represented by the following formula:

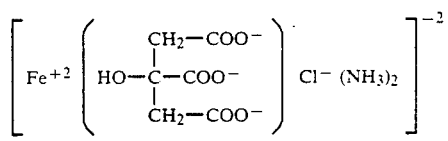

It will also be readily apparent that the iron citrate complexes having the six-bonding sites occupied by citrate, Cl$^-$ and NH, ligands can exist in additional forms other than the specific ones described above.

FIG. 17 demonstrates that if any of these isomers are initially formed, then the unbonded carboxyl group was converted to CO$_2$ because there is no —COO$^-$ peak at 1600 cm$^-$.

The carboxyl ligands have been described in the above formulae as having an ionic linkage between the metal atom and the carboxyl anion. Such a linkage is illustrated as follows:

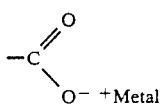

Although it is believed that the reactions used to make the complexes result in the above ionic linkage, it is also believed that covalent linkages are also eventually formed. In the covalent linkage, a carbon atom is bonded directly to the metal as illustrated below:

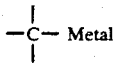

It is believed that the above covalent linkage is formed in the sunlight by the power producing cell in accordance with the following reaction for acetate and citrate complexes, respectively:

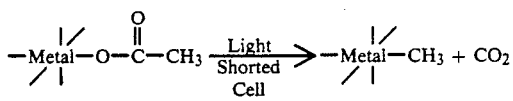

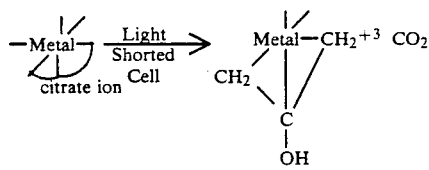

Ligands which have the above type of covalent linkage are considered to be carboxyl derivative ligands.

The formation of the covalent linkage in the carboxyl derivative ligands requires the removal of the carboxyl group from the acid molecule so that the adjacent carbon atom may be covalently bonded to the metal.

It is believed that the complexes having the covalent linkage are more stable in the solar cells of this invention and they do not required an acidic solution having a pH of 1-4. The complexes having the covalent linkage are termed organometallic. They are observed in the turbid solution formed in the cells. Their organometallic nature is demonstrated in FIG. 17.

When a carbxylic acid is used to form the complex, it is possible that only some of the carboxyl groups will react to form covalent linkages as described above. Thus, it is possible for the citric acid complex to have one or two covalent linkages and one or two ionic linkages.

It is also expected that the complexes used in the cells will have a mixture of ionic species and covalent species since the covalent species appear to develop after a period of time in the power producing cells. Cells which developer greater turbidity have more covalent metallic complex.

The acetate and citrate (chloroamine citrato metal $+n$ and $+m$ and chloroaminoaceto metal $+n$ and $+m$) complexes may be characterized by their absorption spectra. The twenty-two complexes described herein were subject to spectraoscopic studies. The spectra were recorded in the u.v. and visible region from 186 to 825 nm by use of an Hitachi Perkin Elmer (Coleman 124) spectrophotometer. Infrared spectroscopy studies were performed on the Perkin Elmer model 700 Infrared Spectrophotometer. Chemicals used were Fisher ACS grade.

FIG. 1 shows the spectroscopy data of approximately 1 M acetate and citrate complexes which were made by the preferred process. Absorption is maximum for the Fe citrate complex from about 186 nm to 513 nm. Absorption was maximum for the iron acetate complex from about 186 nm to 522 nm.

Figure 2:
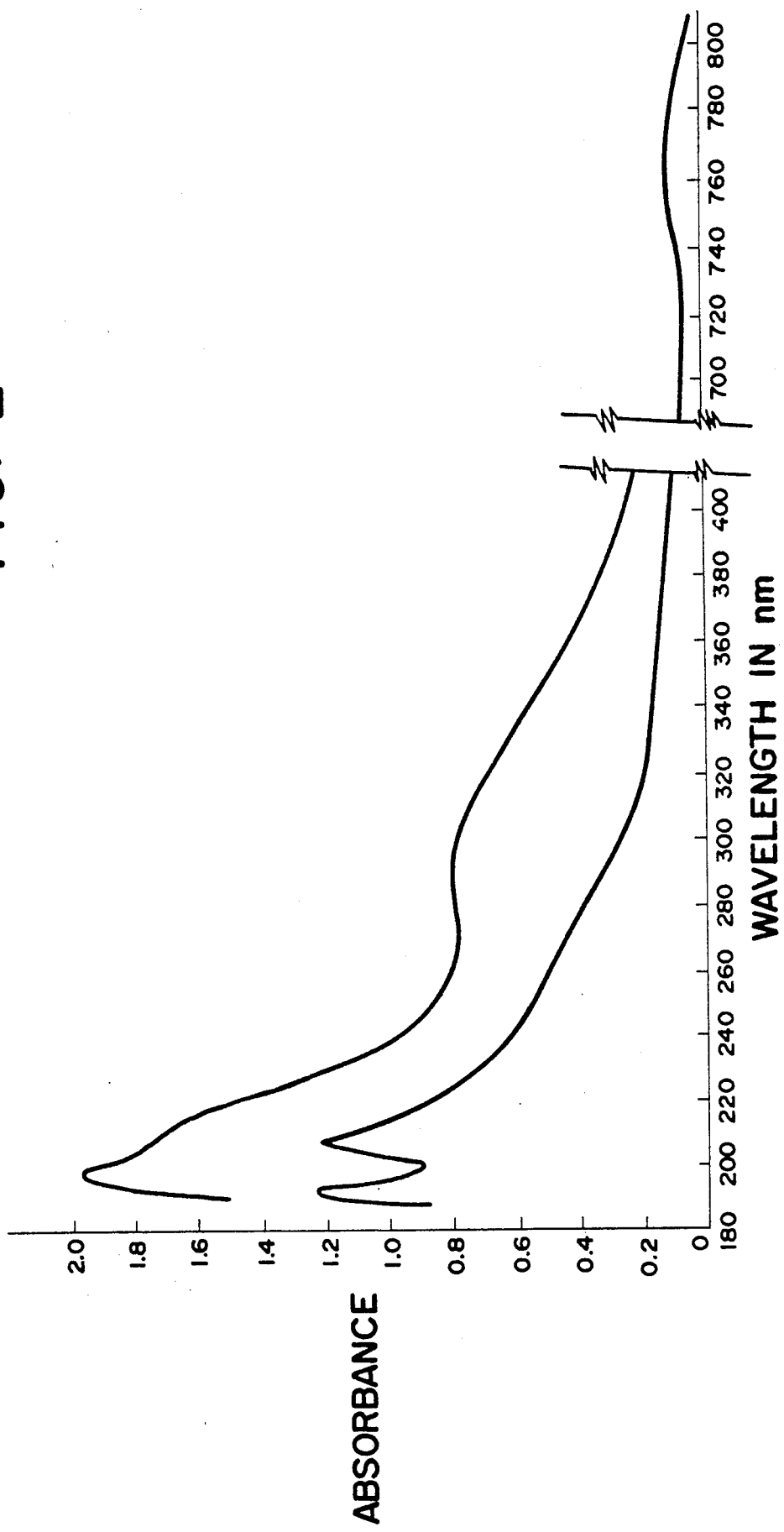
FIG. 2 is a graph which shows the absorbance spectra of unbuffered iron acetate complex and iron citrate complex of a very dilute solution.

Spectroscopy studies were also performed on dilute samples for obtaining more precise determination of the maximum absorption peeks. The top line of FIG. 2 shows the absorption spectra of a $4 \times 10^{-4}$ M solution of the iron acetate complex made by the preferred method. The bottom line in FIG. 2 represents the absorption spectra of a $1.5 \times 10^{-4}$ M solution of the iron citrate complex made by the preferred method. Neither solution contains a buffer. The citrate complex produces a strong peak near 190 nm and 210 nm and a weak peak near 760 nm. The acetate complex produces a strong peak near 190 nm and near 210 nm, and a medium peak near 290 nm and a weak peak near 760 nm. Neither complex produces a peak between 400-700 nm. Their spectra were the same in the visible region.

Figure 3:
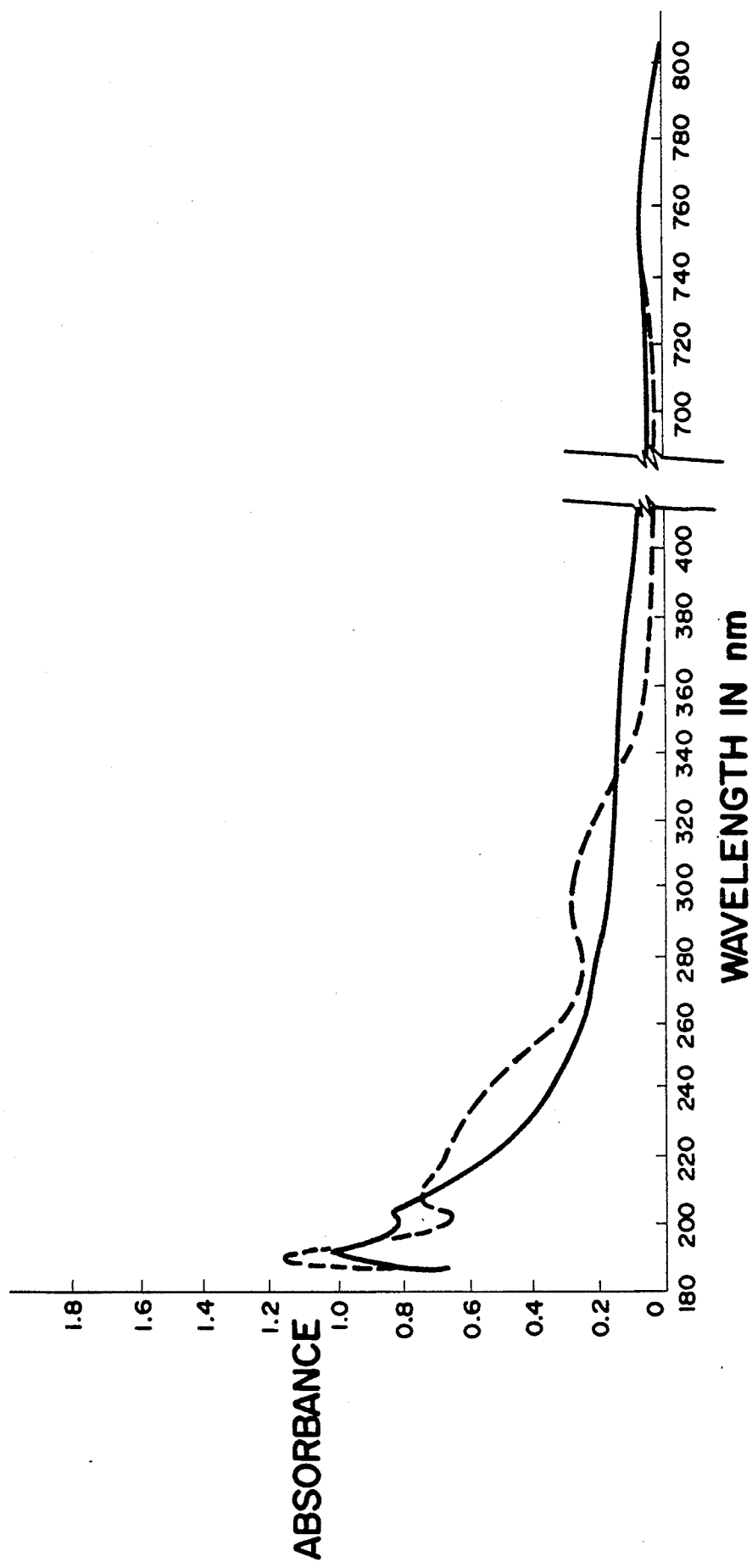
FIG. 3 is a graph showing the absorbance spectra of buffered iron citrate complex and iron acetate complex of a very dilute solution.
Figure 4:
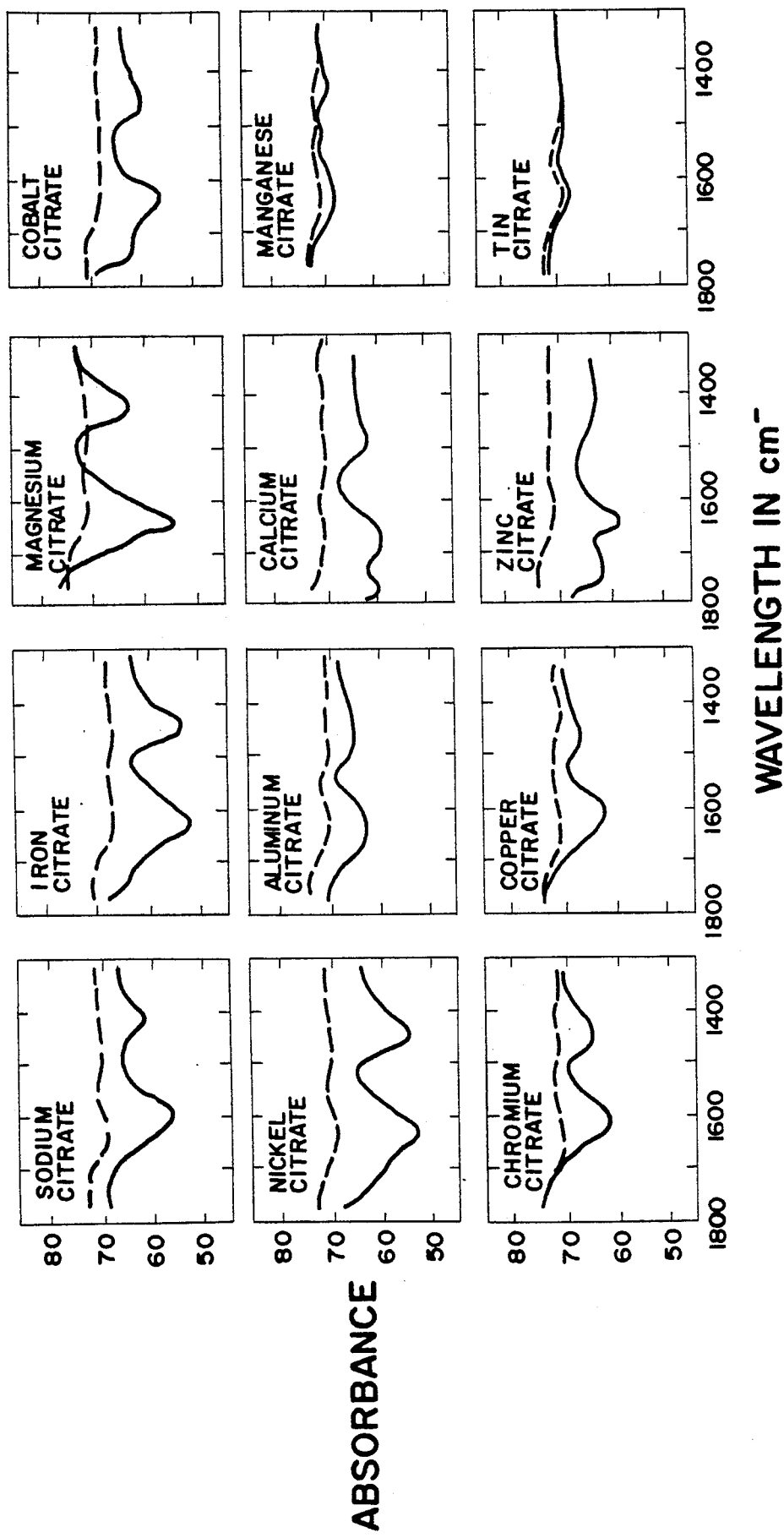
FIG. 4 is a series of graphs which show the i.r. spectra of the metallic citrate complexes that have been precipitated with 6 N NaOH.
Figure 5:
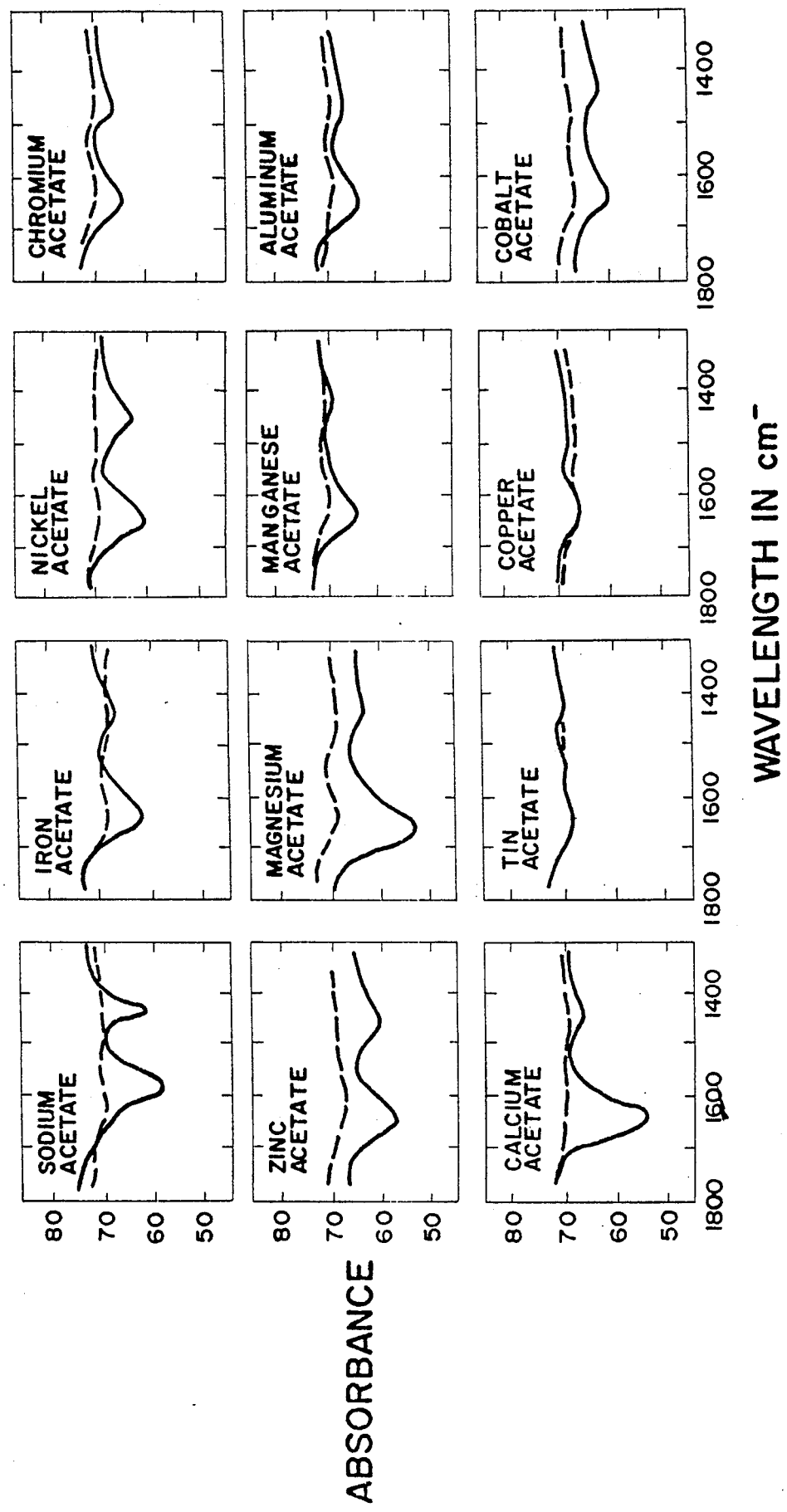
FIG. 5 is a series of graphs which show i.r. spectra of the metallic acetate complexes which have been precipitated with 6 N NaOH.
Figure 6:
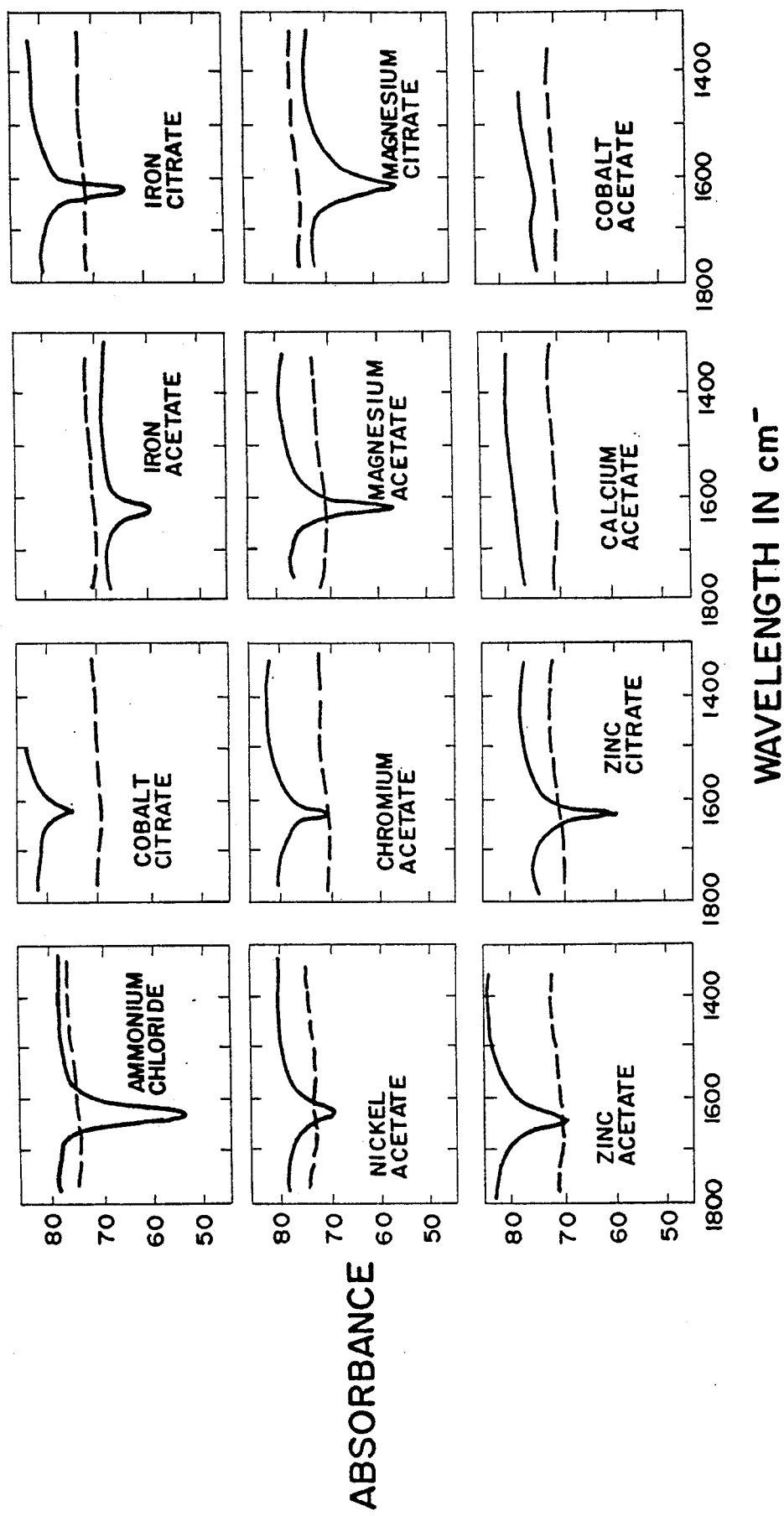
FIG. 6 is a collection of graphs which show the i.r. spectra of the organometallic complexes which have been converted to the ammonium ion thereof.
Figure 7:
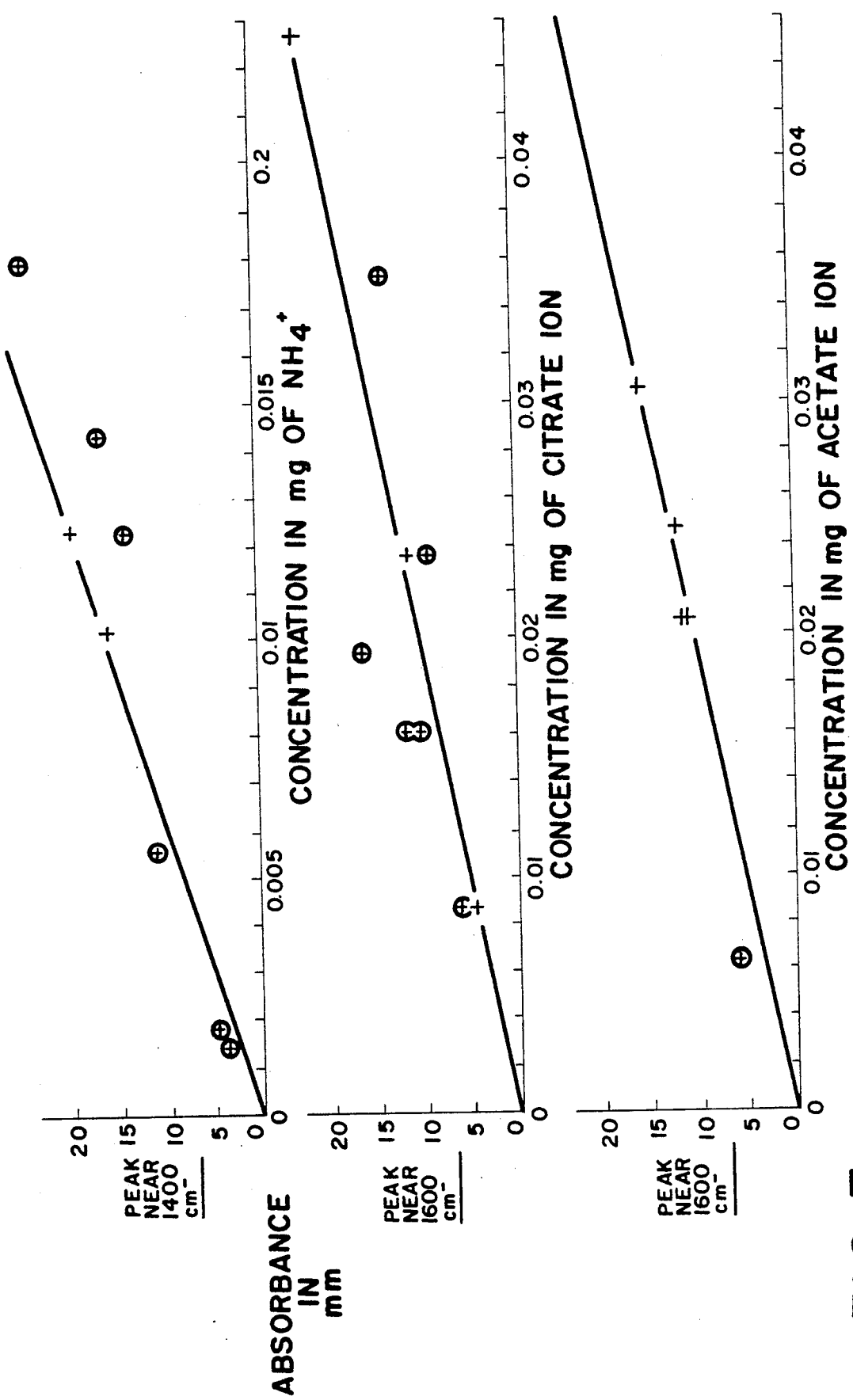
FIG. 7 is a series of graphs which show the absorbance of standard stock solution concentrations for extrapolation of ligands remaining in the coordination sphere after the metallic complexes were treated with 6 N NaOH.

FIG. 3 shows the absorption spectra of the acetate and citrate complexes which are made by the preferred method and which are also buffered with the preferred $HSO_4^-$ buffer. The buffer is one molar sulfuric acid-sodium sulfate. Both complexes of FIG. 3 are about $5 \times 10^{-6}$ M and have a buffer which is about $5 \times 10^{-5}$ M. The citrate complex shows a strong peak near 190 nm and 200 nm and a weak peak near 760 nm. The acetate complex shows a strong peak near 190 nm and 210 nm, a medium peak near 300 nm and a weak peak near 760 nm.

Extremely dilute unbuffered u.v.-visible spectra of the remaining metal complexes produce strong peaks in the ultra-violet region (see FIGS. 8-10) and very weak broad peaks in the visible region. Cobalt citrate complex produced a strong peak near 205 nm but no appreciable weak peak in the visible region. Cobalt acetate complex produced a strong peak near 191 nm and a very weak broad peak near 753 nm. Nickel acetate produced a strong peak near 193 nm and a very broad weak peak near 760 nm. Nickel citrate produced a strong peak near 192 nm and a very broad peak near 760 nm. Tin citrate complex produced a strong peak near 201 nm and a very broad peak near 774 nm. Tin acetate complex produced a strong peak near 201 nm and a very weak broad peak near 640 nm. Magnesium citrate shows a strong peak near 197 nm and a very weak broad peak near 677 nm. Magnesium acetate complex shows a strong peak near 193 nm and a very weak broad peak near 510 nm. Zinc citrate complex shows a strong peak near 192 nm and a very weak broad peak near 465 nm. Zinc acetate complex shows a strong peak near 194 nm and a weak broad peak near 700 nm. Calcium acetate complex shows a strong peak near 191 nm and a weak broad peak near 725 nm. Calcium citrate shows a strong peak near 191 nm and a weak broad peak near 750 nm. Manganese citrate shows a strong peak near 191 nm and a weak broad peak near 675 nm. Manganese acetate complex shows a strong peak near 190 nm and a weak broad peak near 665 nm. Aluminum acetate complex shows a strong peak near 203 nm and a weak broad peak near 650 nm. Aluminum citrate shows a strong peak near 203 nm and a weak broad peak near 675 nm. Copper citrate complex shows a strong peak near 193 nm and a weak broad peak near 665 nm. Copper acetate complex show a strong peak near 190-210 nm and a weak broad peak near 680 nm. Chromium citrate complex shows a strong peak near 203 nm and a weak broad peak near 615 nm. Chromium acetate complex shows a strong peak near 205 nm and a weak broad peak near 680 nm.

The magnitude of the strong peak in the ultra-violet region possibly suggests the charge transfer region. The very broad peak in the visible region possibly suggests the activity of the D-electrons of the subsidiary quantum numeral 1.

Additional metal acetate and citrate complexes which are useful in this invention are shown in Table 1. Table 1 shows the amount of the citrate, acetate, $NH_3$ and $Cl^-$ ligands which remain in each complex after treatment with 6N NaOH. Although this analysis does not determine the initial ligand concentration, it does indicate that the bonded ligands are still present after the harsh treatment with 6N NaOH and thereby serves to illustrate that the ligands of the complexes used in this invention are strongly attached to the bonding sites in the coordination sphere of the metal. The concentration of the acetate ions, citrate ions and ammonium ions shown in Table 1 was determined by infrared spectroscopy and extrapolated from graphs from standard stock solutions (FIGS. 4, 5, 6, and 7). The concentration of chloride ion was determined by titrations with silver nitrate.

Figure 8:
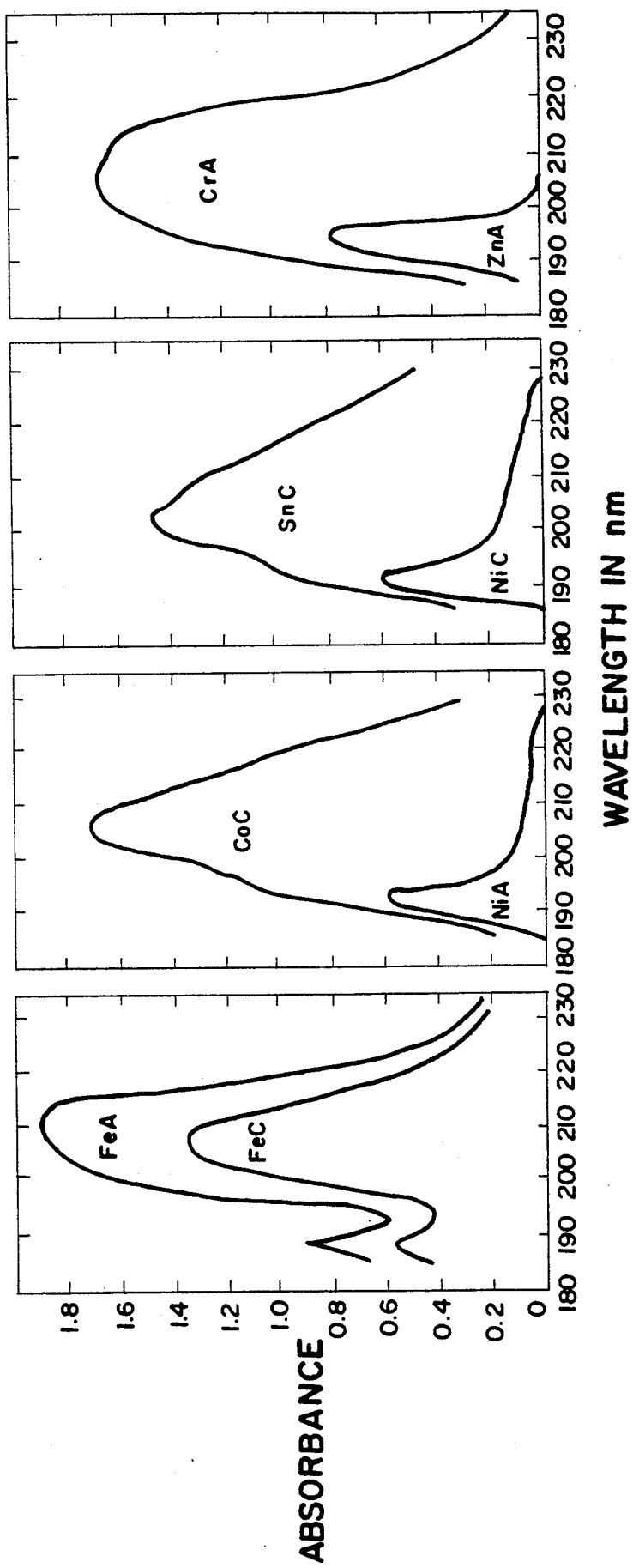
FIGS. 8, 9 and 10 are a collection of graphs which show the charge transfer region of the unbuffered metallic complexes.
Figure 9:
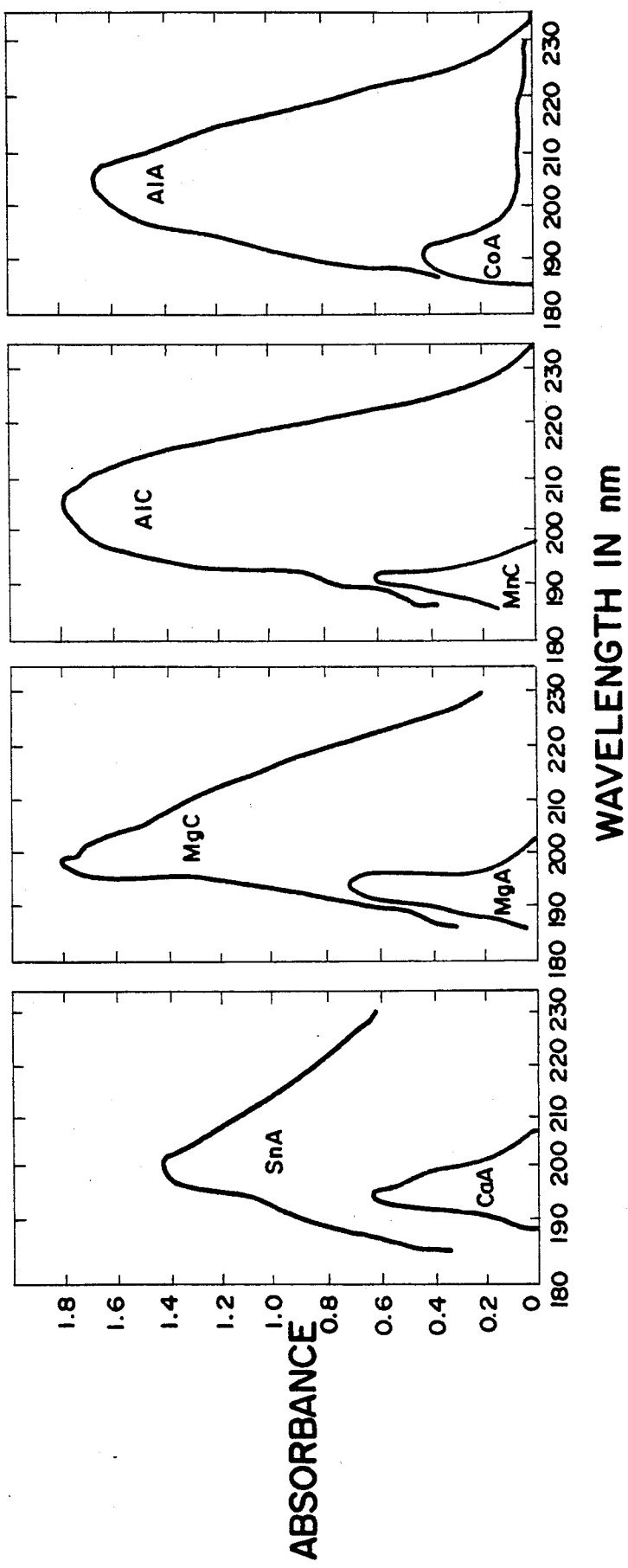
Figure 10:
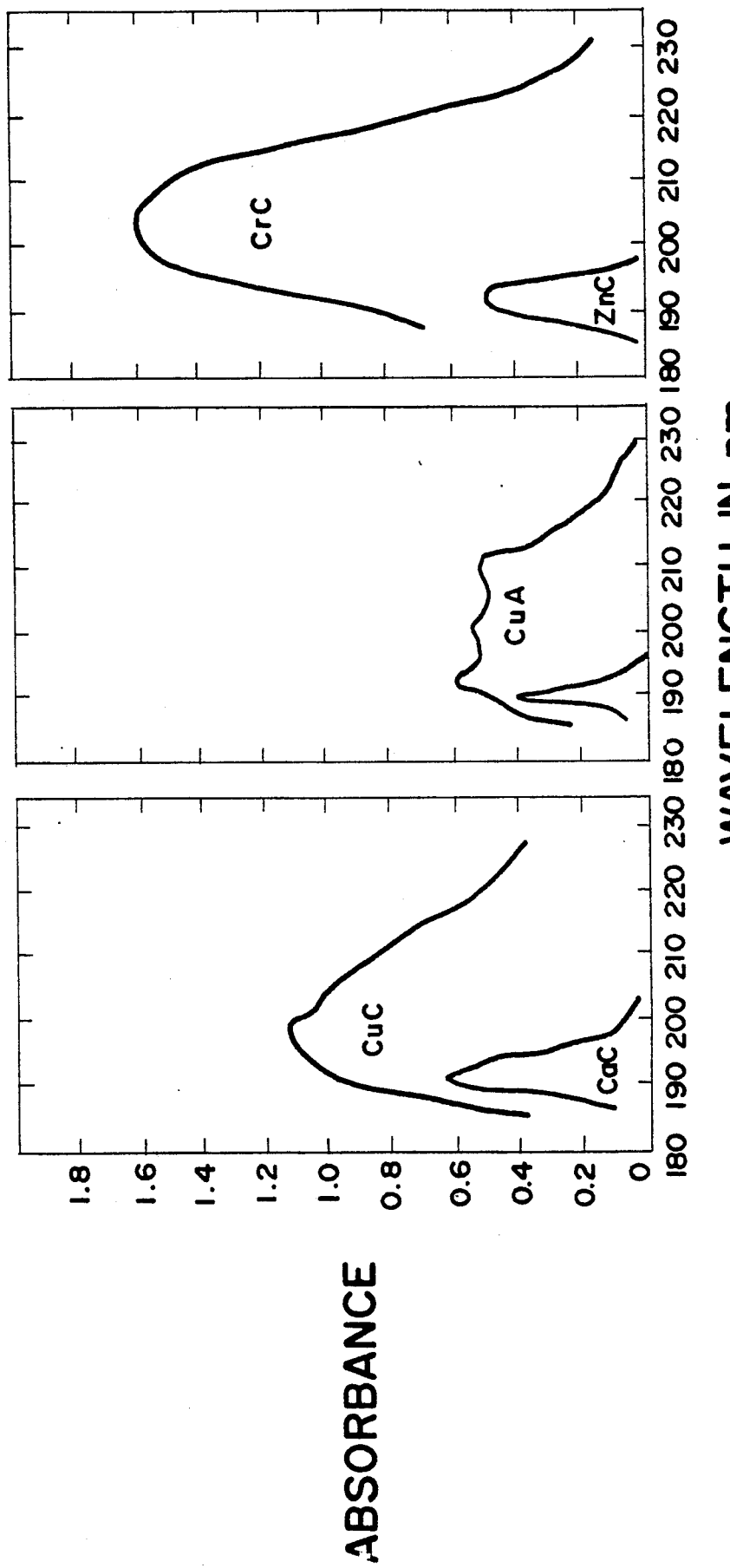

The charge transfer region of the various unbuffered complexes is shown in FIGS. 8, 9 and 10. FIG. 8 shows the charge transfer of iron acetate complex (FeA), iron citrate (FeC), cobalt citrate (CoC), nickel acetate (NiA), tin citrate (SnC), nickel citrate (NiC), chromium acetate (CrA), and zinc acetate (ZnA).

FIG. 9 shows the charge transfer region of tin acetate (SnA), calcium acetate (CaA), magnesium citrate (MgC), magnesium acetate (MgA), aluminum citrate (AlC), manganese citrate (MnC), aluminum acetate (AlA), and cobalt acetate (CoA).

FIG. 10 shows the charge transfer region of copper citrate (CuC), calcium citrate (CaC), copper acetate (CuA), manganese acetate (MnA), chromium citrate (CrC), and zinc citrate (ZnC).

All of the complexes shown in FIGS. 8, 9 and 10 were prepared without a buffer.

The photovoltaic cells of this invention use an aqueous photochemical solution containing one of the previously described metal complexes. Preferably, the solution is buffered with an aqueous solution of sulfuric acid and sodium bisulfate to maintain a pH of less than 4, most preferably 1-3. After the organometallic complex is formed, the pH is not important. The solution is made by forming a metal complex in accordance with the previously described method and adding a buffer solution to it in sufficient quantity to maintain an acid pH of less than 4. The preferred buffer solution is a one molar sulfuric acid-sodium sulfate solution.

A photochemical solution for use in this invention may be prepared by forming a solution containing the aceto or citrato chloroamine metal complex in accordance with the previously described preferred method; forming a one molar sulfuric acid-sodium sulfate buffer solution and mixing the two solutions together as follows: to 1 ml of metal complex solution add 10 ml of the buffer to form a concentrated photochemical solution which is then diluted with distilled water to a volume of 500 ml to form a solution.

For example, the photochemical solution containing acetochloroamine ferrate complex is prepared by preparing an acetochloroamine ferrate complex as described in the method of making the preferred iron acetate complex. Next, a one molar sulfuric acid-sodium sulfate buffer solution is prepared. Finally, 1 ml of the complex containing solution is mixed with 10 ml of buffer solution to form a concentrate which is diluted with water to a volume of 500 ml.

The photochemical solution containing the iron citrate complex (citratochloroamine ferrate) is made by preparing a solution containing the complex, preparing a solution containing the buffer and mixing the two solutions in the desired amounts and proportion to obtain the desired volume and proportion of complex and buffer. In a preferred embodiment, the solution containing the complex is made by mixing 326.136 g of green ferric ammonium citrate and 70.64 g of citric acid in 620 ml of distilled water and gently heating the mixture until the compounds dissolve. 381.8975 ml of concentrated hydrochloric acid is then mixed with the solution until a clear amber solution is formed.

The buffer for this preferred citrate complex embodiment is formed by adding 60 ml of concentrated sulfuric acid to distilled water and then diluting with distilled water to a volume of 500 ml to form a dilute acid solution. 103.55 g $NaHSO_4.H_2O$ is added to distilled water and diluted to a volume of 500 ml with distilled water. Both solutions are then mixed together to form 100 ml of $HSO_4^-$ buffer.

The preferred iron citrate complex is then prepared by mixing 1 ml of the solution containing the complex with 10 ml of the buffer solution to form a concentrated photochemical solution which is then diluted with 500 ml of distilled water.

The preferred embodiments for forming the iron citrate and iron acetate photochemical solution results in a concentrated solution which is diluted with 500 ml of $H_2O$ to form a final solution of about 0.002 M iron. Although a concentration of 0.002 M iron is preferred, the concentration of iron in the photochemical solution may vary considerably since any concentration of the active ingredient will function. Thus, the undiluted concentrate or more dilute solutions may be used.

The complexes are most effective when the pH is maintained below 4 until sufficient organometallic complex is formed. Any possible hydrogen gas produced could be passed over platinum powder in the acid complex to convert it back to the hydrogen ion to maintain the low pH. Some of the isomers of the complex appear to be labile and form a pseudo-colloidal suspension which is slow to settle and appears to have an infinite number of water of hydration. The colloid appears to absorb a great deal of radiation because after the colloid has somewhat settled, the power of the shorted cell goes back up. FIGS. 16 and 17 and data tables 6 and 9 demonstrate that this turbid mixture consists of the sulfate from the buffer, carbonate ion from the $CO_2$ and colloidal particles of the metallic carboxyl complex and the organometallic complex.

The twenty-two metal carboxyl complexes were used in an experimental field study. Very dilute complexes were used in the study. 1 ml of the synthesized complex plus 10 ml of 1M buffer were diluted to 500 ml. 1 ml of this complex was diluted to 7 ml with pure water in a polyethylene container. The electrodes were placed into the sunlight charged complex. The voltage and amperage readings were taken and then the electrodes of each cell were shorted, anode to cathode, and the cells were placed in the sun (see FIG. 11). The cells remained outside permanently. The voltage and amperage were recorded at noon and midnight each day. These readings were averaged to yield the twelve-hour average readings (see data table 6). The concentration of reagents in each cell were calculated from the original synthesis of each complex. This in turn was converted to milliequivalents and then to millicoulombs.

The total coulombs necessary to destroy all of the reagents if it were a straight chemical reaction was taken as the amount necessary to recycle the cell once (see data table 6). A separate test of the lead anode established that in a closed electrical system, the lead is still unaffected after enough current has passed through the system to have oxidized $Pb^o$ to $Pb^{+4}$ over eight times. Samples were extracted from the cells after the closed circuited system had produced power for more than two months. These samples were subjected to testing. The filtrate and insoluble compounds obtained from the samples were assayed by infrared spectrometry (see data table 9 and FIGS. 16A-V and 17A-D). In one test, a white turbid mixture was obtained from the samples. The white turbid mixture was centrifuged and the precipitate was washed with pure water and then the metal ion was extracted with 6n NaOH. Next the hydroxide was removed with 2n HCl. The infrared spectrum of this material shows the organic C-H stretch near 3100 $cm^-$, the C-H bend near 1400 $cm^-$ and the $-COO^-$ near 1600 $cm^-$. In another test, a sample was centrifuged and the precipitate was washed with pure water and then 12n HCl was added to destroy the $CO_3^-$ and to make the complex more soluble. The treated material of this sample was placed in a test tube and was subjected to spectrometry. The results of the spectrometry show a slight C-H stretch at 3100 $cm^-$ and a large $SO_4^{-2}$ peak from the buffer near 1100 $cm^-$ (see spectros 1 and 2 of FIGS. 17A and 17B. The contents of the test tube were shaken up so that a sample could be drawn containing the heavy quick settling residue as well as the more colloidal turbidity. Samples drawn from the test tube show that the $SO_4^{-2}$ is always in the heavy quick settling residue. Samples taken from the test tube were treated by the 6n NaOH and 2n HCl method and the i.r's spectrometry tests were conducted (see spectros 3 and 4 of FIGS. 17C and 17D). This time only the colloidal turbidity was tested. Spectros 3 and 4 show the C-H stretch near 3100 $cm^-$, the C-H bend near 1400 $cm^-$ and no $-COO^-$ near 1600 $cm^-$. This suggests that this is the organometallic complex. Spectros 1 and 2 show how tightly bonded the complex is. Data table 9 shows that the organometallic is photoelectrically active.

Data tables 7 and 8 give some insight into other possibilities of the utility of the photoelectrochemical characteristics of the complexes. Data table 7 shows the power of hydrated solid state cells. Data table 8 illustrates a possible way of utilizing the silicon solid state cells and the photochemical cells in the same system. The excess electricity produced by the silicon solid state cell could energize sun lamps indoors to store the energy.

Figure 16A:
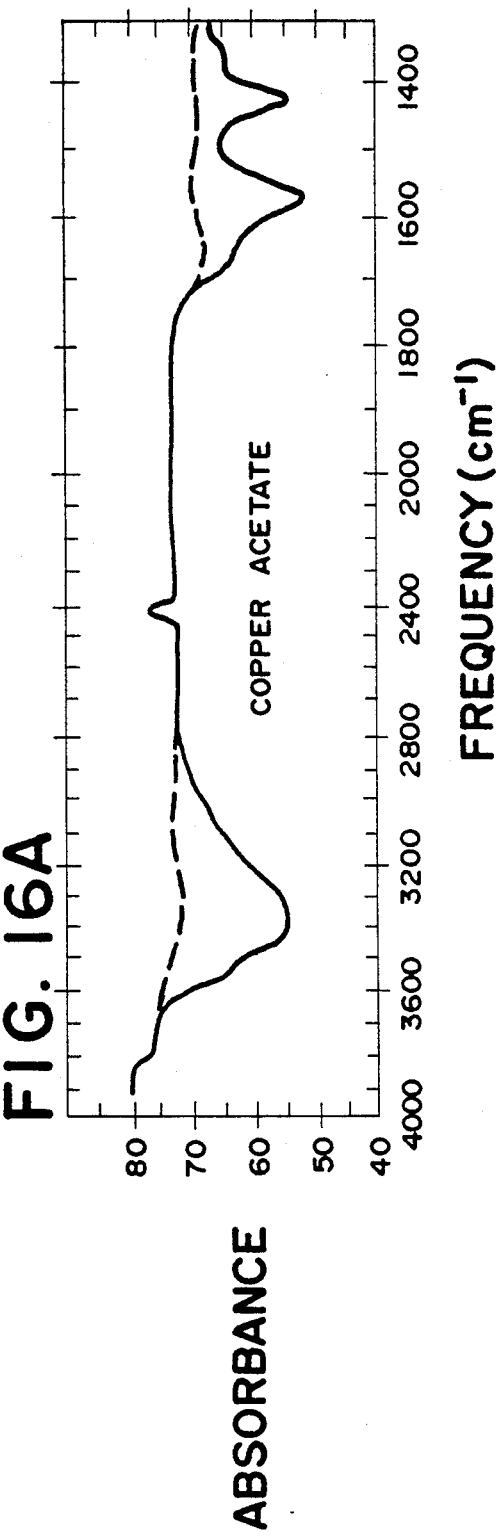
FIGS. 16A-16V shows the absorbance of chemically treated metal complexes obtained from the solar cells described in data table 6.
Figure 16B:
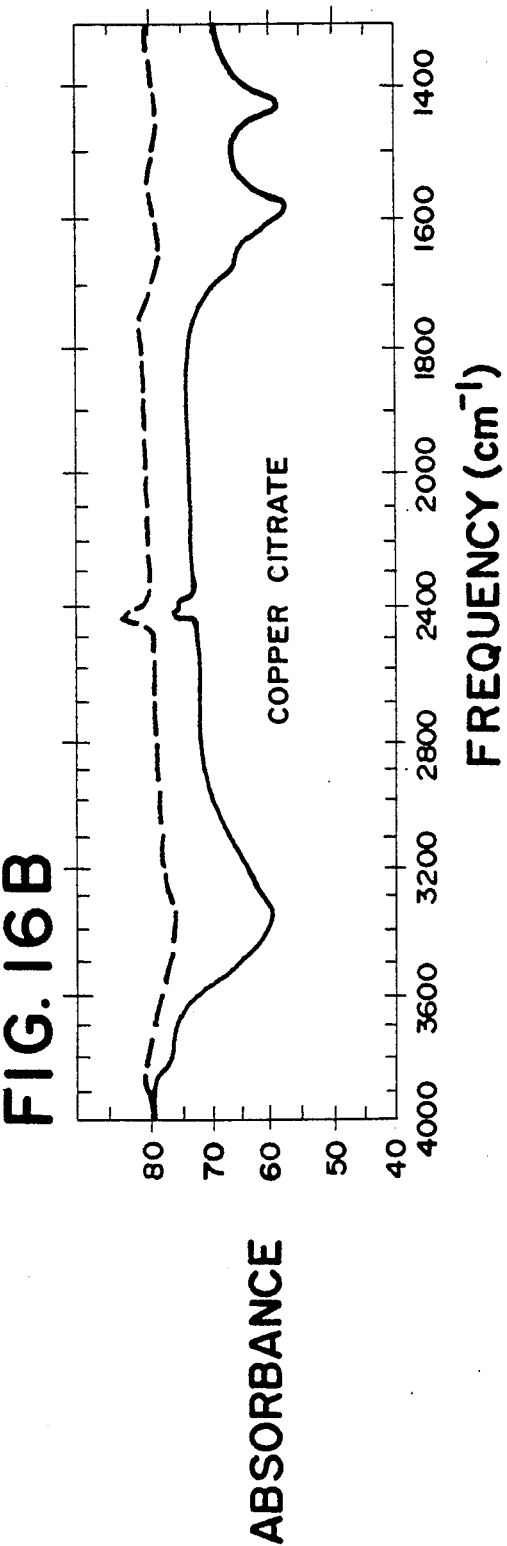
Figure 16C:
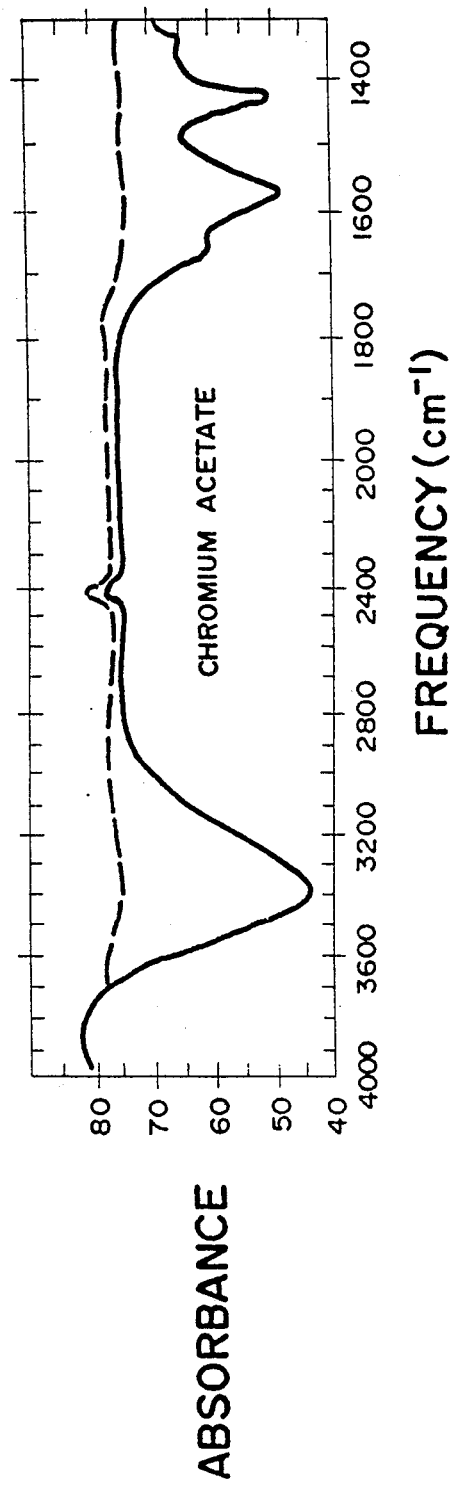
Figure 16D:
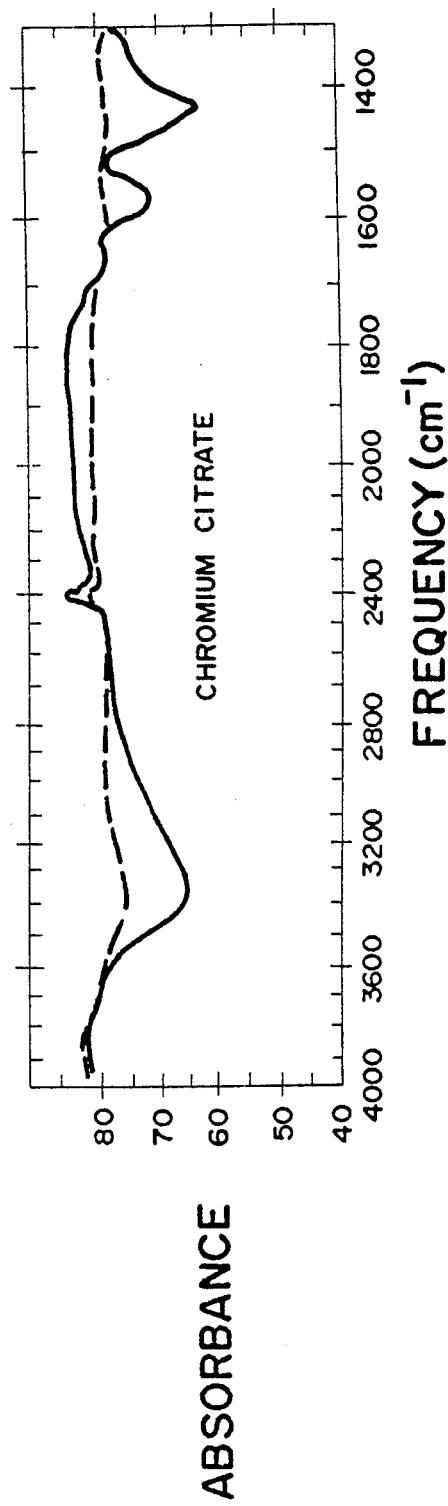
Figure 16:
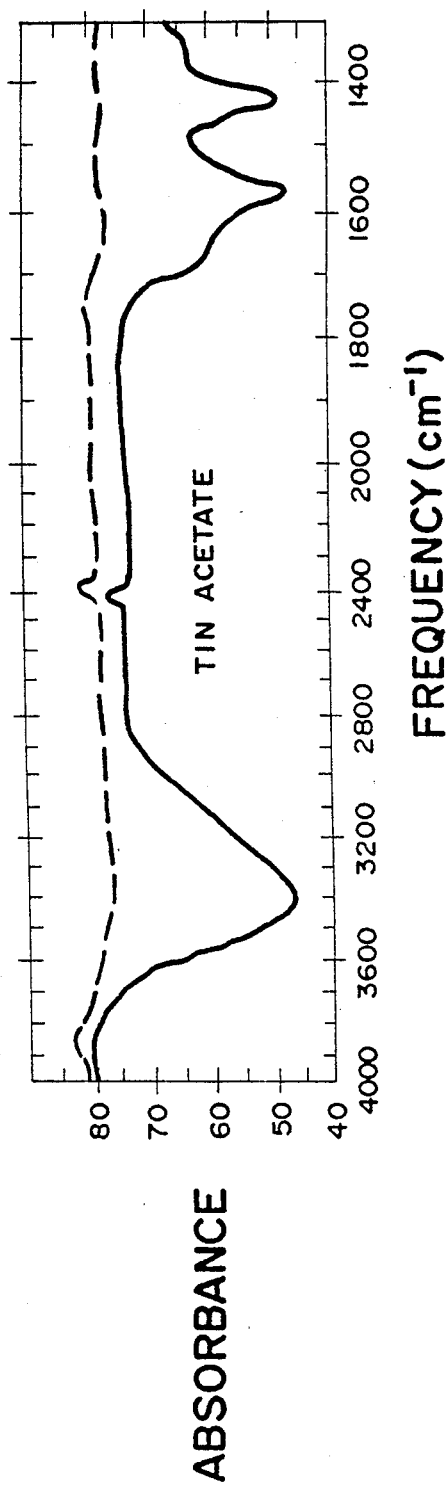
Figure 16:
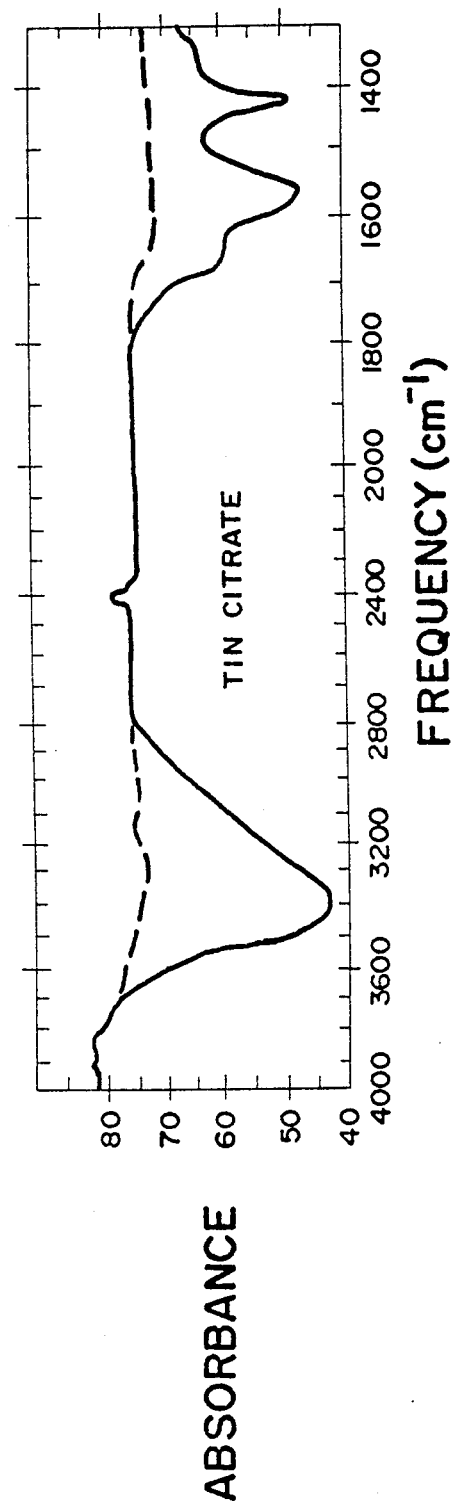
Figure 16K:
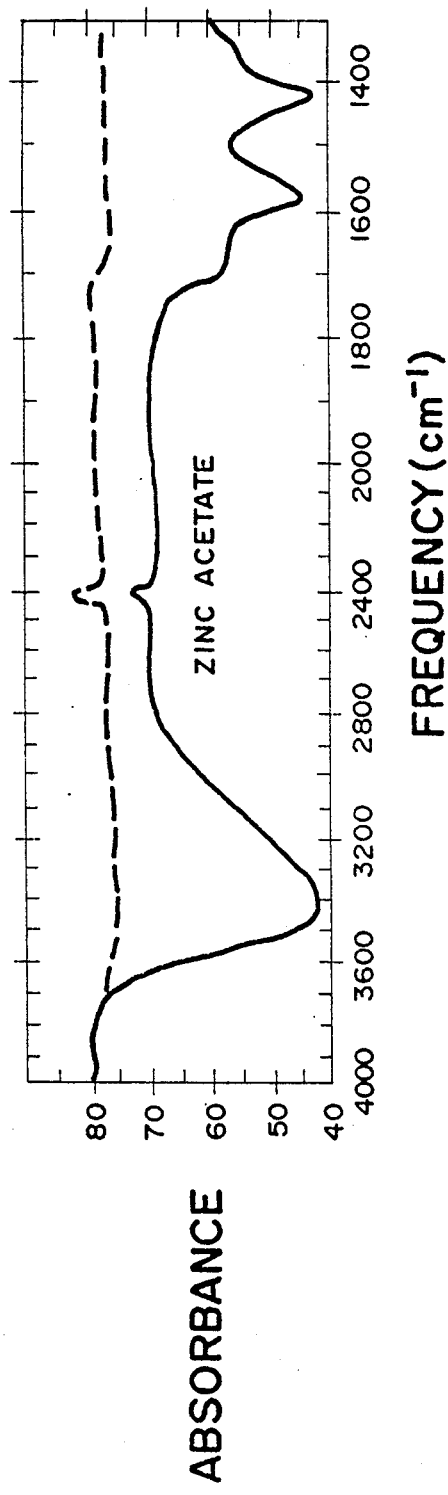
Figure 16L:
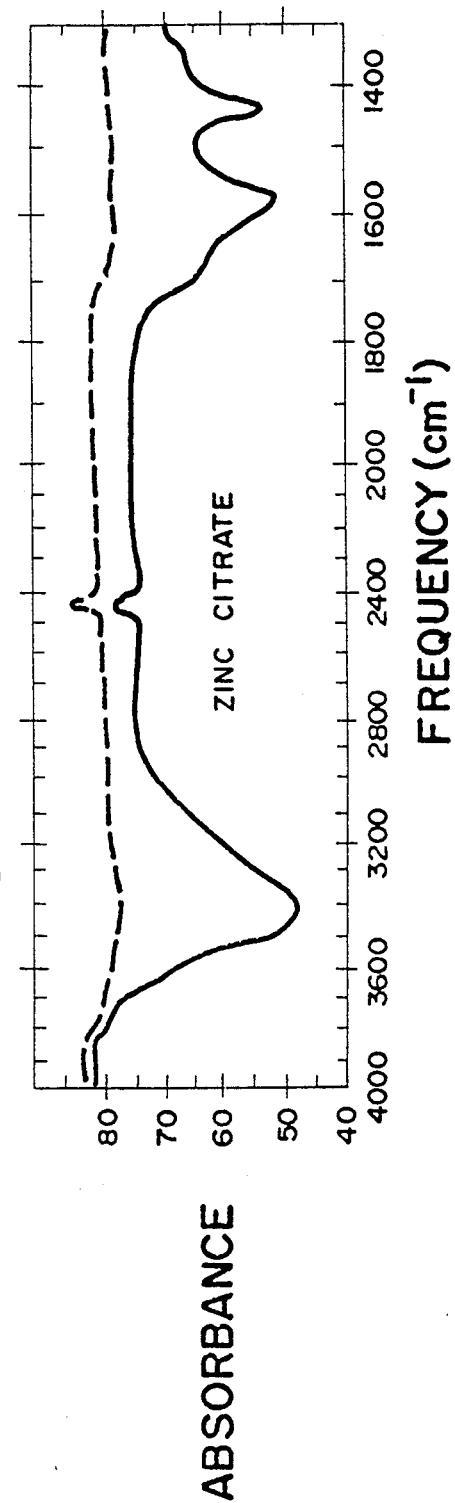
Figure 16M:
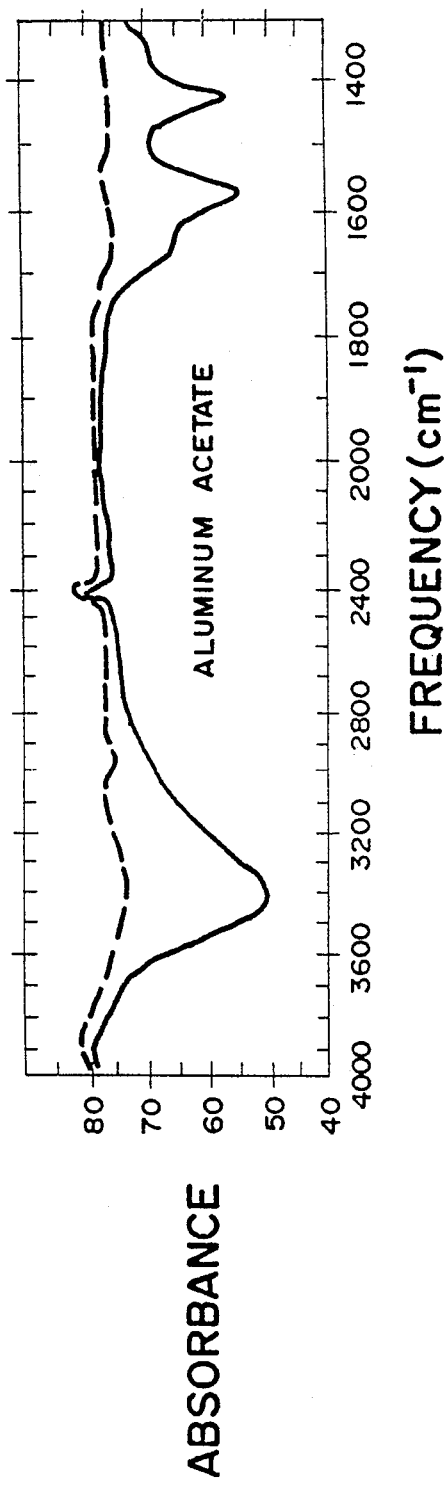
Figure 16N:
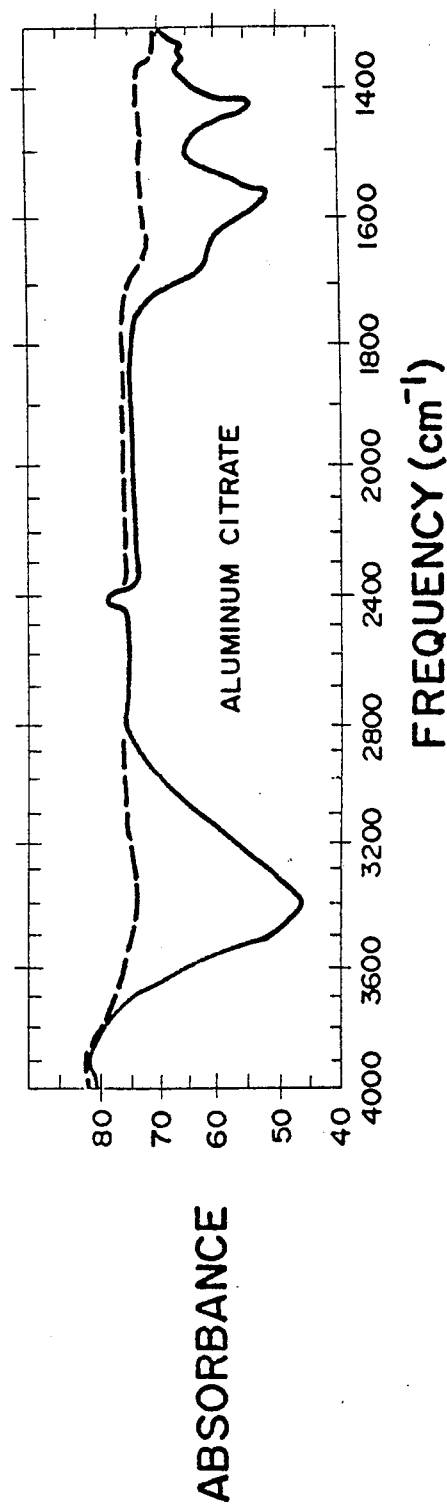
Figure 16:
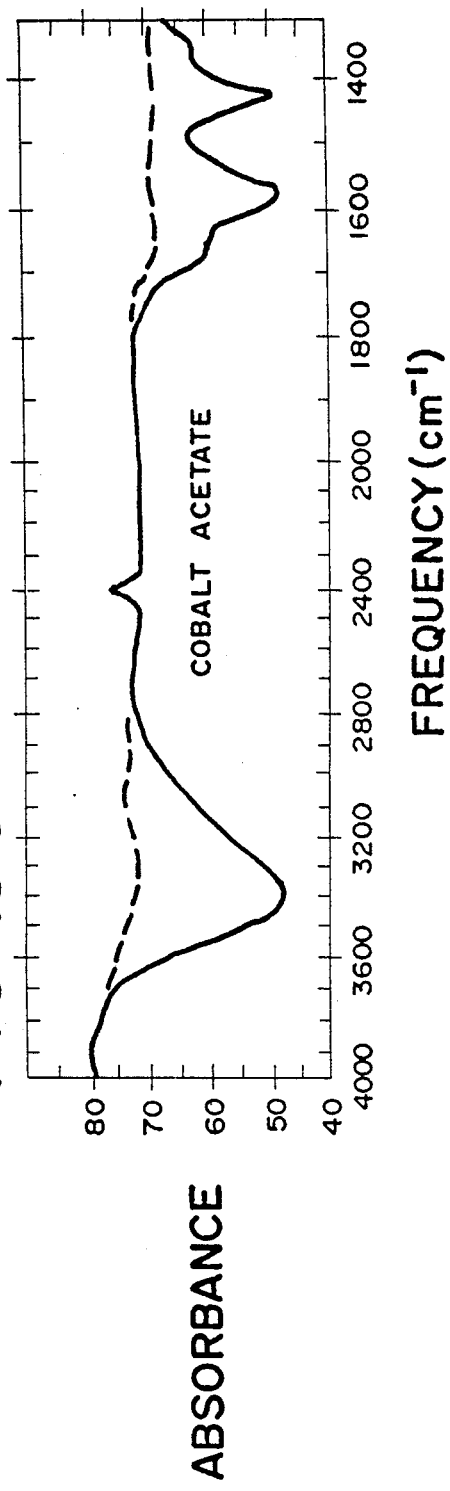
Figure 16P:
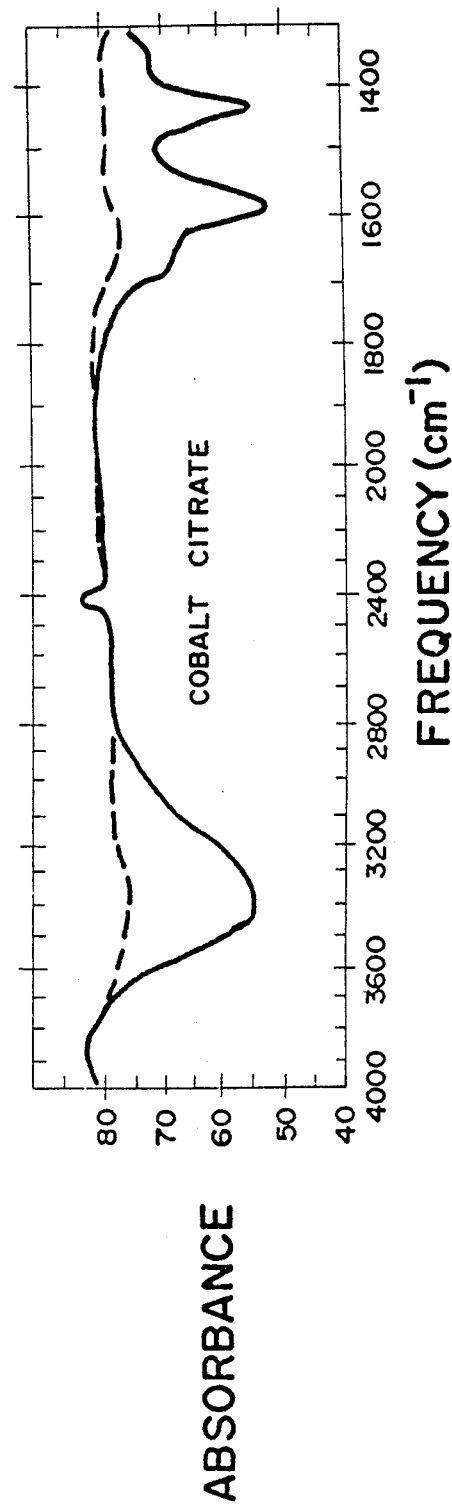
Figure 16U:
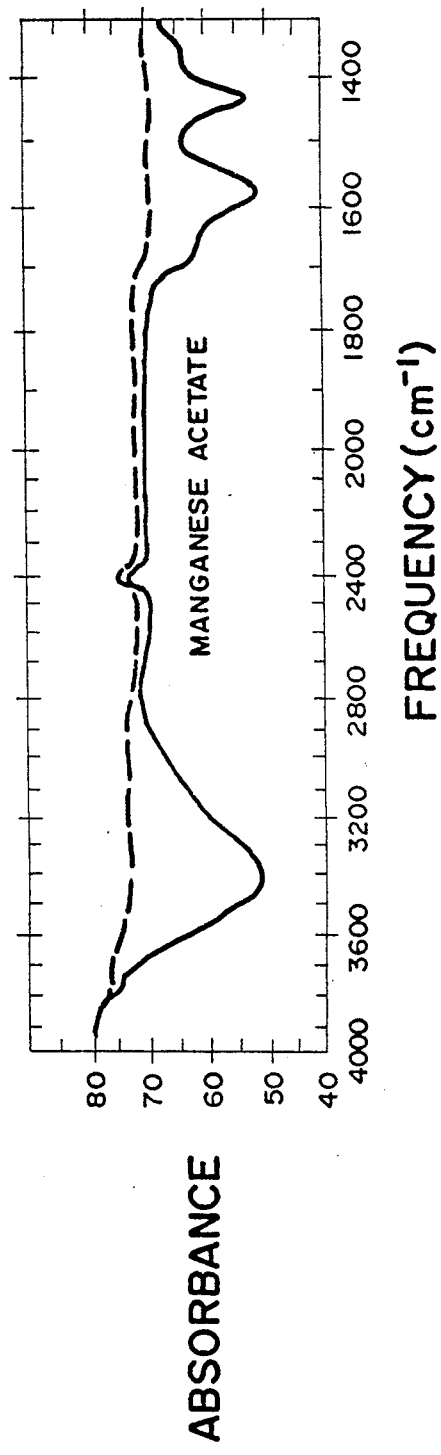
Figure 16V:
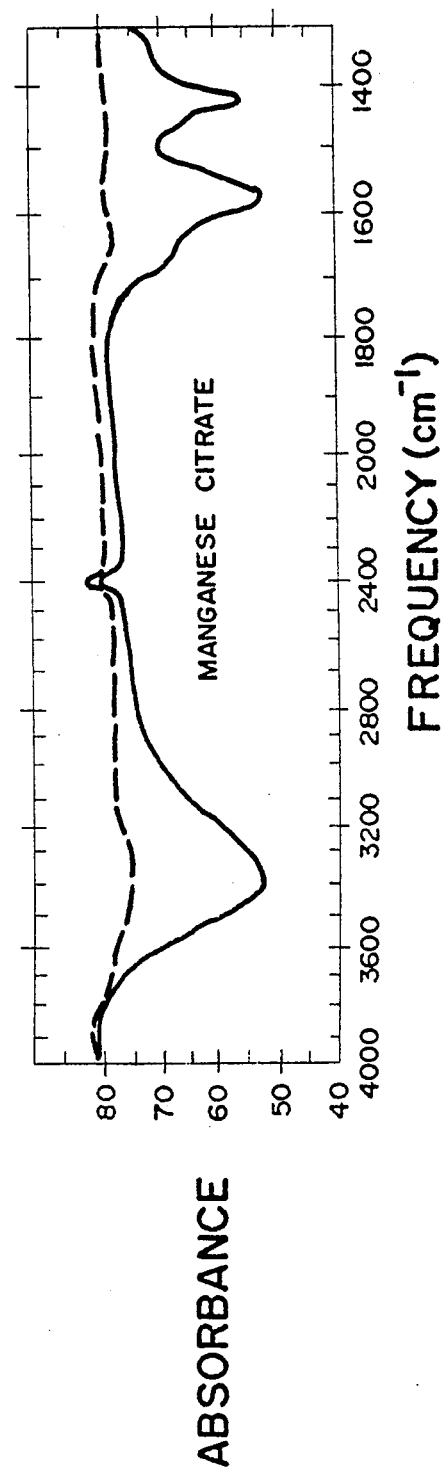

The graphs shown in FIGS. 16A-V show the absorbance of the complexes used in this invention. The data used to make the graphs shown in FIGS. 16A-V were obtained by removing 1 ml of each of the twenty-two complexes from the solar cells described in data table 6. The cells had been outside for two months or more. The solutions were colorless at the start of the experiment. At the time the samples were withdrawn, they all contained white turbidity. The samples were centrifuged and the precipitate was washed twice with pure water. 0.2 ml of 6n NaOH was added to the precipitate, which was heated to dryness at 95° C. 0.5 ml of 2n HCl was added, stirred, then heated to dryness in a 95° C. oven. A substantial quanity of $CO_2$ bubbled off when the HCl was added, apparently due to the $CO_2$ liberation from the carboxyl destruction which was converted to the carbonate ion. The dry residue was heated at 105° C. for two hours. 0.5 ml of equal volume solvent, ethanol-methanol-diethyl ether was added, stirred, and allowed to settle. One drop from the top of the solution was added to a clean NaCl window and an infrared spectro was run. The dotted graph is the clean NaCl window background and the solid graph is the complex. No other peaks appeared on the spectrum between 4000-650 $cm^{-1}$. The C-H stretch, $-COO^-$ and C-H bend respectfully appear. Some $-COO^-$ groups are still present in the filterate. Therefore the organometallic bonds are undetectable due to the $-COO^-$ bond peak at 1600nm.

FIGS. 17A-D show spectros 1-4 of the complexes obtained from seven of the best cells as described in data table 6. The cells from which the complexes were obtained, have been shorted and remained outside for at least two months. The white turbid solutions obtained from the cells were centrifuged and the precipitate was washed with pure water and centrifuged twice. 0.1 ml of 12N HCl was added to the white precipitate in an attempt to improve the solubility. The precipitate was evaporated to dryness at 95° C., then heated at 105° C. for two hours. 0.5 ml of ethanol-methanol-diethyl ether solvent was added and the solution was stirred. One drop of the turbid solution was added to a NaCl window, evaporated to dryness, and an infrared spectro was run on this specimen. The spectra appear in spectros 1 and 2 shown in FIGS. 17A and 17B, respectively. After the spectro was obtained, 0.2 ml of 6N NaOH was added to the complex and was heated for two hours at 95° C. and then 0.7 ml of 2N HCl was added and the solution was stirred. Some $Co_2$ escaped when the HCl was added. The material was evaporated in an oven at 95° C. and the dry residue was then heated for two hours at 105° C. 0.5 ml of ethanol-methanol-diethyl ether solvent was added to the residue and the solution was stirred. One drop of the turbid solution was evaporated on the NaCl windown. An infrared spectro was obtained and these spectra appear in spectro 3 and 4 shown in FIGS. 17C and 17D, respectively.

EXAMPLE 1

Acetochloroamine ferrate complex was prepared as follows:

124.8 g of solid NaOH was added to 1040 ml of a one molar solution of $FeCl_3$ while stirring. The solution was then let alone for fifteen minutes after the reaction was complete. While stirring, 144 g of ammonium acetate ($NH_4C_2H_3O_2$) was then added to the solution. The solution was filtered to recover a red precipitate. To the precipitate, 80 ml of concentrated acetic acid was added while stirring and then allowed to set for five minutes. 350 ml of concentrated hydrochloric acid was added while stirring for fifteen minutes until the solution became clear. While stirring, 33 g of sodium acetate trihydrate ($NaC_2H_3O.3H_2O$) was added to the solution which yielded about 1100 ml of concetrated acetochloroamine ferrate complex solution.

EXAMPLE 2

A sulfate buffer was prepared by adding 60 ml of concentrated sulfuric acid (1 molar) and 103.55 g sodium hydrogen sulfate ($NaHSO_4.H_2O$) to distilled water and diluting this solution with distilled water to a volume of 1000 ml.

EXAMPLE 3

A concentrated buffered acetochloroamine ferrate photochemical solution was prepared by mixing 1 ml of the concentrated solution of Example 1 with 10 ml of the buffer solution of Example 2. This concentrated solution was then used to prepare a dilute solution of the buffered complex by diluting 1 ml of the concentrated buffered complex containing solution with distilled water to a volume of 500 ml.

EXAMPLE 4

A citratochloroamine ferrate complex was prepared as follows:

326.136 g of green ferric ammonium citrate plus 70.64 g of citric acid plus 620 ml of distilled water were mixed and gently heated until the compounds dissolved. The dissolved solution was then mixed with 381.8975 ml of concentrated hydrochloric acid. The solution was stirred until the solution became a clear amber color.

EXAMPLE 5

A buffer solution for the complex form in Example 4 was prepared as follows:

60 ml of concentrated sulfuric acid (1 molar) was diluted with distilled water to a volume of 500 ml; 103.55 g of $NaHSO_4 \cdot H_2O$ was added to distilled water and diluted with distilled water to a volume of 500 ml and then the two solutions were mixed together to form 1000 ml of $HSO_4^-$ buffer.

EXAMPLE 6

A concentrated buffered citratochloroamine ferrate photochemical solution was prepared by mixing 1 ml of the complex prepared in Example 4 with 10 ml of the buffer of Example 5. A diluted solution was then prepared by diluting 1 ml of the concentrated buffered complex containing solution with distilled water to a volume of 500 ml.

EXAMPLE 7

A cell was constructed which consists of two 1 mm thick polyethylene bags connected by a porous plug bridge. The anode is a lead sheet ⅜ inches wide and about 1/16 inches thick with a mass of 10.9398 g. One half cell comprises the anode immersed in one bag containing 5 ml iron acetate complex (52.8008 mg.Fe/ml) which is diluted with 20 ml of water. The other half cell comprises a cathode immersed in 5 ml of iron citrate (43.4846 mg. Fe/ml) diluted with 20 ml of water. The cathode is a charcoal strip with 1.67 millequivalents (meq) of silver plated thereon. Neither solution contained a buffer. The cells remained outside for almost a year and were shorted (anode to cathode) for the entire time except when voltage and amperage readings were taken. Distilled water was added periodically to make up for evaporation losses. The results are summarized in Table 2 which indicates the time and date for each test. During the testing, it was noted that a residue developed on the cell walls.

EXAMPLE 8

20 Cells were made to test the complex's response to platinum, silver and gold electrodes. The results are summarized in Table 3. The first three columns of Table 3 contain data for concentrated complexes without the buffer. The concentrated buffer was tested and the results are shown at the bottom of the first three columns. The last three columns were prepared by pipetting 2 ml of each complex and 20 ml of buffer into a total volume of 1000 ml $H_2O$. The very weak voltage system appears to be reversible. The letters C and A following the metal symbol indicates citrate and acetate complex, respectively. The diluted buffer readings are shown at the bottom of the last three columns.

EXAMPLE 9

Figure 15:
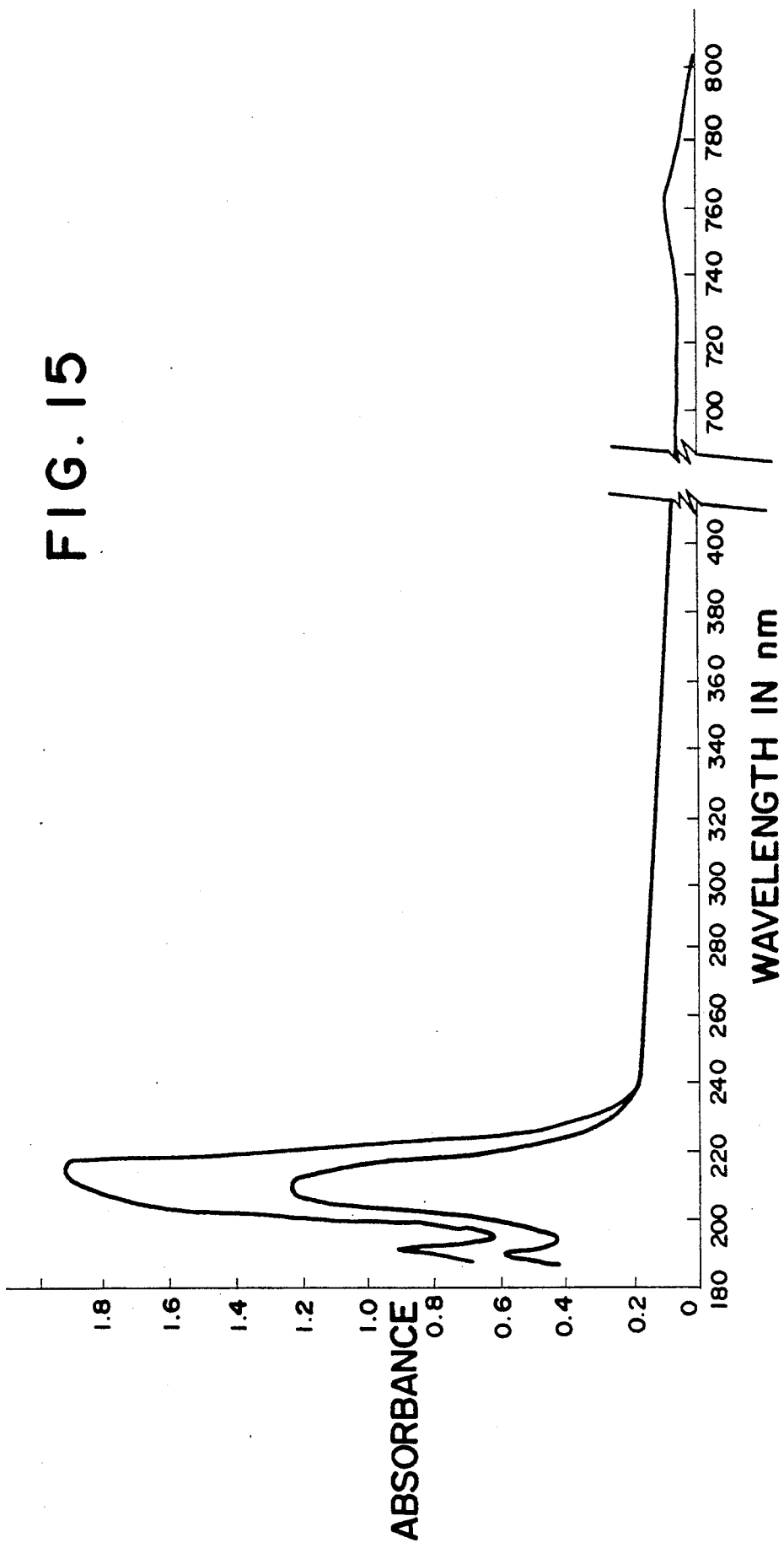
FIG. 15 is a graph which shows the absorbance of an iron acetate complex and an iron citrate complex in cells which have been outside for one year as an electrically close-circuited solar cell.

A cell was made wherein one half cell contains a lead anode immersed in a solution of iron acetate complex and another half cell containing a cathode immersed in a solution of an iron citrate complex. The two solutions were separated by a porcelain bridge. The cathode contains 10% silver ion absorbed on pure carbon then smeared on a strip of charcoal. The cell was kept shorted anode to cathode, closed system, and kept outside for one year, through the four seasons. The concentration is between $10^{-4}$ and $10^{-6}$ molar or less. The solutions coantained no buffer. At the end of the test period, the solutions were tested for their absorbance spectra. The results are shown in FIG. 15. The top line of FIG. 15 is the absorbance spectra of the iron acetate. The iron acetate shows a strong peak near 190 nm and 210 nm and a weak peak near 760 nm. The iron citrate (bottom line) shows peaks near 190 nm and 210 nm and a weak peak near 760 nm.

EXAMPLE 10

A cell was prepared with a lead anode and a lead carbide cathode, both of which were immersed in an iron acetate complex solution in a polyethylene container. The solution was prepared by mixing 2 ml of the solution prepared in Exmaple 1 with 20 ml of the concentrated buffer solution prepared in Example 2 and then diluting the solution with distilled water to bring the volume to 1000 ml. The lead anode was poisoned with $SO_4^{-2}$ from concentrated sulfuric acid. The cell contents are 0.1056016 mg. iron ion; 0.058 meq. hydrogen ion from the buffer; 4.54 ml of lead anode. The anode was 40% exposed to the solution. The lead carbide cathode was made by absorbing 10% lead on 90% carbon and binding in an equal mass of paraffin as a binder. Both half cells were exposed to light. Voltage and amperage tests were taken over an extended period of time during which time the cells were kept shorted except when test readings were taken. The results of the tests are summarized in Table 4. At the conclusion of the tests, it was noted that the electrodes were the same size and composition as they were when the test began. Thus, the electrodes were not consumed during the period that they produced electric current.

EXAMPLE 11

A cell was prepared with a lead anode and a lead carbide cathode, both of which were immersed in an iron citrate complex solution in a polyethylene container. The solution was prepared by mixing 2 ml of concentrated iron citrate complex prepared in Example 4 with 20 ml of concentrated buffer prepared in Example 5 and diluting the solution with distilled water to bring the volume to 1000 ml. The cell contains 0.0869692 mg. of iron ion; 0.058 meq. of hydrogen ion from the buffer; 3.90 mg. of lead anode which was poisoned with $SO_4^{-2}$ and the anode was 43% exposed to the solution. The lead carbide cathode comprised lead absorbed upon carbon to produce 10% lead and 90% carbon, and a mass of paraffin binder which was equal to the total amount of lead and carbon in the cathode. The cell was exposed to light for a period of time during which time periodic tests were made to measure voltage and amperage. During the testing, the cell was kept shorted except when the measurements were taken. The results are summarized in Table 5.

TABLE 1

| Complex | Central metal ions concentration at start of synthesis in mg/ml | Ammonia ligand in mg/ml | Citrate ligand in mg/ml | Acetate ligand in mg/ml | Chloride ligand in mg/ml |
|---|---|---|---|---|---|
| Tin acetate | 42.9457 | 0.00 | — | 0.00 | 7.9769 |
| Tin citrate | 51.1008 | 0.00 | 0.00 | — | 4.4316 |
| Iron acetate | 52.0809 | 0.0828 | — | 15.732 | 49.8115 |
| Iron citrate | 43.4846 | 0.1656 | 101.568 | — | 29.2487 |
| Aluminum acetate | 7.7028 | 0.00 | — | 24.84 | 2.6590 |
| Aluminum citrate | 10.2749 | 0.00 | 22.3008 | — | 0.4254 (trace) |
| Chromium acetate | 14.8921 | 0.9384 | — | 31.4364 | 27.4761 |
| Chromium citrate | 18.8907 | 0.00 | 40.986 | — | 1.7726 |
| Magnesium acetate | 33.6682 | 0.9384 | — | 69.66 | 32.7940 |
| Magnesium citrate | 41.9614 | 0.9384 | 146.1692 | — | 70.0197 |
| Cobalt acetate | 48.1254 | $NH_3$ odor only | — | 24.5916 | 13.2949 |
| Cobalt citrate | 57.3882 | 0.0414 | 52.992 | — | 12.4085 |
| Calcium acetate | 40.0822 | $NH_3$ odor only | — | 65.6604 | 14.1812 |
| Calcium citrate | 35.2178 | 0.00 | 22.77 | — | 2.6590 |
| Nickel acetate | 53.3974 | 0.5382 | — | 46.368 | 36.3393 |
| Nickel citrate | 38.7354 | 0.00 | 39.9924 | — | 50.8751 |
| Manganese acetate | 29.8529 | 0.00 | — | 25.806 | 11.6995 |
| Manganese citrate | 27.13 | 0.00 | 18.8784 | — | 10.4586 |
| Zinc acetate | 80.376 | 0.7819 | — | 37.8672 | 43.4299 |
| Zinc citrate | 80.6485 | 0.0828 | 22.356 | — | 4.7862 |
| Copper acetate | 29.6078 | 0.00 | — | 2.3184 | 6.2043 |
| Copper citrate | 33.4899 | 0.00 | 32.4852 | — | 3.5453 |

Data Table 1: Analytical data of the metallic complex that was precipitated with 6 N NaOH. Ammonia, citrate and acetate concentrations were obtained by extrapolating infrared spectroscopy data from a standard graph. The chloride concentration was obtained by washing the NaOH treated complex with pure water and dissolving the precipitate in 2 N $N_2SO_4$. The chloride ion in the complex was titrated with 0.1 N silver nitrate.

TABLE 2

| Date Time volts; mil.amp. | Date Time volts; mil.amp. | Date Time volts; mil.amp. | Date Time volts; mil.amp. | Date Time volts; mil.amp. | Date Time volts; mil.amp. |
|---|---|---|---|---|---|
| 8/7/80 8:05 PM 0.60; 0.64 | 8/7/80 11:20 PM 0.63; 0.65 | 8/8/80 9:20 AM 0.75; 0.60 | 8/8/80 1:20 PM 0.67; 0.72 | 8/8/80 10:15 PM 0.65; 0.37 | 8/9/80 4:20 AM 0.66; 0.32 |
| 8/9/80 11:05 AM 0.66; 0.48 | 8/9/80 4:10 PM 0.65; 0.57 | 8/10/80 1:00 AM 0.67; 0.25 | 8/10/80 4:20 PM 0.67; 0.46 | 8/10/80 11:05 PM 0.66; 0.20 | 8/12/80 4:00 PM 0.66; 0.32 |
| 8/12/80 11:40 PM 0.66; 0.15 | 8/13/80 6:05 AM 0.67; 0.15 | 8/13/80 4:15 PM 0.65; 0.21 | 8/13/80 11:35 PM 0.65; 0.14 | 8/14/80 2:05 PM 0.65; 0.15 | 8/15/80 2:15 PM 0.67; 0.23 |
| 8/15/80 11:00 PM 0.65; 0.12 | 8/16/80 11:00 PM 0.65; 0.13 | 8/17/80 4:10 PM 0.63; 0.14 | 8/17/80 10:35 PM 0.62; 0.10 | 8/18/80 12:15 PM 0.64; 0.23 | 8/18/80 4:03 PM 0.64; 0.23 |
| 8/19/80 5:15 PM 0.64; 0.24 | 8/20/80 1:05 AM 0.63; 0.10 | 8/20/80 2:50 PM 0.62; 0.23 | 8/20/80 11:00 PM 0.63; 0.08 | 8/21/80 2:25 PM 0.65; 0.23 | 8/22/80 7:10 AM 0.60; 0.06 |
| 8/22/80 1:30 PM 0.65; 0.28 | 8/23/80 12:01 AM 0.62; 0.08 | 8/23/80 4:41 PM 0.62; 0.08 | 8/23/80 11:45 PM 0.63; 0.09 | 8/24/80 2:10 PM 0.65; 0.26 | 8/25/80 12:06 PM 0.65; 0.20 |
| 8/25/80 11:20 PM 0.64; 0.10 | 8/26/80 2:15 PM 0.63; 0.40 | 8/26/80 11:15 PM 0.63; 0.11 | 8/27/80 3:10 PM 0.65; 0.33 | 8/27/80 9:25 PM 0.61; 0.21 | 8/28/80 12:02 PM 0.57; 0.23 |
| 8/28/80 3:05 PM 0.55; 0.33 | 8/29/80 2:45 PM 0.53; 0.23 | 8/29/80 10:55 PM 0.55; 0.10 | 8/31/80 11:30 AM 0.53; 0.12 | 10/8/80 6:25 PM 0.51; 0.10 | 10/10/80 3:10 PM 0.50; 0.14 |
| 10/22/80 3:45 PM 0.45; 0.10 | 10/25/80 8:25 PM 0.45; 0.10 | 10/28/80 4:24 PM 0.45; 0.10 | 12/14/80 1:20 PM 0.48; 0.12 | 1/2/81 2:40 PM 0.30; 0.011 | 1/5/81 2:15 PM 0.25; 0.007 |
| 1/5/81 2:16 PM 0.37; 0.06 added $H_2O$ | 1/7/81 2:05 PM 0.30; 0.06 | 2/18/81 3:30 PM 0.24; 0.15 | 3/8/81 7:55 PM 0.33; 0.05 | 3/8/81 7:56 PM 0.35; 0.13 added $H_2O$ | 3/8/81 11:15 PM 0.27; 0.10 |
| 3/13/81 3:45 PM 0.23; 0.07 | 6/5/81 3:40 PM 0.25; 0.04 | 6/14/81 7:10 PM 0.25; 0.04 | 6/23/81 12:45 PM 0.00; 0.00 added $H_2O$ | 6/23/81 12:45 PM 0.40; 0.10 | 7/6/81 2:45 PM 0.43; 0.04 |
| Cell was broken while drawing a sample to | 9/4/81 3:00 PM | Due to the leaking cell, the test was terminated. | | | |

TABLE 2-continued

| Date Time volts; mil.amp. | Date Time volts; mil.amp. | Date Time volts; mil.amp. | Date Time volts; mil.amp. | Date Time volts; mil.amp. | Date Time volts; mil.amp. |
|---|---|---|---|---|---|
| run U.V.-vis. | 0.30; 0.018 | | | | |

Data Table 2:
The cell consists of two 1 mm thick polyethylene bags connected by a porous plug bridge. Anode is a lead sheet ⅜ in. wide about 1/16 in. thick with a mass of 10.9398 grams, with 5 ml of iron acetate complex which is 52.8008 mg Fe/ml. Cathode is charcoal strip with 1.67 meq of silver plated on it, with 5 ml of iron citrate which is 43.4846 mg Fe per ml. Added 20 ml of pure water to each half cell. The solutions coantained no buffer. The cell remained outside and shorted all year.

TABLE 3

| Complex | Electrodes Au; Pt volts; mil.amp. | Electrodes Au; Ag volts; mil.amp. | Electrodes Pt; Ag volts; mil.amp. | Electrodes Au; Pt volts; mil.amp. | Electrodes Au; Ag volts; mil.amp. | Electrodes Pt; Ag volts; mil.amp. |
|---|---|---|---|---|---|---|
| FeC | −; + 0.22; 0.13 | +; − 0.46; 0.74 | +; − 0.48; 1.05 | −; + 0.05; 0.0023 | +; − 0.13; 0.0125 | +; − 0.16; 0.0075 |
| FeA | −; + 0.03; 0.0055 | −; + 0.30; 0.35 | +; − 0.56; 1.10 | −; + 0.08; 0.0045 | +; − 0.27; 1.03 | +; − 0.33; 0.06 |
| ZnA | −; + 0.06; 0.0006 | +; − 0.22; 0.04 | +; − 0.14; 0.004 | −; + 0.13; 0.003 | +; − 0.05; 0.0023 | +; − 0.14; 0.0075 |
| ZnC | −; + 0.04; 0.0004 | +; − 0.22; 0.04 | +; − 0.20; 0.0006 | −; + 0.10; 0.0033 | +; − 0.08; 0.0042 | +; − 0.16; 0.0155 |
| AlA | −; + 0.05; 0.0024 | +; − 0.44; 0.05 | +; − 0.26; 0.07 | −; + 0.09; 0.0027 | +; − 0.15; 0.004 | +; − 0.17; 0.0155 |
| AlC | −; + 0.15; 0.0045 | +; − 0.5; 0.07 | +; − 0.42; 0.05 | +; − 0.08; 0.0022 | +; − 0.07; 0.0035 | +; − 0.16; 0.0099 |
| CrA | −; + 0.16; 0.005 | +; − 0.36; 0.04 | +; − 0.28; 0.017 | −; + 0.14; 0.0044 | +; − 0.07; 0.0023 | +; − 0.14; 0.011 |
| CrC | −; + 0.03; 0.0012 | +; − 0.47; 0.10 | +; − 0.26; 0.0057 | −; + 0.10; 0.0025 | +; − 0.08; 0.004 | +; − 0.18; 0.0165 |
| MgC | −; + 0.03; 0.006 | +; − 0.18; 0.0158 | +; − 0.24; 0.0046 | −; + 0.12; 0.0035 | +; − 0.12; 0.0045 | +; − 0.16; 0.0193 |
| MgA | +; − 0.06; 0.001 | +; − 0.29; 0.04 | +; − 0.15; 0.005 | −; + 0.10; 0.0038 | +; − 0.05; 0.0032 | +; − 0.16; 0.013 |
| CuA | −; + 0.22; 0.07 | +; − 0.21; 0.33 | +; − 0.42; 0.76 | −; + 0.07; 0.0025 | +; − 0.04; 0.0038 | +; − 0.13; 0.007 |
| CuC | −; + 0.00; 0.0005 | +; − 0.35; 0.72 | +; − 0.35; 0.66 | −; + 0.13; 0.0043 | +; − 0.007; 0.0065 | +; − 0.15; 0.0125 |
| CoA | −; + 0.16; 0.0065 | +; − 0.33; 0.13 | +; − 0.35; 0.08 | −; + 0.05; 0.002 | +; − 0.13; 0.0065 | +; − 0.15; 0.0093 |
| CoC | −; + 0.03; 0.0003 | +; − 0.24; 0.05 | — 0.00; 0.00 | −; + 0.12; 0.003 | +; − 0.04; 0.0026 | +; − 0.16; 0.013 |
| CaA | −; + 0.05; 0.013 | +; − 0.22; 0.04 | +; − 0.17; 0.0095 | — 0.00; 0.00 | +; − 0.09; 0.0075 | +; − 0.16; 0.015 |
| CaC | −; + 0.02; 0.0025 | +; − 0.27; 0.05 | +; − 0.13; 0.0047 | −; + 0.07; 0.0033 | +; − 0.07; 0.0045 | +; − 0.17; 0.0065 |
| NiA | −; + 0.03; 0.006 | +; − 0.26; 0.04 | +; − 0.16; 0.005 | −; + 0.07; 0.0032 | +; − 0.07; 0.0035 | +; − 0.13; 0.006 |
| NiC | −; + 0.04; 0.009 | +; − 0.20; 0.05 | +; − 0.16; 0.0053 | −; + 0.16; 0.0026 | +; − 0.05; 0.0026 | +; − 0.14; 0.0085 |
| MnC | −; + 0.01; 0.0002 | +; − 0.41; 0.06 | +; − 0.14; 0.0043 | −; + 0.09; 0.0015 | +; − 0.12; 0.0065 | +; − 0.16; 0.0123 |
| MnA | −; + 0.16; 0.0065 | +; − 0.47; 0.08 | +; − 0.54; 0.03 | −; + 0.12; 0.0035 | +; − 0.06; 0.0025 | +; − 0.14; 0.0057 |
| SnC | −; + 0.06; 0.003 | +; − 0.13; 0.025 | +; − 0.15; 0.008 | −; + 0.13; 0.0033 | +; − 0.07; 0.0035 | +; − 0.14; 0.0085 |
| SnA | −; + 0.03; 0.0001 | +; − 0.13; 0.02 | +; − 0.13; 0.0085 | −; + 0.14; 0.0045 | +; − 0.05; 0.0022 | +; − 0.17; 0.013 |
| Buffer | +; − 0.04; 0.0015 | +; − 0.13; 0.0035 | +; − 0.06; 0.0013 | +; − 0.04; 0.0005 | +; − 0.015; 0.0036 | +; − 0.00; 0.0006 |

Data Table 3:
Metallic complexes response to platinum, silver and gold electrodes. The first three columns are concentrated complexes without the buffer. The concentrated buffer is tested at the bottom. The last three columns were prepared by pipeting 2 ml of each complex and 20 ml of buffer into a total volume of 1000 ml. The very weak voltage systems appear to be reversible. C and A following the metal symbol means citrate and acetate complex, respectively. The diluted buffer readings are at the bottom of the last three columns.

TABLE 4

| Date Time volts; mil.amp. | Date Time volts; mil.amp. | Date Time volts; mil.amp. | Date Time volts; mil.amp. | Date Time volts; mil.amp. | Date Time volts; mil.amp. |
|---|---|---|---|---|---|
| 9/14/85 1:30 PM 0.57; 0.12 | 9/14/95 2:50 PM 0.46; 0.05 | 9/14/85 5:10 PM 0.40; 0.05 | 9/14/85 11:40 PM 0.03; 0.03 | 9/15/85 11:40 AM 0.42; 0.05 | 9/15/85 3:40 PM 0.36; 0.05 |
| 9/15/85 11:40 PM 0.30; 0.04 | 9/16/85 11:50 AM 0.15; 0.013 | 9/16/85 3:40 PM 0.25; 0.04 | 9/17/85 12:05 AM 0.15; 0.015 | 9/17/85 open - 7:35 PM 0.33; 0.06 | 9/17/85 11:30 PM 0.13; 0.013 |
| 9/18/85 1:15 PM | 9/18/85 4:30 PM | 9/19/85 12:45 AM | 9/19/85 12:15 PM | 9/19/85 4:40 PM | 9/20/85 12:05 AM |

TABLE 4-continued

| Date Time volts; mil.amp. | Date Time volts; mil.amp. | Date Time volts; mil.amp. | Date Time volts; mil.amp. | Date Time volts; mil.amp. | Date Time volts; mil.amp. |
|---|---|---|---|---|---|
| 0.13; 0.018 | 0.12; 0.016 | 0.10; 0.012 | 0.10; 0.018 | 0.10; 0.0185 | 0.06; 0.010 |
| 9/20/85 | 9/21/85 | 9/21/85 | 9/21/85 | 9/22/85 | 9/23/85 |
| 2:10 PM | 12:50 AM | 2:15 PM | 11:30 PM | 2:20 PM | 12:15 AM |
| 0.10; 0.0155 | 0.06; 0.0095 | 0.08; 0.0155 | 0.07; 0.012 | 0.07; 0.011 | 0.06; 0.0105 |
| 9/23/85 | 9/23/85 | 9/24/85 | 9/24/85 | 9/24/85 | 9/25/85 |
| 3:15 PM | 11:30 PM | 12:30 PM | open - 3:00 PM | 11:50 PM | 3:30 PM |
| 0.07; 0.012 | 0.06; 0.01 | 0.10; 0.016 | 0.20; 0.05 | 0.07; 0.013 | 0.06; 0.01 |
| 9/25/85 | 9/26/85 | 9/27/85 | 9/27/85 | 9/27/85 | 9/28/85 |
| 11:45 PM | 3:15 PM | 11:30 PM | 3:15 PM | 11:45 PM | 3:30 PM |
| 0.07; 0.009 | 0.07; 0.0135 | 0.07; 0.012 | 0.07; 0.0135 | 0.07; 0.0125 | 0.06; 0.0115 |
| 9/28/85 | 9/29/85 | 9/29/85 | 9/30/85 | 10/1/85 | 10/1/85 |
| 11:40 PM | 3:30 PM | 11:40 PM | 3:50 PM | 12:10 AM | 10:45 AM |
| 0.06; 0.011 | 0.06; 0.0095 | 0.07; 0.010 | 0.07; 0.0115 | 0.07; 0.0105 | 0.08; 0.0145 |
| 10/1/85 | 10/1/85 | 10/2/85 | 10/2/85 | | |
| 3:00 PM | 11:30 PM | 10:45 AM | 3:30 PM | | |
| 0.018; 0.018 | 0.08; 0.0105 | 0.10; 0.0145 opened the circuit. | 0.20; 0.05 Circuit had been left opened. | | |

Data Table 4:
Iron acetate complex contained one ml of buffered solution and three ml of pure water. The solution was prepared by adding 2 ml of concentrated iron acetate complex and 20 ml of buffer and brought to a total volume of 1000 ml. The cell contents are 0.1056016 mg of iron ion; 0.058 meq of hydrogen ion from the buffer; 4.54 mg of lead anode, which was then poisoned with $SO_4^=$ from concentrated sulfuric acid, the anode is 40% exposed to the solution; PbC cathode which was made by adsorbing 10% lead on 90% carbon and binding in an equal mass of paraffin as a binder. The electrodes appeared the same size and composition after the experiment was concluded.

TABLE 5

| Date Time volts; mil.amp. | Date Time volts; mil.amp. | Date Time volts; mil.amp. | Date Time volts; mil.amp. | Date Time volts; mil.amp. | Date Time volts; mil.amp. |
|---|---|---|---|---|---|
| 9/14/85 | 9/14/85 | 9/14/85 | 9/14/85 | 9/15/85 | 9/15/85 |
| 1:30 PM | 2:50 PM | 5:10 PM | 11:40 PM | 11:40 AM | 3:40 PM |
| 0.74; 0.17 | 0.56; 0.17 | 0.36; 0.08 | 0.25; 0.05 | 0.26; 0.07 | 0.25; 0.05 |
| 9/15/85 | 9/15/85 | 9/16/85 | 9/17/85 | 9/17/85 | 9/17/85 |
| 11:40 PM | 11:50 AM | 3:40 PM | 12:05 AM | open - 7:35 PM | 11:30 PM |
| 0.20; 0.04 | 0.36; 0.05 | 0.23; 0.04 | 0.15; 0.018 | 0.40; 0.06 | 0.15; 0.015 |
| 9/18/85 | 9/18/85 | 9/19/85 | 9/19/85 | 9/19/85 | 9/20/85 |
| 1:15 PM | 4:30 PM | 12:45 AM | 12:15 PM | 4:40 PM | 12:05 AM |
| 0.16; 0.018 | 0.16; 0.018 | 0.15; 0.015 | 0.25; 0.05 | 0.24; 0.05 | 0.20; 0.0225 |
| 9/20/85 | 9/21/85 | 9/21/85 | 9/21/85 | 9/22/85 | 9/23/85 |
| 2:10 PM | 12:50 AM | 2:15 PM | 11:30 PM | 2:20 PM | 12:15 AM |
| 0.20; 0.025 | 0.12; 0.0145 | 0.14; 0.016 | 0.13; 0.014 | 0.11; 0.0105 | 0.11; 0.0115 |
| 9/23/85 | 9/23/85 | 9/24/85 | 9/24/85 | 9/24/85 | 9/25/85 |
| 3:15 PM | 11:30 PM | 12:30 PM | Open - 3:00 PM | 11:50 PM | 3:30 PM |
| 0.12; 0.0103 | 0.10; 0.0105 | 0.14; 0.0157 | 0.26; 0.04 | 0.13; 0.015 | 0.12; 0.0095 |
| 9/25/85 | 9/26/86 | 9/26/85 | 9/27/85 | 9/27/85 | 9/28/85 |
| 11:45 PM | 3:15 PM | 11:30 PM | 3:15 PM | 11:45 PM | 3:30 PM |
| 0.12; 0.0125 | 0.13; 0.013 | 0.12; 0.0125 | 0.16; 0.0285 | 0.11; 0.0105 | 0.11; 0.0105 |
| 9/28/85 | 9/29/85 | 9/29/85 | 9/30/85 | 10/1/85 | 10/1/85 |
| 11:40 PM | 3:30 PM | 11:40 PM | 3:50 PM | 12:10 AM | 10:45 AM |
| 0.11; 0.011 | 0.10; 0.0075 | 0.10; 0.008 | 0.10; 0.0177 | 0.09; 0.0077 | 0.10; 0.011 |
| 10/1/85 | 10/1/85 | 10/2/85 | 10/2/85 | | |
| 3:00 PM | 11:30 PM | 10:45 AM | 3:30 PM | | |
| 0.17; 0.020 | 0.12; 0.0125 | 0.12; 0.012 opened the circuit. | 0.18; 0.018 circuit had been left opened. | | |

Data Table 5:
Iron citrate complex contained one ml of buffered solution and three ml of pure water. The solution was prepared by adding 2 ml of concentrated iron citrate complex and 20 ml of buffer to a total volume of 1000 ml. The cell contents are: 0.0869692 mg of iron ion; 0.058 meq of hydrogen ion from the buffer; 3.90 mg of lead anode, which was then poisoned with $SO_4^=$ and anode is 43% exposed to the solution; PbC cathode which lead adsorbed upon carbon to produce 10% Pb and 90% carbon, then an equal mass of paraffin being part of the 3.90 mg. The electrodes appeared the same after the experiment.

TABLE 6

| Dilute buffered complex | Anode | Cathode | Coulombs for reagents in a straight chemical reaction | Maximum mg, metal ion of complex in experiment | Number of days of data | Coulomb output of active complex of partial experiment |
|---|---|---|---|---|---|---|
| FeA | lead | silver-carbide | 6.09 | 0.1056 (15 ppm) | 158 | 919 |
| FeC | lead | silver-carbide | 6.37 | 0.0870 (12 ppm) | 104 | 152 |
| SnA | lead | silver-carbide | 5.08 | 0.0859 (12 ppm) | 94 | 190 |

TABLE 6-continued

| Dilute buffered complex | Anode | Cathode | Coulombs for reagents in a straight chemical reaction | Maximum mg, metal ion of complex in experiment | Number of days of data | Coulomb output of active complex of partial experiment |
|---|---|---|---|---|---|---|
| SnC | lead | silver-carbide | 5.12 | 0.1022 (15 ppm) | 94 | 356 |
| NiA | lead | silver-carbide | 5.73 | 0.1068 (15 ppm) | 86 | 357 |
| NiC | lead | silver-carbide | 5.08 | 0.0775 (11 ppm) | 77 | 25 |
| AlA | lead | silver-carbide | 5.17 | 0.0154 (2 ppm) | 95 | 128 |
| AlC | lead | silver-carbide | 5.22 | 0.0205 (3 ppm) | 104 | 296 |
| CrA | lead | silver-carbide | 4.97 | 0.1658 (4 ppm) | 95 | 415 |
| CrC | lead | silver-carbide | 5.17 | 0.1052 (5 ppm) | 95 | 277 |
| MgA | lead | silver-carbide | 6.05 | 0.0673 (10 ppm) | 95 | 83 |
| MgC | lead | silver-carbide | 5.97 | 0.0839 (12 ppm) | 95 | 281 |
| ZnA | lead | lead-carbide | 6.08 | 0.1607 (23 ppm) | 95 | 68 |
| ZnC | lead | lead-carbide | 5.63 | 0.1613 (23 ppm) | 93 | 351 |
| CoA | lead | silver-carbide | 5.57 | 0.0963 (14 ppm) | 95 | 148 |
| CoC | lead | silver-carbide | 5.01 | 0.0115 (2 ppm) | 95 | 76 |
| MnA | lead-copper | lead-carbide | 5.50 | 0.0597 (9 ppm) | 95 | 70 |
| MnC | lead-copper | lead-carbide | 5.37 | 0.0543 (8 ppm) | 95 | 27 |
| CuA | lead-copper | platinum | 4.99 | 0.0592 (8 ppm) | 95 | 38 |
| CuC | silver | platinum | 4.79 | 0.0670 (10 ppm) | 95 | 10 |
| CaA | silver | platinum | 5.43 | 0.0802 (11 ppm) | 95 | 14 |
| CaC | lead-copper | silver-carbide | 5.45 | 0.0704 (11 ppm) | 95 | 75 |

Data Table 6:
Two ml of the original synthesized complex plus twenty ml of 1 M $Na_2SO_4$—$H_2SO_4$ buffer were diluted to one liter. One ml of this diluted buffered complex was added to six ml of pure water in each cell containing electrodes. All of the electrodes had been used many times in other solar cell studies. The electrodes were cleaned in 0.1 M HCl prior to their use in this experiment. The cells were placed outside in the sun, electrical readings were taken and each cell's cathode was connected to its own anode, closed circuit. The cells remained outside and shorted, except when voltage and amperage readings were being taken. The solar experiment was conducted during peak sunlight summer season. Voltage and amperage readings were taken at noon and midnight. The average of these readings was used as the twelve hour readings.

TABLE 7

| Complex (A-acetate C-citrate) | Cathode | ml of buffer | ml of complex | Max. ion conc., metal in mg/ml used | Power of liquid Volts:Milliamps | Power dry Volts:Milliamps |
|---|---|---|---|---|---|---|
| FeA | PbC | 30 ml | 20 ml | 52.80 mg/ml | 0.84 v, 1.10 ma | 0.74 v, 0.30 ma |
| FeC | PbC | 30 ml | 20 ml | 43.48 mg/ml | 0.75 v, 0.78 ma | 0.44 v, 0.33 ma |
| ZnC | PbC | 15 ml | 10 ml | 80.64 mg/ml | 0.32 v, 0.50 ma | 0.11 v, 0.10 ma |
| CaC | PbC | 15 ml | 10 ml | 35.22 mg/ml | 0.45 v, 0.25 ma | 0.38 v, 0.08 ma |
| NiA | PbC | 15 ml | 10 ml | 53.40 mg/ml | 0.56 v, 0.64 ma | 0.61 v, 0.80 ma |
| CrA | PbC | 15 ml | 10 ml | 14.89 mg/ml | 0.47 v, 0.47 ma | 0.43 v, 0.019 ma |
| CrC | PbC | 15 ml | 10 ml | 18.89 mg/ml | 0.85 v, 0.25 ma | 0.53 v, 0.16 ma |
| AlA | PbC | 15 ml | 10 ml | 7.70 mg/ml | 0.65 v, 0.85 ma | 0.53 v, 0.60 ma |
| AlC | PbC | 15 ml | 10 ml | 10.27 mg/ml | 0.44 v, 0.67 ma | 0.35 v, 0.05 ma |
| MgA | PbC | 15 ml | 10 ml | 33.67 mg/ml | 0.24 v, 0.37 ma | 0.43 v, 0.24 ma |
| MgC | PbC | 15 ml | 10 ml | 41.96 mg/ml | 0.81 v, 1.70 ma | 0.10 v, 0.023 ma |
| CuA | AgC | 15 ml | 10 ml | 29.61 mg/ml | 0.40 v, 0.60 ma | 0.40 v, 0.10 ma |
| CoA | PbC | 15 ml | 10 ml | 48.13 mg/ml | 0.29 v, 0.51 ma | 0.15 v, 0.22 ma |
| MnA | PbC | 15 ml | 10 ml | 26.85 mg/ml | 0.53 v, 0.77 ma | 0.25 v, 0.07 ma |
| SnA | PbC | 15 ml | 10.ml | 42.95 mg/ml | 0.57 v, 0.34 ma | 0.18 v, 0.02 ma |
| SnC | AgC | 10 ml | 10 ml | 51.10 mg/ml | 0.60 v, 0.39 ma | 0.17 v, 0.06 ma |
| ZnA | PbC | 10 ml | 10 ml | 80.38 mg/ml | 0.43 v, 0.40 ma | 0.20 v, 0.31 ma |
| CoC | PbC | 10 ml | 10 ml | 57.39 mg/ml | 0.73 v, 1.46 ma | 0.26 v, 0.10 ma |
| NiC | PbC | 10 ml | 10 ml | 38.74 mg/ml | 0.73 v, 1.40 ma | 0.06 v, 0.009 ma |
| MnC | AgC | 10 ml | 10 ml | 27.13 mg/ml | 0.40 v, 0.09 ma | 0.26 v, 0.008 ma |
| CaA | PbC | 10 ml | 10 ml | 40.08 mg/ml | 0.65 v, 0.09 ma | 0.39 v, 0.14 ma |

TABLE 7-continued

| Complex (A-acetate C-citrate) | Cathode | ml of buffer | ml of complex | Max. ion conc., metal in mg/ml used | Power of liquid Volts:Milliamps | Power dry Volts:Milliamps |
| --- | --- | --- | --- | --- | --- | --- |
| CuC | PbC | 10 ml | 10 ml | 33.49 mg/ml | 0.35 v, 0.63 ma | 0.04 v, 0.009 ma |

Data Table 7:
Data of the buffered photoelectrochemical complexes in the hydrated solid state form. The anodes are lead and about 0.87 square inches of surface area that is exposed to the hydrated solid residue. The solid residues are deliquescent and due to their low vapor pressure they can dissolve water vapor until they are redissolved. The buffer is 1 M $H_2SO_4$—$NaSO_4$. The cells are covered with a plastic woven sieve to allow sunlight, water vapor and gasses to pass. Cells comprise a cathode and an anode immersed in a photochemical solution contained in a small plastic bag. The circuits remained closed.

TABLE 8

| Complex | Electrodes anode-cathode | Power at start 2:00 PM 7/2/86 | | Power after discharging for about four days | | Power due to sun lamp charging | |
| --- | --- | --- | --- | --- | --- | --- | --- |
| | | volts | milliamps | volts | milliamps | volts | milliamps |
| FeA | Pb—AgC | 0.55 | 0.05 | 0.35 | 0.0125 | 0.43 | 0.253 |
| FeC | Pb—AgC | 0.42 | 0.04 | 0.25 | 0.0018 | 0.43 | 0.05 |
| AlA | Pb—AgC | 0.22 | 0.011 | 0.06 | 0.0035 | 0.13 | 0.0126 |
| AlC | Pb—AgC | 0.30 | 0.012 | 0.04 | 0.0004 | 0.35 | 0.027 |
| CrA | Pb—AgC | 0.27 | 0.0105 | 0.06 | 0.001 | 0.35 | 0.0192 |
| CrC | Pb—AgC | 0.45 | 0.04 | 0.35 | 0.0065 | 0.45 | 0.0185 |
| MgA | Pb—AgC | 0.40 | 0.04 | 0.04 | 0.0004 | 0.27 | 0.0075 |
| MgC | Pb—AgC | 0.33 | 0.015 | 0.08 | 0.001 | 0.24 | 0.007 |
| CoA | Pb—AgC | 0.31 | 0.022 | 0.04 | 0.0004 | 0.15 | 0.0057 |
| CoC | Pb—AgC | 0.35 | 0.0225 | 0.04 | 0.0004 | 0.35 | 0.014 |
| CaA | Ag—Pt (wire) | 0.06 | 0.0008 | 0.05 | 0.0006 | 0.03 | 0.0003 (reversed) |
| CaC | Ag—Pt (wire) | 0.37 | 0.016 | 0.07 | 0.0023 | 0.15 | 0.0043 |
| NiA | Pb—AgC | 0.37 | 0.0195 | 0.07 | 0.0012 | 0.17 | 0.003 |
| NiC | Pb—AgC | 0.27 | 0.012 | 0.05 | 0.0008 | 0.05 | 0.0012 |
| MnA | Pb—PbC | 0.46 | 0.05 | 0.13 | 0.0044 | 0.20 | 0.008 |
| MnC | Pb—PbC | 0.49 | 0.05 | 0.04 | 0.0004 | 0.14 | 0.004 |
| ZnA | Pb—PbC | 0.46 | 0.025 | 0.10 | 0.0013 | 0.13 | 0.0026 |
| ZnC | Pb—PbC | 0.49 | 0.07 | 0.04 | 0.0007 | 0.05 | 0.0009 |
| CuA | Pt—Ag (wire) | 0.05 | 0.0008 | 0.03 | 0.0004 | 0.04 | 0.0004 |
| CuC | Ag—Pt | 0.05 | 0.0006 | 0.00 | 0.0000 | 0.00 | 0.0000 |
| SnA | Pb—AgC | 0.42 | 0.03 | 0.05 | 0.0006 | 0.04 | 0.0004 |
| SnC | Pb—AgC | 0.46 | 0.0213 | 0.03 | 0.0004 | 0.43 | 0.05 |

Data Table 8:
Photographer sun lamp effect on discharged organometallic buffered complexes. A solid state silicon solar cell was placed at the far end of the complexes arrangement, and it was connected to a small motor. When the sun lamp was turned on, and aligned to shine upon all the bags of complexes and solid silicon solar cell the motor ran. The solar charged complexes were shorted, anode connected to the cathode, and stored in a dark closet for about four days, three days and 23 hours. The cells circuit was opened and left open for 5.5 hours while still in the dark closet, to eliminate any problems due to the polarization around the electrodes. Readings were taken by waiting for the needle drift to stop. The sun lamp illuminated the cells for one hour. Readings were taken. The solution was 1 ml dilute complex plus 6 ml pure water.

TABLE 9

| Complex | Electrodes anode-cathode | Complex contained in: | Volts | Milliamps |
| --- | --- | --- | --- | --- |
| Iron acetate | lead-silver carbide | filtrate | 0.26 | 0.0143 |
| Aluminum citrate | lead-silver carbide | filtrate | 0.25 | 0.0227 |
| Tin acetate | lead-silver carbide | filtrate | 0.26 | 0.016 |
| Tin citrate | lead-silver carbide | filtrate | 0.25 | 0.0227 |
| Iron acetate | lead-silver carbide | precipitate | 0.27 | 0.0275 |
| Aluminum citrate | lead-silver carbide | precipitate | 0.25 | 0.0143 |
| Tin acetate | lead-silver carbide | precipitate | 0.26 | 0.0193 |
| Tin citrate | lead-silver carbide | precipitate | 0.28 | 0.0213 |

Data Table 9:
Extracted one ml of the white turbid complex solution which had been functioning outside as a closed circuit, shorted anode to cathode, for two months or more. The cells are those described in data table 6. Centrifuged and decanted the filtrate. Washed the precipitate with about one ml of pure water and added the wash water to the original filtrate. Added pure water to the precipitate to bring it to about the total volume of the filtrate. Determined the voltage and amperage of the complex in the filtrate and the precipitate. Stirred the precipitate solution before taking a reading. The solution with the precipitate was turbid.

While the present invention has been described in terms of certain preferred embodiments and exemplified with respect thereto, one skilled in the art will readily appreciate that variations, modifications, changes, omissions and substitutions may be made without departing from the spirit thereof. It is intended, therefore, that the present invention be limited solely by the scope of the following claims.

I claim:

1. A metal complex for producing electric current in a solar cell; said complex being an iron ion having bonding sites wherein the iron is bonded to a ligand at each bonding site; said ligands being selected from the group consisting of chlorine, ammonia and carboxyl ligands having at least one carboxyl group ionically bonded to the iron; with the proviso that the complex contains at least one chlorine ligand, at least one ammonia ligand and at least one carboxyl ligand wherein said carboxyl ligand is citrate.

2. An iron complex for producing electric current in a solar cell; said complex formed by
   1. forming a first intermediate product in the form of a red precipitate; said precipitate being formed by dissolving NaOH in an aqueous solution of $FeCl_3$ to react the NaOH with the $FeCl_3$; and allowing the solution containing the intermediate product to stand for a period of time effective for digestion; and mixing ammonium acetate into the solution;
   2. removing the red precipitate from the solution;
   3. mixing the red precipitate with concentrated acetic acid to form a second intermediate product;
   4. mixing concentrated hydrochloric acid in the solution containing the second intermediate product until the solution becomes clear; and
   5. mixing sodium acetate into the solution to form the iron complex.

3. A metal complex for producing electric current in a solar cell; said complex being an iron ion having bonding sites wherein the iron ion is bonded to a ligand at each bonding site; said ligands being selected from the group consisting of chlorine, ammonia and carboxyl ligands having at least one carboxyl group ionically bonded to the iron; with the proviso that the complex contains at least one chlorine ligand, at least one ammonia ligand and at least one carboxyl ligand; and said complex is selected from the group consisting of triaceto dichloro amine ferrate; diaceto dichloro diamine ferrate; citrato dichloro diamine ferrate; citrato dichloro amine ferrate; citrato chloro diamine ferrate and citrato trichloro amine ferrate.

4. The complex of claim 1 which is triaceto dichloro amine ferrate.

5. The complex of claim 1 which is diaceto dichloro diamine ferrate.

6. The complex of claim 1 which is citrato dichloro diamine ferrate.

7. The complex of claim 1 which is citrato dichloro amine ferrate.

8. The complex of claim 1 which is citrato chloro diamine ferrate.

9. The complex of claim 1 which is citrato trichloro amino ferrate.

* * * * *